United States Patent
Miao et al.

(10) Patent No.: US 11,160,887 B2
(45) Date of Patent: *Nov. 2, 2021

(54) COMPOSITIONS FOR USE IN DIAGNOSING AND TREATING MELANOMA, INCLUDING METASTATIC MELANOMA AND METHODS RELATED TO SAME

(71) Applicant: UNM RAINFOREST INNOVATIONS, Albuquerque, NM (US)

(72) Inventors: Yubin Miao, Albuquerque, NM (US); Haixun Guo, Louisville, KY (US)

(73) Assignee: UNM Rainforest Innovations, Albuquerque, NM (US)

( * ) Notice: Subject to any disclaimer, the term of this patent is extended or adjusted under 35 U.S.C. 154(b) by 22 days.

This patent is subject to a terminal disclaimer.

(21) Appl. No.: 16/267,477

(22) Filed: Feb. 5, 2019

(65) Prior Publication Data

US 2019/0282716 A1 Sep. 19, 2019

Related U.S. Application Data

(60) Continuation of application No. 15/186,764, filed on Jun. 20, 2016, now Pat. No. 10,265,425, which is a continuation of application No. 14/067,064, filed on Oct. 30, 2013, now Pat. No. 9,393,330, which is a division of application No. 12/811,946, filed as application No. PCT/US2009/000179 on Jan. 12, 2009, now Pat. No. 8,603,435.

(60) Provisional application No. 61/127,561, filed on May 14, 2008, provisional application No. 61/125,087, filed on Apr. 22, 2008, provisional application No. 61/124,635, filed on Apr. 18, 2008, provisional application No. 61/010,652, filed on Jan. 10, 2008.

(51) Int. Cl.

| | |
|---|---|
| *A61K 51/08* | (2006.01) |
| *G01N 33/574* | (2006.01) |
| *G01N 33/60* | (2006.01) |
| *C07K 14/685* | (2006.01) |
| *A61K 9/00* | (2006.01) |
| *A61K 45/06* | (2006.01) |

(52) U.S. Cl.
CPC .......... *A61K 51/088* (2013.01); *A61K 9/0014* (2013.01); *A61K 9/0019* (2013.01); *A61K 9/0053* (2013.01); *A61K 45/06* (2013.01); *C07K 14/685* (2013.01); *G01N 33/5743* (2013.01); *G01N 33/60* (2013.01)

(58) Field of Classification Search
CPC ...... A61K 51/00; A61K 51/08; A61K 51/088; A61K 2121/00; A61K 2123/00; A61K 9/00; A61K 9/0014; A61K 9/0019; A61K 9/0053; A61K 45/00; A61K 45/06; C07K 14/685; G01N 33/5743; G01N 33/60

USPC ... 424/1.1, 1.65, 1.69, 9.1, 9.2, 9.3, 9.4, 9.5; 514/1, 1.1, 19.2, 19.3, 19.4, 19.5, 19.6, 514/19.8, 19.9, 21.5; 530/300, 312, 317, 530/327

See application file for complete search history.

(56) References Cited

U.S. PATENT DOCUMENTS

| | | | |
|---|---|---|---|
| 5,674,839 A | 10/1997 | Hruby | |
| 8,603,435 B2 * | 12/2013 | Miao | C07K 14/685 424/1.69 |
| 8,986,651 B2 * | 3/2015 | Miao | A61K 51/08 424/1.69 |
| 9,005,575 B2 * | 4/2015 | Miao | C07K 14/68 424/1.69 |
| 9,180,214 B1 * | 11/2015 | Miao | G01N 33/60 |
| 9,393,330 B2 * | 7/2016 | Miao | C07K 14/685 |
| 9,463,255 B1 * | 10/2016 | Miao | A61K 51/086 |
| 9,493,537 B2 * | 11/2016 | Miao | C07K 7/54 |
| 10,047,135 B2 * | 8/2018 | Miao | A61K 51/088 |
| 10,238,758 B2 * | 3/2019 | Miao | A61K 51/086 |
| 10,265,425 B2 * | 4/2019 | Miao | C07K 14/685 |

(Continued)

FOREIGN PATENT DOCUMENTS

WO 9100111 A1 1/1991

OTHER PUBLICATIONS

Miao etal, Bioconjugate Chemistry, Jan. 16, 2008, vol. 19, pp. 539-547 (Year: 2008).*

(Continued)

*Primary Examiner* — D. L. Jones
(74) *Attorney, Agent, or Firm* — Henry D. Coleman; R. Neil Sudol

(57) ABSTRACT

The present invention is directed to novel non-invasive diagnostic tools/compounds comprising a cyclic peptide wherein the compound binds to a MSH receptor to image and treat cancers, especially, melanoma, including metastatic melanoma in vivo. The present invention represents a clear advance in the art which presently relies on tissue biopsy for diagnoses of these cancers. The novel imaging probes are capable of detecting cancerous melanoma cells, as well as their metastatic spread in tissues. This represents a quantum step forward in the diagnosis and treatment of melanoma, including metastatic melanoma using non-invasive molecular imaging techniques. The novel probes of the present invention will also be useful to initiate therapy for melanoma as well as monitor patients response to chemotherapy treatments and other interventions or therapies used in the treatment of melanoma/metastatic melanoma. Compounds according to the present invention may be used as diagnostic tools for a number of conditions and diseases states as well as therapeutic agents for treating such conditions and disease states.

23 Claims, 17 Drawing Sheets

(56) References Cited

U.S. PATENT DOCUMENTS 10,464,985 B2 * 11/2019 Miao ............... C07K 14/68
2008/0004213 A1  1/2008 Humphrey

OTHER PUBLICATIONS

Otte A, Mueller-Brand J, Deltas S, Nitzsche EU, Herrmann R, Maecke HR. Yttrium-90-labelled somatostatin-analogue for cancer treatment. Lancet. 1998;351:417-418.
Zamora PO, Bender H, Gulhke S, et al. Pre-clinical experience with Re-188-RC-160, a radiolabeled somatostatin analog for use in peptide-targeted radiotherapy. Anticancer Res. 1997;17:1803-1808.
De Jong M, Breeman WAP, Bernard BF, et al. [177Lu-DOTA0, Tyr3]octreotide for somatostatin receptor-targeted radionuclide therapy. Int J Cancer. 2001;92:628-633.
Haixun Guo, Nalini Shenoy, Benjamin M. Gershman, Jianquan Yang, Larry A. Sklar, Yubin Miao. Metastatic melanoma imaging with an 111In-labeled lactam bridge-cyclized alpha-melanocyte stimulating hormone peptide. Nuclear Medicine and Biology. 2009;36:267-276.
Miao, et al. 111In-Labeled Lactam Bridge-Cyclized alpha-Melanocyte Stimulating HOrmone Peptide Analogues for Melanoma Imaging. Bioconjugate Chemistry, 2008;19:539-547.
Miao Y, et al. Alpha-melanocyte stimulating hormone peptide-targeted melanoma imaging. Frontiers in Bioscience, 2007;12:4514-4524.
McQuade P, et al. Imaging of melanoma using 64Cu and 86Y-DOTA-ReCCMSH(Arg11), a cyclized peptide analogue of alpha-MSH. Journal of Medicinal Chemistry, 2005;48(8):2985-2992.
Jemal, A., Siegel, R., Ward, E., Murray, T., Xu, J., Thun, M. J. Cancer statistics, 2007. (2007) CA Cancer J. Clin. 57, 43-66.
Nabi, H. A., Zubeldia, J. M. (2002) Clinical application of 18F-FDG in oncology. J. Nucl. Med. Technol. 30, 3-9.
Dimitrakopoulou-Strauss, A., Strauss, L. G., Burger, C. (2001) Quantitative PET studies in pretreated melanoma patients: A comparison of 6[18F]fluoro-L-DOPA with 18F-FDG and 15O-water using compartment and non-compartment analysis. J. Nucl. Med. 42, 248-256.
Tatro, J. B., Reichlin, S. (1987) Specific receptors for alpha-melanocyte-stimulating hormone are widely distributed in tissues of rodents. Endocrinology 121, 1900-1907.
Siegrist, W., Solca, F., Stutz, S., Giuffre, L., Carrel, S., Girard, J., Eberle, A. N. (1989) Characterization of receptors for alpha-melanocyte-stimulating hormone on human melanoma cells. Cancer Res. 49, 6352-6358.
Chen, J., Cheng, Z., Hoffman, T. J., Jurisson, S. S., Quinn, T. P. (2000) Melanoma-targeting properties of 99mTechnetium-labeled cyclic α-melanocyte-stimulating hormone peptide analogues. Cancer Res. 60, 5649-5658.
Miao, Y., Owen, N. K., Whitener, D., Gallazzi, F., Hoffman, T. J., Quinn, T. P. (2002) In vivo evaluation of 188Re-labeled alpha-melanocyte stimulating hormone peptide analogs for melanoma therapy. Int. J. Cancer 101, 480-487.
Miao, Y., Whitener, D., Feng, W., Owen, N. K., Chen, J., Quinn, T. P. (2003) Evaluation of the human melanoma targeting properties of radiolabeled alpha-Melanocyte stimulating hormone peptide analogues. Bioconjug. Chem. 14, 1177-1184.
Miao, Y., Owen, N. K., Fisher, D. R., Hoffman, T. J., Quinn, T. P. (2005) Therapeutic efficacy of a 188Re labeled α-melanocyte stimulating hormone peptide analogue in murine and human melanoma-bearing mouse models. J. Nucl. Med. 46, 121-129.
Miao, Y., Hylarides, M., Fisher, D. R., Shelton, T., Moore, H., Wester, D. W., Fritzberg, A. R., Winkelmann, C. T., Hoffman, T. J., Quinn, T. P. (2005) Melanoma therapy via peptide-targeted α-radiation. Clin. Cancer Res. 11, 5616-5621.
Froidevaux, S., Calame-Christe, M., Tanner, H., Sumanovski, L., Eberle, A. N. (2002) A novel DOTA-a-melanocyte-stimulating hormone analog for metastatic melanoma diagnosis. J. Nucl. Med. 43, 1699-1706.

Froidevaux, S., Calame-Christe, M., Schuhmacher, J., Tanner, H., Saffrich, R., Henze, M., Eberle, A. N. (2004) A Gallium-labeled DOTA-a-melanocyte-stimulating hormone analog for PET imaging of melanoma metastases. J. Nucl. Med. 45, 116-123.
Froidevaux, S., Calame-Christe, M., Tanner, H., Eberle, A. N. (2005) Melanoma targeting with DOTA-alpha-melanocyte-stimulating hormone analogs: structural parameters affecting tumor uptake and kidney uptake. J. Nucl. Med. 46, 887-895.
Sawyer, T. K., Hruby, V. J., Darman, P. S., Hadley, M. E. (1982) [half-Cys4,half-Cys10]-a-melanocyte-stimulating hormone: a cyclic a-melanotropin exhibiting superagonist biological activity. Proc. Natl. Acad. Sci. U.S.A. 79, 1751-1755.
Al-Obeidi, F., Hadley, M. E., Pettitt, B. M., Hruby, V. J. (1989) Design of a new class of superpotent cyclic a-melanotropins based on quenched dynamic simulations. J. Am. Chem. Soc. 111, 3413-3416.
Al-Obeidi, F., de L. Castrucci, A. M., Hadley, M. E., Hruby, V. J. (1989) Potent and prolonged-acting cyclic lactam analogs of a-melanotropin: design based on molecular dynamics. J. Med. Chem. 32, 2555-2561.
Fung, S., Hruby, V. J. (2005) Design of cyclic and other templates for potent and selective peptide a-MSH analogues. Current Opinion in Chem. Biol. 9, 352-358.
Giblin, M. F., Wang, N. N., Hoffman, T. J., Jurisson, S. S., Quinn, T. P. (1998) Design and charaterization of a-melanotropin peptide analogs cyclized through rhenium and technetium metal coordination. Proc. Natl. Acad. Sci. U.S.A. 95, 12814-12818.
Chen, J., Cheng, Z., Owen, N. K., Hoffman, T. J., Miao, Y., Jurisson, S. S., Quinn, T. P. (2001) Evaluation of an 111In-DOTA-rhenium cyclized a-MSH analog: a novel cyclic-peptide analog with improved tumor-targeting properties. J. Nucl. Med. 42, 1847-1855.
Aloj, L., Panico, M., Caraco, C., Del Vecchio, S., Arra, C., Affuso, A., Accardo, A., Mansi, R., Tesauro, D., De Luca, S., Pedone, C., Visentin, R., Mazzi, U., Morelli, G., Salvatore, M. (2004) In vitro and in vivo characterization of Indium-111 and Technetium-99m labeled CCK-8 derivatives for CCK-B receptor imaging. Cancer Biotherapy Radiopharm. 19, 93-98.
Miao, Y., Hoffman, T. J., Quinn, T. P. (2005) Tumor-targeting properties of 90Y- and 177Lu-labeled a-melanocyte stimulating hormone peptide analogues in a murine melanoma model. Nucl. Med. Biol. 32, 485-493.
Miao, Y., Benwell, K., Quinn, T. P. (2007) 99mTc and 111In labeled alpha-melanocyte stimulating hormone peptides as imaging probes for primary and pulmonary metastatic melanoma detection. J. Nucl. Med. 48, 73-80.
Volkert, W. A., Hoffman, T. J. (1999) Therapeutic radiopharmaceuticals. Chem. Rev. 99, 2269-2292.
Behr, T. M., Sharkey, R. M., Juweid, M. E., Blumenthal, R. D., Dunn, R. M., Bair, H. J., Wolf, F. G., Becker, W. S., Goldenberg, D. M. (1995) Reduction of the renal uptake of radiolabeled monoclonal antibody fragments by cationic amino acids and their derivatives. Cancer Res. 55, 3825-3834.
Behr, T. M., Becker, W. S., Sharkey, R. M., Juweid, M. E., Dunn, R. M., Bair, H. J., Wolf, F. G., Goldenberg, D. M. (1996) Reduction of renal uptake of monoclonal antibody fragments by amino acid infusion. J. Nucl. Med. 37, 829-833.
Béhé, M., Kluge, G., Becker, W., Gotthardt, M., Behr, T. M. (2005) Use of polyglutamic acids to reduce uptake of radiometal-labeled minigastrin in the kidneys. J. Nucl. Med. 46, 1012-1015.
Rolleman, E. J., Krenning, E. P., Van Gameren, A., Bernard, B. F., De Jong, M. (2004) Uptake of [111In-DTPA0] octreotide in the rat kidney is inhibited by colchicine and not by fructose. J. Nucl. Med. 45, 709-713.
De Jong, M., Barone, R., Krenning, E. P., Bernard, B. F., Melis, M., Vissor, T., Gekle, M., Willnow, T. E., Walrand, S., Jamar, F., Pauwels, S. (2005) Megalin is essential for renal proximal tubule reabsorption of 111In-DTPA-Octreotide. J. Nucl. Med. 46, 1696-1700.
Miao, Y., Fisher, D. R., Quinn, T. P. (2006) Reducing renal uptake of 90Y and 177Lu labeled alpha-melanocyte stimulating hormone peptide analogues. Nucl. Med. Biol. 33, 723-733.

(56) References Cited

OTHER PUBLICATIONS

Liu, S., He, Z., Hsieh, W. Y., Kim, Y. S., Jiang, Y. (2006) Impact of PKM linkers on biodistribution characteristics of the 9mTc-labeled cyclic RGDfK dimer. Bioconjug. Chem. 17; 1499-1507.
Dijkgraaf, I., Liu, S., Kruijtzer, J. A., Soede, A. C., Oyen, W. J., Liskamp, R. M., Corstens, F. H., Boerman, O. C. (2007) Effects of linker variation on the in vitro and in vivo characteristics of an 111In-labeled RGD peptide. Nucl. Med. Biol. 34; 29-35.
Liu, S., Hsieh, W. Y., Jiang, Y., Kim, Y. S., Sreerama, S. G., Chen, X., Jia, B., Wang, F. (2007) Evaluation of a 99mTc-labeled cyclic RGD tetramer for noninvasive imaging integrin αvb3-positive breast cancer. Bioconjug. Chem. 18; 438-446.
Wu, Y., Zhang, X., Xiong, Z., Cheng, Z., Fisher, D. R., Liu, S., Gambhir, S. S., Chen, X. (2005) MicroPET imaging of glioma integrin αvb3 expression using 64Cu-labeled tetrameric RGD peptide. J. Nucl. Med. 46; 1707-1718.
Li, Z. B., Cai, W., Cao, Q., Chen, K., Wu, Z., He, L., Chen, X. (2007) 64Cu-labeled tetrameric and octameric RGD peptides for small-animal PET of tumor αvb3 integrin expression. J. Nucl. Med. 48; 1162-1171.
Dijkgraaf, I., Kruijtzer, J. A., Liu, S., Soede, A. C., Oyen, W. J., Corstens, F. H., Liskamp, R. M., Boerman, O. C. (2007) Improved targeting of the alpha(v)beta(3) integrin by multimerisation of RGD peptides. Eur. J. Nucl. Med. Mol. Imaging. 34; 267-273.
Balch CM, Soong SJ, Gershenwald JE, et al. Prognostic factors analysis of 17,600 melanoma patients: validation of the American joint committee on cancer melanoma staging system. J Clin Oncol. 2001;19:3622-3634.
Gambhir SS. Molecular imaging of cancer with positron emission tomography. Nat Rev Cancer. 2002;2:683-693.
Sharma V, Luker GD, Piwnica-Worms D. Molecular imaging of gene expression and protein function in vivo with PET and SPECT. J Magn Reson Imaging. 2002;16:336-351.
Alonso O, Martinez M, Delgado L, et al. Staging of regional lymph nodes in melanoma patients by means of 99mTc-MIBI scintigraphy. J Nucl Med. 2003;44:1561-1565.
Miao Y, Gallazzi F, Guo H, Quinn TP. 111In-labeled lactam bridge-cyclized alpha-melanocyte stimulating hormone peptide analogues for melanoma imaging. Bioconjug Chem. 2008;19:539-547.
Fidler IJ. Biological behavior of malignant melanoma cells correlated to their survival in vivo. Cancer Res. 1975;35:218-224.
Cheng Z, Mahmood A, Li H, Davison A, Jones AG. [99mTcOAADT]-(CH2)2-NEt2: a potential small-molecule single-photon emission computed tomography probe for imaging metastatic melanoma. Cancer Res. 2005;65:4979-4986.
Winkelmann CT, Figueroa SD, Rold TL, Volkert WA. Microimaging characterization of a B16-F10 melanoma metastasis mouse model. Molecular Imaging. 2006;5:105-114.
Fidler IJ, Kripke ML. Metastasis results from preexisting variant cells within a malignant tumor. Science. 1977;197:893-895.
Vantyghem SA, Postenka CO, Chambers AF. Estrous cycle influences organ-specific metastasis of B16F10 melanoma cells. Cancer Res. 2003;63:4763-4765.
Yang M, Jiang P, An Z, et al. Genetically fluorescent melanoma bone and organ metastasis models. Clin Cancer Res. 1999;5:3549-3559.
Yang M, Baranov E, Jiang P, et al. Whole-body optical imaging of green fluorescent protein-expressing tumors and metastases. Proc Natl Acad Sci USA. 2000;97:1206-1211.
Hoffman RM. Green fluorescent protein imaging of tumour growth, metastasis, and angiogenesis in mouse models. Lancet Oncol. 2002;3:546-556.
Arguello F, Baggs RB, Frantz CN. A murine model of experimental metastasis to bone and bone marrow. Cancer Res. 1988;48:6876-6881.
Otte A, Jermann E, Behe M, et al. A powerful new tool for receptor-mediated radionuclide therapy. Eur J Nucl Med. 1997;24:792-795.

* cited by examiner

Synthetic Flow Scheme

Figure 4, cont.

FIGURE 5
Table 1

| Tissues | $^{111}$In-DOTA-CycMSH | | | | $^{111}$In-DOTA-GlyGlu-CycMSH | | | |
|---|---|---|---|---|---|---|---|---|
| | 2 h | 2 h blockade | 4 h | 24 h | 2 h | 2 h blockade | 4 h | 24 h |
| | Percent injected dose/gram (%ID/g) | | | | | | | |
| Tumor | 9.53±1.41 | 0.29±0.14 | 7.54±0.70 | 2.22±0.51 | 10.40±1.40 | 0.27±0.10 | 7.40±0.43 | 2.37±0.28 |
| Brain | 0.06±0.02 | 0.05±0.04 | 0.05±0.04 | 0.02±0.03 | 0.10±0.07 | 0.01±0.02 | 0.02±0.03 | 0.05±0.04 |
| Blood | 0.09±0.14 | 0.11±0.11 | 0.01±0.00 | 0.05±0.06 | 0.14±0.05 | 0.12±0.11 | 0.02±0.04 | 0.09±0.14 |
| Heart | 0.20±0.18 | 0.17±0.15 | 0.06±0.05 | 0.07±0.13 | 0.16±0.18 | 0.04±0.06 | 0.00±0.00 | 0.09±0.17 |
| Lung | 0.22±0.18 | 0.10±0.10 | 0.11±0.10 | 0.03±0.06 | 0.04±0.03 | 0.12±0.14 | 0.01±0.00 | 0.06±0.05 |
| Liver | 0.17±0.03* | 0.12±0.00 | 0.09±0.07* | 0.11±0.01* | 0.27±0.03 | 0.25±0.05 | 0.21±0.02 | 0.24±0.08 |
| Spleen | 0.39±0.41 | 0.42±0.37 | 0.80±0.39 | 0.22±0.39 | 0.16±0.33 | 0.15±0.14 | 0.27±0.40 | 0.15±0.25 |
| Stomach | 0.10±0.06 | 0.08±0.10 | 0.13±0.15 | 0.02±0.04 | 0.06±0.07 | 0.03±0.05 | 0.02±0.03 | 0.04±0.07 |
| Kidneys | 16.16±1.86* | 16.21±2.33 | 21.69±0.34* | 16.00±2.30* | 13.07±2.49 | 8.61±1.34 | 12.13±1.17 | 9.06±1.82 |
| Muscle | 0.14±0.10 | 0.28±0.32 | 0.01±0.01 | 0.03±0.04 | 0.06±0.12 | 0.13±0.13 | 0.05±0.06 | 0.05±0.06 |
| Pancreas | 0.07±0.06 | 0.13±0.04 | 0.03±0.05 | 0.07±0.06 | 0.07±0.10 | 0.09±0.15 | 0.05±0.08 | 0.02±0.02 |
| Bone | 0.20±0.16 | 0.16±0.14 | 0.04±0.05 | 0.18±0.13 | 0.14±0.07 | 0.42±0.37 | 0.00±0.00 | 0.06±0.05 |
| | Percent injected dose (%ID) | | | | | | | |
| Intestines | 0.34±0.11 | 0.23±0.06 | 0.25±0.08 | 0.05±0.02 | 0.27±0.15 | 0.27±0.06 | 0.15±0.01 | 0.07±0.02 |
| Urine | 91.70±0.62 | 94.53±0.65 | 92.34±0.80 | 94.69±0.49 | 90.32±1.64 | 96.52±0.20 | 92.36±0.74 | 95.04±0.84 |
| | Uptake ratio of tumor/normal tissue | | | | | | | |
| Tumor/Blood | 105.89 | 2.64 | 754.00 | 44.40 | 74.29 | 2.25 | 370.00 | 26.33 |
| Tumor/Kidneys | 0.59 | 0.02 | 0.35 | 0.14 | 0.80 | 0.03 | 0.61 | 0.26 |
| Tumor/Lung | 43.32 | 2.90 | 68.55 | 74.00 | 260.00 | 2.25 | 740.00 | 39.50 |
| Tumor/Liver | 56.06 | 2.42 | 83.78 | 20.18 | 38.52 | 1.08 | 35.24 | 9.88 |
| Tumor/Muscle | 68.07 | 1.04 | 754.00 | 74.00 | 173.33 | 2.08 | 148.00 | 47.40 |

* $P<0.05$, significance comparison between $^{111}$In-DOTA-CycMSH and $^{111}$In-DOTA-GlyGlu-CycMSH at 2, 4 and 24 h post-injection.

FIGURE 13
Table 2

| Tissues | 2 h Lung Met. | 2 h Normal | 4 h Lung Met. | 4 h Normal | 24 h Lung Met. | 24 h Normal |
|---|---|---|---|---|---|---|
| | \multicolumn{6}{c}{Percent injected dose/gram (%ID/g)} | | | | | |
| Lung | 2.00±0.74* | 0.08±0.08 | 1.83±0.12* | 0.05±0.05 | 0.29±0.06* | 0.03±0.02 |
| Blood | 0.12±0.05* | 0.01±0.01 | 0.03±0.03 | 0.02±0.02 | 0.03±0.03 | 0.03±0.02 |
| Bone | 0.02±0.01 | 0.03±0.01 | 0.03±0.03 | 0.06±0.04 | 0.03±0.01 | 0.03±0.01 |
| Brain | 0.01±0.01 | 0.02±0.01 | 0.01±0.01 | 0.01±0.01 | 0.03±0.03 | 0.01±0.01 |
| Heart | 0.20±0.09* | 0.04±0.03 | 0.03±0.01 | 0.03±0.02 | 0.03±0.02 | 0.05±0.04 |
| Kidneys | 16.24±0.62 | 14.11±2.23 | 14.46±0.21 | 14.92±1.50 | 15.13±0.86 | 13.54±1.48 |
| Liver | 0.42±0.07 | 0.41±0.09 | 0.45±0.05 | 0.38±0.01 | 0.13±0.02 | 0.12±0.01 |
| Muscle | 0.04±0.03 | 0.03±0.03 | 0.03±0.02 | 0.03±0.02 | 0.03±0.02 | 0.02±0.01 |
| Skin | 0.26±0.22 | 0.25±0.17 | 0.36±0.08 | 0.23±0.08 | 0.06±0.03 | 0.06±0.01 |
| Spleen | 0.26±0.07* | 0.06±0.04 | 0.11±0.05 | 0.06±0.04 | 0.04±0.03 | 0.04±0.03 |
| Stomach | 0.13±0.05 | 0.14±0.07 | 0.05±0.04 | 0.08±0.06 | 0.05±0.03 | 0.06±0.02 |
| Pancreas | 0.05±0.01 | 0.09±0.07 | 0.10±0.07 | 0.04±0.03 | 0.04±0.02 | 0.06±0.01 |
| | \multicolumn{6}{c}{Percent injected dose (%ID)} | | | | | |
| Intestine | 7.70±2.05 | 7.08±1.54 | 5.97±0.48 | 4.65±0.85 | 0.11±0.03 | 0.11±0.08 |
| Urine | 84.07±2.32 | 84.74±1.97 | 85.67±1.66 | 89.02±0.92 | 95.61±0.59 | 96.06±0.53 |
| | \multicolumn{6}{c}{Uptake ratio of tumor/normal tissue} | | | | | |
| Lung/Blood | 16.67 | 8.0 | 61.0 | 2.5 | 9.67 | 1.0 |
| Lung/Kidney | 0.12 | 0.01 | 0.13 | 0.01 | 0.02 | 0.002 |
| Lung/Liver | 4.76 | 0.20 | 4.07 | 0.13 | 2.23 | 0.25 |
| Lung/Muscle | 50 | 2.67 | 61.0 | 1.67 | 9.67 | 1.5 |

COMPOSITIONS FOR USE IN DIAGNOSING AND TREATING MELANOMA, INCLUDING METASTATIC MELANOMA AND METHODS RELATED TO SAME

RELATED APPLICATIONS

This application claims the benefit of priority of and is a continuation application of U.S. patent application Ser. No. 15/186,764, now U.S. Pat. No. 10,265,425, which is a continuation application of U.S. patent application Ser. No. 14/067,064, now U.S. Pat No. 9,393,330, which is a divisional application of U.S. patent application Ser. No. 12/811,946, now U.S. Pat. No. 8,603,435, which claims the benefit of priority of and is a United States national stage patent application of international patent application no. PCT/US2009/000179 filed Jan. 12, 2009, which claims the benefit of priority of U.S. provisional application Ser. No 61/127,561, filed May 14, 2008; U.S. 61/125,087, filed Apr. 22, 2008; U.S. 61/124,635, filed Apr. 18, 2008 and U.S. 61/010,652, filed Jan. 10, 2008, each of which applications is incorporated by reference in its entirety herein.

GOVERNMENT SUPPORT

The present invention was made with Government support under grant no. DE-AC52-06NA25396 from the United States DOE/NNSA. Consequently, the U.S. government has certain rights in the invention.

FIELD OF THE INVENTION

The present invention is directed to novel non-invasive diagnostic tools/compounds to image cancers, especially, melanoma, including metastatic melanoma in vivo. The present invention represents a clear advance in the art which presently relies on tissue biopsy for diagnoses of these cancers. The novel imaging probes are capable of detecting cancerous melanoma cells, as well as their metastatic spread in tissues. This represents a quantum step forward in the diagnosis and treatment of melanoma, including metastatic melanoma using non-invasive molecular imaging techniques. The novel probes of the present invention will also be useful to initiate therapy for melanoma as well as monitor patients response to chemotherapy treatments and other interventions or therapies used in the treatment of melanoma/metastatic melanoma. Compounds according to the present invention may be used as diagnostic tools for a number of conditions and diseases states as well as therapeutic agents for treating such conditions and disease states.

BACKGROUND OF THE INVENTION

Skin cancer is the most commonly diagnosed cancer in the United States. Malignant melanoma is the most lethal form of skin cancer and the most commonly diagnosed malignancy among young adults with an increasing incidence. It was predicted that there would be 62,940 cases of malignant melanoma newly reported and 8,420 fatalities in 2008 (1). Melanoma metastases are highly aggressive and the survival time for patients with metastatic melanoma averages 3-15 months (2). Unfortunately, no curative treatment exists for metastatic melanoma. Early diagnosis and prompt surgical removal are a patient's best opportunity for a cure. Single photon emission tomography (SPECT) and positron emission tomography (PET) techniques are attractive non-invasive imaging modalities due to their high sensitivity ($10^{-10}$ to $10^{-11}$ M for SPECT and $10^{-11}$ to $10^{-12}$ M for PET) and spatial resolution (1-2 mm) (3, 4). Currently, 2-[$^{18}$F]fluoro-2-deoxy-D-glucose ([$^{18}$F]FDG) PET imaging is commonly used for the diagnosis and staging of melanoma. However, [$^{18}$F]FDG is not a melanoma-specific imaging probe since the elevated uptake of [$^{18}$F]FDG in tumor is due to the higher metabolism and energy consumption in tumor cells than that in normal cells. [$^{18}$F]FDG PET imaging only detects 23% melanoma metastases smaller than 5 mm (5). Meanwhile, some melanoma cells are not detected by [$^{18}$F]FDG PET imaging since they use substrates other than glucose as energy sources (6, 7). Therefore, it is highly desirable to develop novel effective imaging probes to detect primary, metastatic and recurrent melanomas.

BRIEF DESCRIPTION OF THE FIGURES

FIG. 13 shows the biodistribution of $^{111}$In-DOTA-Gly-Glu-CycMSH in B16/F10 pulmonary metastastic melanoma-bearing and normal C57 mice. The data was presented as percent injected dose/gram or as percent injected dose (Mean±SD, n=5).

BRIEF DESCRIPTION OF THE INVENTION

Figure 1:
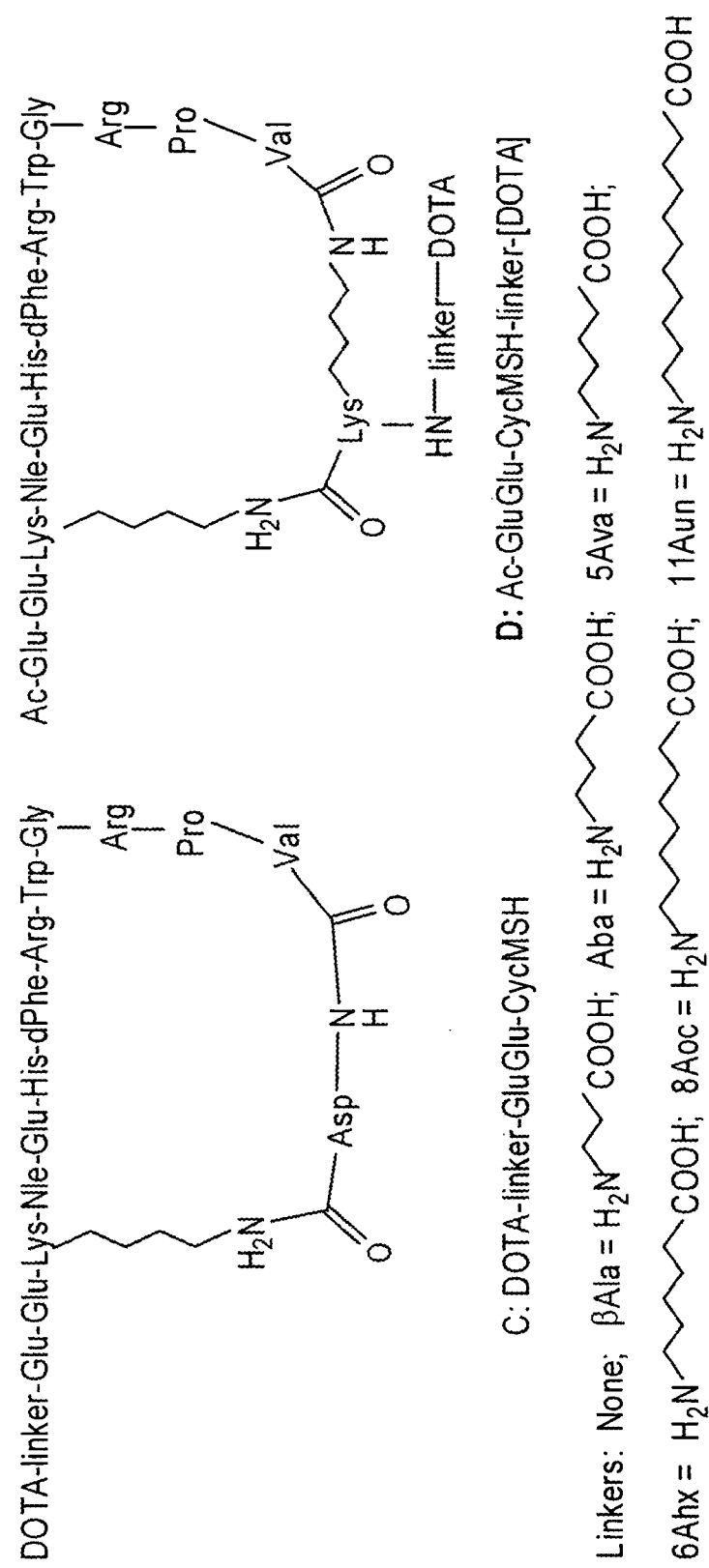
FIG. 1 shows two sub-genuses of compounds according to the present invention wherein the chelate group is DOTA. Note the acylated N-terminal amine group of compound D and the use of a variety of amino acid linkers as otherwise described herein.

The present invention relates to compounds according to the general structure:

(Y)$_q$—X$_m$-(ABC)$_n$-Cycpeptide

Where Y is a chelate group, wherein Y optionally incorporates or complexes with a radioisotope;
Each X is independently an amino acid residue which may be optionally acylated (preferably C$_2$-C$_{20}$ acylated) at its amino terminal end or an amino acid linker according to the chemical structure:

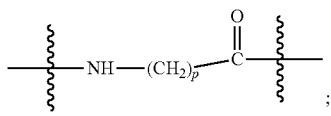

ABC is an amino acid linker wherein
A is absent or is a neutral or negatively charged amino acid at physiological pH which is optionally acylated at its amino terminal end;
B is a neutral or negatively charged amino acid at physiological pH which is optionally acylated (preferably C$_2$-C$_{20}$ acylated) at its amino terminal end;
C is absent or is a neutral or negatively charged amino acid at physiological pH;
m is an integer from 0 to 250, preferably 0 to 5, preferably 0 or 1;
n is 0 or 1, preferably 1;
p is an integer from 0 to 20, preferably 1 to 12, preferably 2 to 8;
q is 0 or 1, and
Cycpeptide is a cyclic peptide comprising between 11 and 13, preferably 12, amino acids according to the structure:

c[Lys-(X)-Glu-His-(Y$^b$)-Arg-Trp-(Z))-Arg-Pro-W-T]

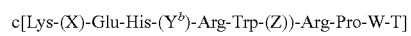

Where X is norleucine (Nle), leucine or isoleucine;
Y$^b$ is D-phenylalanine or L-phenylalanine, preferably D-phenylalanine;
Z is glycine or alanine, preferably glycine;
W is valine, leucine or isoleucine, preferably valine;
T is aspartic acid, glutamic acid or a

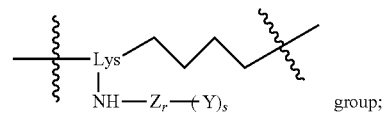

group;

Where Z is an amino acid residue or an amino acid linker according to the chemical structure:

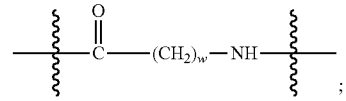

j is 0, 1 or 2, preferably 1,
r is an integer from 0 to 250, preferably 0 to 5, preferably 0 to 1;
s is 1;
w is an integer from 0 to 20, preferably 1 to 12, preferably 2 to 8; or
a pharmaceutically acceptable salt thereof,
optionally complexed with at least one radioisotope, preferably a polyvalent cationic radioisotope, even more preferably selected from the group consisting of $^{86}$Y, $^{90}$Y, $^{111}$In, $^{177}$Lu, $^{225}$Ac, $^{212}$Bi, $^{213}$Bi, $^{66}$Ga, $^{67}$Ga, $^{68}$Ga, $^{64}$Cu, $^{67}$Cu, $^{71}$As, $^{72}$As, $^{76}$As, $^{77}$As, $^{65}$Zn, $^{48}$V, $^{203}$Pb, $^{209}$Pb, $^{212}$Pb, $^{166}$Ho, $^{149}$Pm, $^{153}$Sm, $^{201}$Tl, $^{188}$Re, $^{186}$Re and $^{99m}$Tc.

In preferred aspects of the invention, the compound incorporates or is complexed with a radioisotope as otherwise described herein. In certain aspects of the invention, Y is a radical (i.e., linked to a linker or peptide as otherwise described herein) of DOTA (1,4,7,10-tetraazacyclododecane-1,4,7,10-tetraacetic acid), CB-TE2A (4,11-bis(carboxymethyl)-1,4,8,11-tetraazabicyclo[6.6.2]hexadecane), NOTA (1,4,7-triazacyclononane-1,4,7-triacetic acid), DTPA (Diethylenetriaminopentaacetic acid), MAG$_3$ (Mercaptoacetyltriglycine) and 4,5-bis(2-mercaptoacetamido)pentanoic acid. Other chelating moieties that can complex to radioisotopes are otherwise disclosed herein.

In preferred aspects of the invention, Y is a DOTA radical according to the chemical structure:

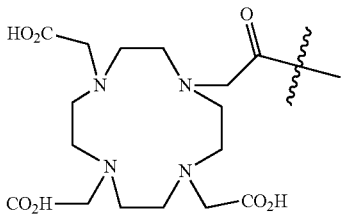

In further preferred aspects of the above-described compounds, n is 1 and ABC is a two amino acid unit linker (A or C is absent) wherein at least one, and in certain instances two of the amino acid units are negatively charged at physiological pH, e.g. aspartic or glutamic acid, preferably glutamic acid. In other preferred aspects, ABC is a two amino acid unit linker wherein at least one of the amino acid units is negatively charged at physiological pH and the other amino acid unit is neutral at physiological pH. Preferably, the neutral amino acid is glycine or alanine, preferably glycine. Preferably, the amino acid linker is an AB linker (C is absent) wherein A is glycine, glutamic acid or aspartic acid and B is glutamic acid or aspartic acid (GlyGlu, GlyAsp, GluGlu, GluAsp, AspGlu or AspAsp). It is noted that compounds according to the present invention which contain an ABC amino acid linker (as opposed to those without a linker) and especially a linker having at least one negatively charged amino acid (e.g., aspartic acid or glutamic acid), often exhibit less renal uptake and consequently enhanced pharmacokinetics (longer half-life in vivo) than do compounds according to the present invention which do not contain such linkers. AB linkers (where C is absent) wherein A is glycine or alanine, especially glycine and wherein B is glutamic acid or aspartic acid may also be preferred.

In alternative embodiments, q is 0 (Y is absent) and T is a

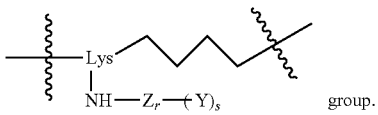

group.

Preferably r is an integer from 0 to 5, preferably 1 to 5. Y is preferably a radical of DOTA (1,4,7,10-tetraazacyclododecane-1,4,7,10-tetraacetic acid), CB-TE2A (4,11-bis(carboxymethyl)-1,4,8,11-tetraazabicyclo[6.6.2]hexadecane), NOTA (1,4,7-triazacyclononane-1,4,7-triacetic acid), DTPA (Diethyl enetriaminopentaacetic acid), MAG$_3$ (Mercaptoacetyltriglycine) or 4,5-bis(2-mercaptoacetamido)pentanoic acid. More preferably, Y is a radical of DOTA, optionally complexed with a radioisotope as otherwise described herein.

In preferred embodiments, the present invention relates to the above compounds, including pharmaceutically acceptable salts, wherein the compound, especially the Y group, is complexed with a radioisotope (which may be a neutral species or a cationic species, and is preferably a polyvalent cationic species) selected from the group consisting of $^{86}$Y, $^{90}$Y, $^{111}$In, $^{177}$Lu, $^{225}$Ac, $^{212}$Bi, $^{213}$Bi, $^{66}$Ga, $^{67}$Ga, $^{68}$Ga, $^{64}$Cu, $^{67}$Cu, $^{71}$As, $^{72}$As, $^{76}$As, $^{77}$As, $^{65}$Zn, $^{48}$V, $^{203}$Pb, $^{209}$Pb, $^{212}$Pb, $^{166}$Ho, $^{149}$Pm, $^{153}$Sm, $^{201}$Tl, $^{188}$Re, $^{186}$Re and $^{99m}$Tc.

In further embodiments, Y is a DOTA moiety which may be complexed with a radioisotope as indicated (this general structure also contemplates one or more carbonyl/carboxyl groups in the molecule also being complexed to the radioisotope and is non-limiting) according to the following:

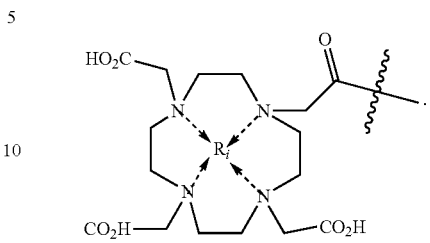

Where Ri is a radioisotope (which may be a neutral species or a cationic species, and is preferably a polyvalent cationic species) selected from the group consisting of $^{86}$Y, $^{90}$Y, $^{111}$In, $^{177}$Lu, $^{225}$Ac, $^{212}$Bi, $^{213}$Bi, $^{66}$Ga, $^{67}$Ga, $^{68}$Ga, $^{64}$Cu, $^{67}$Cu, $^{71}$As, $^{72}$As, $^{76}$As, $^{77}$As, $^{65}$Zn, $^{48}$V, $^{203}$Pb, $^{209}$Pb, $^{212}$Pb, $^{166}$Ho, $^{149}$Pm, $^{153}$Sm, $^{201}$Tl, $^{188}$Re, $^{186}$Re and $^{99m}$Tc.

Radioisotopes are selected based on the physical half life, the decay mode (alpha, beta, auger, gamma, X-ray) and the energy of the radioisotope. In diagnostic aspects of the present invention, preferred radioisotopes include, for example, $^{111}$In, $^{86}$Y, $^{66}$Ga, $^{67}$Ga, $^{68}$Ga, $^{203}$Pb, $^{64}$Cu and $^{99m}$Tc.

Where compounds are to be analyzed using positron emission tomography or PET imaging they are labeled with a positron emitting radioisotopes such as: $^{66}$Ga, $^{68}$Ga, $^{64}$Cu, $^{86}$Y, or other polyvalent, cationic radiometals that decay by positron emission. In alternative embodiments, the compounds may be analyzed using single photon emission computed tomography or SPECT imaging when labeled with a gamma radiation emitting radioisotope which preferably includes $^{111}$In, $^{67}$Ga, $^{99m}$Tc and $^{203}$Pb or other gamma emitting radioisotope as disclosed herein.

The present invention relates to compounds and/or compositions which may be used to prepare imaging/therapeutic agents or as imaging/therapeutic agents (when complexed with a radioisotope) for diagnosing and treating melanoma, including metastatic melanoma as otherwise described herein. Compounds according to the present invention which are complexed with an appropriate radioisotope may be used to diagnose the existence and/or extent of melanoma, including metastatic melanoma, monitor therapy as a therapeutic aid of melanoma, including metastatic melanoma, and in certain instances, function as a therapeutic agent (peptide targeted radiation) for the treatment of melanoma, including metastatic melanoma.

The present invention also relates to pharmaceutical compositions comprising an effective amount of a compound according to the present invention which has been complexed with a radioisotope and combined with a carrier, additive or excipient in pharmaceutical dosage form as a diagnostic imaging agent or as a therapeutic agent. Compositions according to the present invention are formulated in pharmaceutical dosage form for administration preferably by a parenteral, preferably an intravenous route. Compositions according to the present invention may also be formulated for administration via a topical route, directly to the skin. Oral compositions may also be formulated for use in the present invention.

In the diagnostic method according to the present invention, a compound according to the present invention is administered to a patient, and evidence of elevated expression of MSH receptors in tissue of said patient through standard well-known nuclear imaging techniques, especially radiation (radionuclide) imaging, including scintigraphic imaging, and especially single photon emission computed tomography (SPECT) and positron emission tomography (PET) in comparison to a normal standard, is indicative of a disease state (melanoma) and extent of disease state (metastasis) in the tissue of the patient. The nuclear imaging techniques useful in the present diagnostic methods are well known in the art. In general, elevated levels of radiation emanating from a diagnosed tissue is evidence of elevated MSH receptor activity and indicative of a disease state or condition (melanoma and/or metastatic melanoma) wherein these receptors are found at elevated levels. Methods of diagnosing the existence and/or extent (stage) of melanoma, including metastatic melanoma are therefore additional aspects of the present invention. Thus, a diagnostic method of diagnosing the existence or absence of melanoma in a patient at risk for melanoma comprises administering to said patient a compound according to the present invention; imaging said patient to determine if tissue in said patient exhibits elevated expression of MSH receptors; and diagnosing said patient as having melanoma, including metastatic melanoma if said tissue evidences elevated expression of MSH receptors in comparison to a standard.

Methods of monitoring the treatment of melanoma, including metastatic melanoma in conjunction with traditional or experimental melanoma therapy is an additional aspect of the invention. In this aspect, a patient's response to therapy is monitored using the methods according to the present invention. In this method, a patient is monitored before and after therapy by administering compound according to the present invention and determining (through imaging diagnostics as otherwise described herein) the extent of expression of melanocyte stimulating hormone receptors in tissues of a patient before therapy and after therapy and comparing the expression levels with each other and/or with a standard (predetermined value) to determine the extent of reduction of cancer tissue which occurred pursuant to the therapeutic intervention.

Methods of treating melanoma represent a further aspect of the invention. In this aspect, compounds according to the present invention as described above are administered to a patient known to have melanoma and/or metastatic melanoma in effective amounts in order to reduce cancer tissue and otherwise treat the patient's cancer through targeted radiation therapy. The present therapeutic methods may be used alone or in combination with other treatment methods (surgery, chemotherapy, radiation therapy and/or immunotherapy (IL-2 and α-interferon) for melanoma/metastatic melanoma as otherwise disclosed herein. In preferred therapeutic method aspects of the present invention, compounds according to the present invention are labeled with $^{90}$Y, $^{177}$Lu, $^{186}$Re, $^{188}$Re, $^{212}$Bi/$^{212}$Pb, $^{213}$Bi, $^{149}$Pm, $^{166}$Ho and $^{153}$Sm and are administered to the patient (preferably intravenously or topically—i.e, directly onto the melanoma tissue in the skin of the patient) in order to target the malignant melanoma tumor, including metastatic melanoma tissue with radiation therapy.

DETAILED DESCRIPTION OF THE INVENTION

The following terms are used to describe the present invention. In the event that a term is not specifically defined herein, that term is accorded its commonly understood meaning within the context of its use by those of ordinary skill in the art. It is understood that the definitions of the terms which are used to describe the present invention are interpreted in a manner consistent with the present invention and within the context of a particular term's use in describing the present invention in one or more embodiments.

As used herein and in the appended claims, the singular forms "a," "an," and "the" include plural reference unless the context clearly dictates otherwise. Thus, for example, a reference to "a compound", within context, includes a plurality (for example, two or more compounds) of such elements, and so forth. Under no circumstances is the patent be interpreted to be limited to the specific examples or embodiments or methods specifically disclosed herein.

The term "patient" or "subject" is used throughout the specification to describe an animal, preferably a human, to whom treatment, including prophylactic treatment, with the compounds according to the present invention is provided. For treatment of those infections, conditions or disease states which are specific for a specific animal such as a human patient, the term patient refers to that specific animal.

The term "compound" is used herein to refer to any specific chemical compound disclosed herein. Within its use in context, the term generally refers to a single oligopeptide, or an oligopeptide bonded to a DOTA group optionally complexed with a radioisotope, but in certain instances may also refer to components/portions of such compounds, intermediates used to synthesize such compounds, stereoisomers and/or optical isomers (including racemic mixtures) of disclosed compounds. The term compound shall include, where applicable, any and all relevant pharmaceutically acceptable salts thereof.

The term "neutral amino acid" is an amino acid which has an uncharged sidechain at physiological pH. Neutral amino acids for use in the present invention include, for example, glycine, alanine, valine, leucine, isoleucine, norleucine, methionine, phenylalanine, serine, threonine and tyrosine. Preferred neutral amino acids include glycine, alanine, valine, leucine, isoleucine and norleucine. The term "negatively charged amino acid" is an amino acid which has a negatively charged sidechain at physiological pH. Preferred negatively charged amino acids for use in the present invention include glutamic acid and aspartic acid, both of which contain a plurality of carboxylate anions (in contrast to free/protonated carboxylic acids) at physiological pH.

The term "chelate", "chelator" or "chelating agent" is used to describe a moiety (as represented by Y in generic structures) which is functionally capable of complexing or "chelating" a radioisotope as otherwise described herein. Each is appropriately chemically linked (via covalent linkers or directly to Cyclic peptides as otherwise described herein). Exemplary chelators for use in the present invention, which are well known in the art, include the following:
Polyaminocarboxylates, such as
EDTA: ethylenediaminetetraacetic acid
DTPA: diethylenetriaminepentaacetic acid
Polyaminocarboxylic Macrocycles, such as:
DOTA: 1,4,7,10-tetraazacyclododecane-1,4,7,10-tetraacetic acid
TRITA: 1,4,7,10-tetraazacyclotridecane-1,4,7,10-tetraacetic acid
TETA: triethylenetetramine bridged-cyclam-2a: 1,4,8,11-tetraazabicyclo[6.6.2]hexadecane-1,8-di(methanephosphonic acid)
DO3A: 1,4,7-tris(carboxymethyl)-1,4,7,10-tetraazacyclododecane
DO2A: 1,4,7,10-tetraazacyclododecane-1,7-bis(acetic acid)

Other Chelators, such as:
CB-TE2A (4,11-bis(carboxymethyl)-1,4,8,11-tetraazabicyclo[6.6.2]hexadecane)
NOTA (1,4,7-triazacyclononane-1,4,7-triacetic acid)
$MAG_3$ (Mercaptoacetyltriglycine)
4,5-bis(2-mercaptoacetamido)pentanoic acid.

Chelates, chelators or chelating agents are generally bi- or multidentate ligands which generally produce a binding or complexation (complex) of a metal radioisotope as otherwise described herein. The ligand or chelator forms a chelate complex with the substrate. The term, without limitation, is used to describe complexes in which the metal ion is bound to two or more atoms of the chelating agent by whatever means (e.g., coordinate binding or complexation) occurs when a radioisotope and chelate group complex within each other in compounds according to the present invention. It is noted here that when a chelator is complexed to a radioisotope as used herein, the chelate complex structure is represented in a generic, nonlimiting sense, such that bonds which are represented may occur between a radioistope and the chelating agent, as well as additional bonds (such as between carbonyl/carboxyl groups) which are not specifically represented, but which are understood/determined to be bonded within the context of the chelate complex (to accommodate that different radioisotopes may bind differently to different chelate groups).

The term "DOTA" is used as an abbreviation for 1,4,7,10-tetraazacyclododecane-1,4,7,10-tetraacetic acid, a preferred chelator for use in the present invention, which chemical structure (bonded in compounds according to the present invention) is represented as follows:

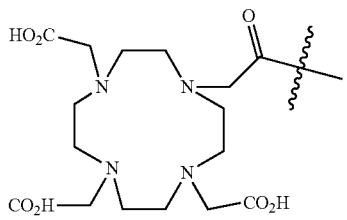

Complexed with radioisotopes according to the present invention, DOTA has the general (note that this general structure also includes the possibility of carbonyl/carboxyl groups also contributing to the complex depending on the radioisotope and is non-limiting) structure:

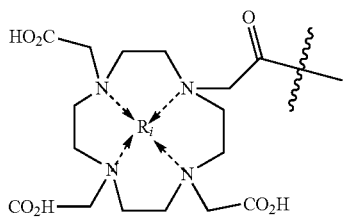

Where Ri is a radioisotope as otherwise disclosed herein.

The term "cyclic peptide", "Cycpeptide". "cyclic MSH peptide", or "CycMSH" refers to cyclic peptides which are bound optionally through a peptide linker (comprising 1, 2 or 3 amino acid residues) to DOTA according to the present invention. Cyclic peptides according to the present invention may be represented by the chemical structure

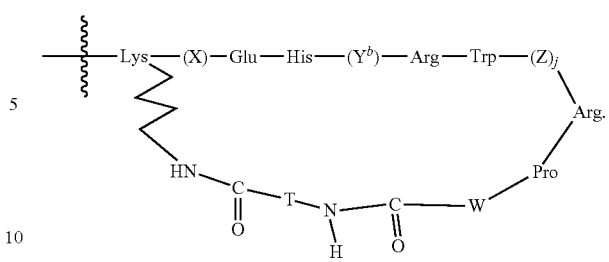

Where X norleucine, leucine or isoleucine, preferably norleucine;
$Y^b$ is D-phenylalanine or L-phenylalanine, preferably D-phenylalanine;
Z is Glycine or alanine, preferably glycine;
W is valine, leucine or isoleucine, preferably valine;
T is aspartic acid or glutamic acid, preferably aspartic acid or a

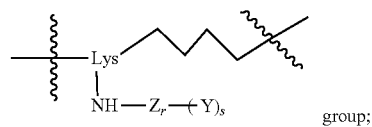

group;

Wherein each Z is independently an amino acid residue or an amino acid linker according to the chemical structure:

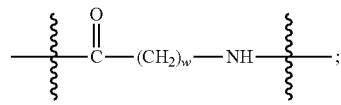

Y is a chelate group as otherwise described herein;
p is an integer from 0 to 20, preferably 1 to 12, preferably 2 to 8;
r is an integer from 0 to 250, preferably 0 to 5, preferably 0 to 1;
s is 1;
w is an integer from 0 to 20, preferably 1 to 12, preferably 2 to 8;
or a pharmaceutically acceptable salt thereof.

In preferred aspects of the present invention, X is norleucine, $Y^b$ is D-phenylalanine, Z is glycine, W is valine and T is aspartic acid, and is represented by the following chemical structure:

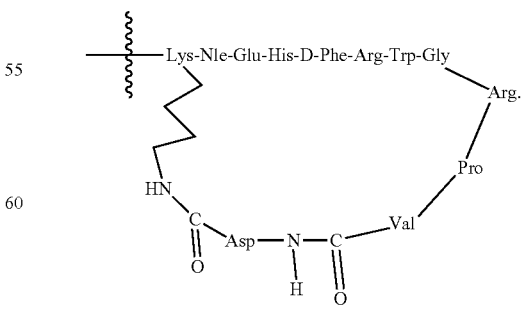

Alternatively, preferred cyclic peptides are represented by the following chemical structure:

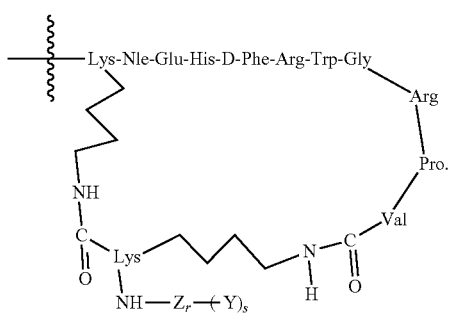

Wherein each Z is independently an amino acid residue or an amino acid linker according to the chemical structure:

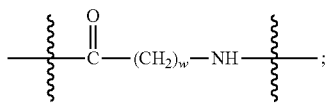

Y is a chelate group as otherwise described herein;
w is an integer from 0 to 20, preferably 1 to 12, preferably 2 to 8;
r is an integer from 0 to 250, preferably 0 to 5, preferably 0 to I;
s is 1; or
a pharmaceutically acceptable salt thereof.

The term "radical" is used to describe a group which is covalently bonded to another group in compounds according to the present invention.

The term "acylated" is used to describe an acyl group which may be used, where appropriate, at a terminal amine group of compounds of the present invention. The term "acyl" is used throughout the specification to describe a group at a terminal amine position of an amino acid which contains a $C_0$ to $C_{20}$ (preferably a $C_0$ to $C_{20}$) linear, branched or cyclic alkyl chain. The acyl group at a terminal amine position, results in an amide linkage, which, after administration, may be cleaved. Acyl groups according to the present invention are represented by the structure:

where $R_4$ is a $C_0$ to $C_{20}$ (preferably, a $C_1$ to $C_{20}$) linear, branched or cyclic alkyl group, phenoxymethyl, aryl, alkoxy, alkoxyalkyl, aryloxyalkyl, alkoxycarbonyloxy groups (e.g., Risopropoxycarbonypoxyl-methoxy), aryloxyalkyl, among others, all of which groups may be optionally substituted. Preferred acyl groups are those where $R_4$ is a $C_1$ to $C_{10}$ alkyl group. Acyl groups according to the present invention also include, for example, those acyl groups derived from benzoic acid and related acids, 3-chlorobenzoic acid, succinic, capric and caproic, lauric, myristic, palmitic, stearic and oleic groups, among numerous others. One of ordinary skill in the art will recognize the acyl groups which will have utility in the present invention, either to synthesize the target pharmaceutical compounds or as prodrug forms of the nucleosides according to the present invention.

The term "melanoma" is used to describe a malignant tumor of melanocytes which are found predominantly in skin but also in the bowel and the eye (see uveal melanoma), even though melanoma can be found in any part of the body. Melanoma is a form of cancer that begins in melanocytes, the cells that make skin pigment, or melanin. It may begin in a mole (skin melanoma), but can also begin in other pigmented tissues. There are several types of melanoma, defined by where they first appear, including skin and eye melanoma and in rare instances in the GI tract or lymph nodes Melanoma is one of the rarer types of skin cancer but causes the majority of skin cancer related deaths. Malignant melanoma is a serious type of skin cancer. It is due to uncontrolled growth of pigment cells, called melanocytes. Despite many years of intensive laboratory and clinical research, the sole effective cure is surgical resection of the primary tumor before it achieves a Breslow thickness greater than 1 mm.

Around 160,000 new cases of melanoma are diagnosed worldwide each year. About 48,000 melanoma related deaths occur worldwide per year. Malignant melanoma accounts for 75 percent of all deaths associated with skin cancer. The treatment includes surgical removal of the tumor; adjuvant treatment; chemo- and immunotherapy, or radiation therapy. The severity of melanoma is often characterized by the Clark level, which are for thin tumors and describe how deeply the cancer has spread into the skin, and the Breslow depth, which refers to the microscopic depth of tumor invasion.

The following stages are identified in the progression of the melanoma disease state. Melanoma progresses from an early stage (in situ) through an invasive stage, a high risk melanoma stage, a regional metastatic stage and a distant metastatic stage with varying degrees of survivability, as set forth below.

Melanoma Stages:
Stage 0: Melanoma in Situ (Clark Level I), 99.9% Survival
Stage I/II: Invasive Melanoma, 85-95% Survival
   T1a: Less than 1.00 mm primary, w/o Ulceration, Clark Level II-III
   T1b: Less than 1.00 mm primary, w/Ulceration or Clark Level IV-V
   T2a: 1.00-2.00 mm primary, w/o Ulceration
Stage II: High Risk Melanoma, 40-85% Survival
   T2b: 1.00-2.00 mm primary, w/Ulceration
   T3a: 2.00-4.00 mm primary, w/o Ulceration
   T3b: 2.00-4.00 mm primary, w/Ulceration
   T4a: 4.00 mm or greater primary w/o Ulceration
   T4b: 4.00 mm or greater primary w/Ulceration
Stage III: Regional Metastasis, 25-60% Survival
   N1: Single Positive Lymph Node
   N2: 2-3 Positive Lymph Nodes OR Regional Skin/In-Transit Metastasis
   N3: 4 Positive Lymph Nodes OR Lymph Node and Regional Skin/In Transit Metastases
Stage IV: Distant Metastasis, 9-15% Survival
   M1a: Distant Skin Metastasis, Normal LDH
   M1b: Lung Metastasis, Normal LDH
   M1c: Other Distant Metastasis OR Any Distant Metastasis with Elevated LDH
Based Upon AJCC 5-Year Survival with Proper Treatment Tradition therapy of melanoma involves a number of treatment options. These generally include surgery, chemotherapy, radiation therapy and immunotherapy (IL-2, other). In the case of surgery, treatment can vary and can include local excision, wide local excision, lymphadenectomy, sentinel lymph node biopsy and skin grafting. In the case of chemotherapy, a standard chemotherapeutic agent dacarbazine (DTIC) is administered to the patient in order to treat the cancer, generally through cancer cell death. In the case of radiation therapy, radiation is used as a palliative rather than a cure for melanoma. Radiation relieves bone pain and other symptoms caused by metastases to the bones, brain, and organs such as the liver. Although not curative, radiation treatment is being investigated for more widespread use in controlling other symptoms of skin cancer. In the case of immunotherapy (biologic treatment), a patient's natural immune system is raised or other immune compositions (IL-2) are administered to the patient against the cancer.

"Metastatic melanoma" refers to a progressed form of melanoma wherein the original cancer has metastasized to another area of the skin (regional or distant) or to other non-skin tissue (e.g., lungs, liver, brain, lymph system). Metastatic melanoma describes when melanoma has spread into surrounding healthy tissue and through the bloodstream, or lymphatic system, to other parts of the body. If melanoma spreads to these other areas, the cancer cells in the new tumor are still melanoma cells but the disease is called metastatic melanoma.

Unlike early stages of melanoma, which can be treated successfully with early diagnosis, the prognosis for patients diagnosed with metastatic melanoma is poor, with survival rates of six to nine months. In the past 35 years, the FDA has only approved two types of therapies for metastatic melanoma interleukin 2 (IL-2) and DTIC. The methods of treatment for metastatic melanoma include radiation, immunotherapy, chemotherapy and palliative surgery. Currently, there are no approved therapies that significantly improve survival for patients with metastatic melanoma.

The term "imaging", "molecular imaging" or "radioimaging is used to describe methods that use the nuclear properties of matter in diagnosis and therapy, pursuant to the present invention. More specifically, the present invention relies on molecular imaging because it produces images that reflect biological processes that take place at the cellular and subcellular level.

Molecular imaging is a discipline that unites molecular biology and in vivo imaging. It enables the visualisation of the cellular function and the follow-up of the molecular process in living organisms without perturbing them. The multiple and numerous potentialities of this field are applicable to the diagnosis and treatment of diseases such as cancer, in the present invention, in particular, melanoma, including metastatic melanoma. This technique also contributes to improving the treatment of these disorders by optimizing the pre-clinical and clinical tests of new medication. This approach also has a major economic impact due to earlier and more precise diagnosis.

Molecular imaging differs from traditional imaging in that probes labeled biomarkers are used to help image particular targets or pathways. Biomarkers interact chemically with their surroundings and in turn alter the image according to molecular changes occurring within the area of interest. This process is markedly different from previous methods of imaging which primarily imaged differences in qualities such as density or water content. This ability to image fine molecular changes opens up an incredible number of exciting possibilities for medical application, including early detection and treatment of disease, in particular, melanoma and metastatic melanoma according to the present invention.

There are a number of different imaging modalities that can be used for noninvasive molecular imaging, using compounds according to the present invention. Each have different strengths and weaknesses and some are more adept at imaging multiple targets or sites than others. This is important in instances where metastatic melanoma is suspected. The modalities which can be used in the present invention are varied and in the present invention principally include single photon emission computed tomography (SPECT) and positron emission tomography (PET), discussed below.

The main purpose of SPECT when used in melanoma imaging pursuant to the present invention is to measure the distribution of radioisotope in skin tissue, in particular, those skin regions and other tissues where melanoma, including metastatic melanoma, is suspected. The development of computed tomography in the 1970s allowed mapping of the distribution of the radioisotopes in tissue, and led to the technique now called SPECT.

The imaging agent used in SPECT emits gamma rays, as opposed to the positron emitters used in PET. There are a number of radioisotopes (such as $^{99m}$Tc, $^{111}$In, $^{123}$I, $^{201}$Tl, $^{67}$Ga, $^{99m}$Tc and $^{203}$Pb, among other gamma ray emitters) that can be used in the present invention and imaged with SPECT technology. In SPECT, where possible, by rotating the gamma camera around the area to be analysed, a three dimensional image of the distribution of the radiotracer may be obtained by employing filtered back projection or other tomographic techniques. The radioisotopes used in SPECT have relatively long half lives (a few hours to a few days) making them easy to produce and relatively cheap in comparison to other radioisotopes. This represents the major advantage of SPECT as an imaging technique, since it is significantly cheaper than PET or other imaging methods such as magnetic resonance imaging (MRI). However, SPECT sometimes lacks exceptional spatial (i.e., where exactly the particle is) or temporal (i.e., did the contrast agent signal happen at a particular millisecond or not) resolution.

Another imaging technique which finds particular use in the present invention is positron emission tomography (PET). In PET, a molecule is tagged with a positron emitting isotope. These positrons (β particles) interact with nearby electrons, emitting two 511,000 eV photons, directed 180 degrees apart in opposite directions. These photons are then detected by the scanner which can estimate the density of positron annihilations in a specific area. When enough interactions and annihilations have occurred, the density of the original molecule may be measured in that area. Typical isotopes include $^{11}$C, $^{13}$N, $^{15}$O, $^{18}$F, $^{64}$Cu, $^{62}$Cu, $^{124}$I, $^{76}$Br, $^{82}$Rb and $^{68}$Ga, among others, including the preferred $^{66}$Ga, $^{68}$Ga, $^{64}$Cu, $^{86}$Y. One of the major disadvantages of PET is that most of the radioisotopes-must be made with a cyclotron, thus making the use of PET, in certain instances prohibitively expensive. Most of these probes also have a half life measured in minutes and hours, thus forcing the cyclotron, in many instances, to be on site. These factors can make PET sometimes prohibitively expensive, except in certain cases, which the present invention addresses in certain aspects. PET imaging does have many advantages though. First and foremost is its sensitivity: a typical PET scanner can detect between $10^{-11}$ mol/L to $10^{-12}$ mol/L concentrations.

The term "effective" is used, to describe an amount of a compound, component or composition, which produces an intended effect when used within the context of its use, which may be a diagnostic method, a therapeutic method, a method to monitor the progression of therapy or other method (chemical synthesis) pursuant to the present invention. In the case of therapeutic methods, an effective amount for treating melanoma, including metastatic melanoma, is that amount which shrinks cancerous tissue (e.g., tumor), produces a remission, prevents further growth of the tumor and/or reduces the likelihood that the cancer in its early stages (in situ or invasive) does not progress further to metastatic melanoma.

Noted here is that within the context of the use of the present invention, the patient will be receiving a radiation dose, which provides guidance to the amount of compound which is considered effective when used within the context of its use. A patient undergoing a nuclear medicine procedure will receive a radiation dose. Under present international guidelines it is assumed that any radiation dose, however small, presents a risk. The radiation doses delivered to a patient in a nuclear medicine investigation present a very small risk of side effects, including inducing cancer in the patient. In this respect it is similar to the risk from X-ray investigations except that the dose is delivered internally rather than from an external source such as an X-ray machine.

The radiation dose from a diagnostic nuclear medicine procedure is expressed as an effective dose with units of sieverts (usually given in millisieverts, mSv). The effective dose resulting from an investigation is influenced by the amount of radioactivity administered in megabecquerels (MBq), the physical properties of the radiopharmaceutical used, its distribution in the body and its rate of clearance from the body.

Effective doses can range from 6 µSv (0.006 mSv) for a 3 MBq chromium-51 EDTA measurement of glomerular filtration rate to 37 mSv or more for a 150 MBq thallium-201 non-specific tumour imaging procedure. The common bone scan with 600 MBq of technetium-99m-MDP has an effective dose of 3 mSv. Formerly, units of measurement were the Curie (Ci), being 3.7E10 Bq, and also 1.0 grams of radium (Ra-226); the rad (radiation absorbed dose), now replaced by the Gray; and the rem (röntgen equivalent man), now replaced with the Sievert. The rad and rem are essentially equivalent for almost all nuclear medicine procedures, and only alpha radiation will produce a higher Rem or Sv value, due to its much higher relative biological effectiveness (RBE).

The term "coadministration" or "combination therapy" is used to describe a therapy in which at least two active compounds (one of which is a compound according to the present invention) in effective amounts are used to treat melanoma, including metastatic melanoma as otherwise described herein at the same time. Although the term coadministration preferably includes the administration of two active compounds to the patient at the same time, it is not necessary that the compounds be administered-to-the-patient at the same time, although effective amounts of the individual compounds will be present in the patient at the same time. Compounds according to the present invention may be administered with one or more compound including a chemotherapeutic agent such as dacarbazine (DTIC) and/or and immunotherapeutic agent such as IL-2 and/or α-interferon, among other compounds.

The term "treating" or "successfully treating" when used in the context of treating melanoma, including metastatic melanoma, shall include shrinking a tumor, curing melanoma, including melanoma which has metastazied (by causing a remission of the cancer in the patient) or reducing the likelihood or preventing the spread of the melanoma into other organs. Melanoma, including metastatic melanoma, may be treated using compounds according to the present invention alone, or in combination with other methods and/or compounds including surgery, chemotherapy (especially the use of the chemotherapeutic agent dacarbazine or DTIC), radiation therapy (i.e., with agents other than the present therapeutic compositions) and immunotherapy (IL-2 and/or α-interferon).

In certain aspects of the invention, where the basic compound and in particular, the DOTA group, as described above, is complexed with a radioisotope for purposes of being used in the diagnosis or therapy of melanoma, including metastatic melanoma, the invention relates to compounds and their pharmaceutically acceptable salts according to the general chemical structure (note that the radioisotope may be complexed to one or more carbonyl/carboxyl groups of the DOTA moiety as well):

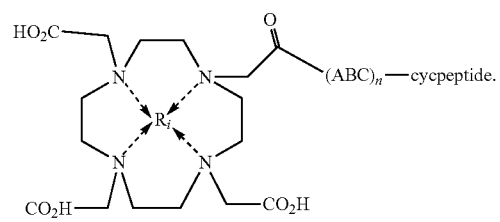

Where A, B, C, n and cycpeptide are as otherwise described hereinabove and cycpeptide; and the radioisotope ($R_i$) is selected from the group consisting of $^{68}Y$, $^{90}Y$, $^{111}In$, $^{177}Lu$, $^{225}Ac$, $^{212}Bi$, $^{213}Bi$, $^{66}Ga$, $^{67}Ga$, $^{68}Ga$, $^{64}Cu$, $^{67}Cu$, $^{71}As$, $^{72}As$, $^{76}As$, $^{77}As$, $^{65}Zn$, $^{48}V$, $^{203}Pb$, $^{209}Pb$, $^{212}Pb$, $^{166}Ho$, $^{149}Pm$, $^{153}Sm$, $^{201}Tl$, $^{188}Re$, $^{186}Re$ and $^{99m}Tc$.

Preferred compounds according to the present invention relate to compounds according to the structure (note that the radioisotope may be complexed to one or more carbonyl/carboxyl groups of the DOTA moiety as well):

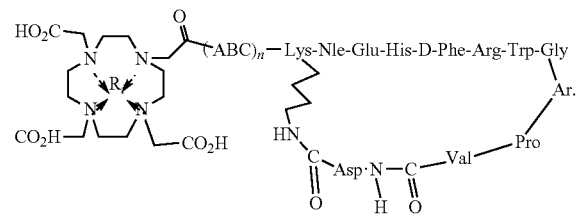

Where A, B, C, n and $R_i$ are the same as described above.

Additional preferred compounds according to the present invention may be represented by the following structure (note that the radioisotope may be complexed to one or more carbonyl/carboxyl groups of the DOTA moiety as well):

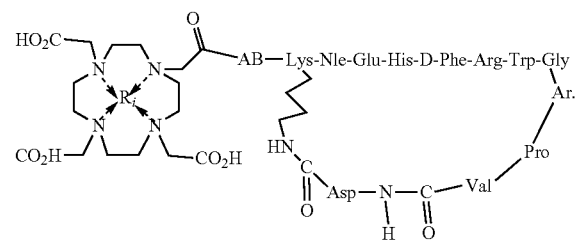

Where Ri is the same as described above and AB is a diamino acid linker, which is preferably selected from the group consisting of GlyGlu, GlyAsp, GluGlu, GluAsp, AspGlu and AspAsp.

Alternative preferred compounds according to the present invention are represented by the chemical structure (note that the radioisotope may be complexed to one or more carbonyl/carboxyl groups of the DOTA moiety as well):

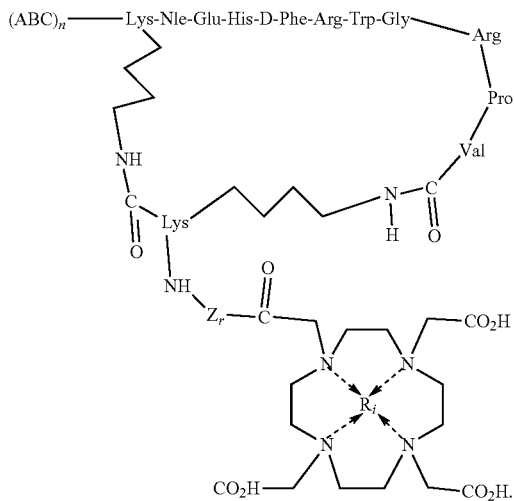

Wherein A, B, C (including an N-terminal amine of A and B, where appropriate, may be preferably acylated), n, $R_i$, Z and r are the same as otherwise described above.

In preferred aspects, $R_i$ is selected from the group consisting of $^{111}$In, $^{86}$Y, $^{66}$Ga, $^{67}$Ga, $^{68}$Ga, $^{203}$Pb, $^{64}$Cu and $^{99m}$Tc when the compounds are to be used diagnostically or to monitor therapeutic intervention and R, is selected from the group consisting of $^{90}$Y, $^{177}$Lu, $^{186}$Re, $^{188}$Re, $^{212}$Bi/$^{212}$Pb, $^{213}$Bi, $^{149}$Pm, $^{166}$Ho and $^{153}$Sm when compounds according to the present invention are used in radiation therapy to treat melanoma, including metastatic melanoma. In other preferred aspects, (ABC) is a diamino acid linker group AB wherein AB is selected from the group consisting of GlyGlu, GlyAsp, GluGlu, GluAsp, AspGlu and AspAsp, preferably GlyGlu.

The present invention also relates to pharmaceutical compositions comprising an effective amount of a compound for diagnostic and/or therapeutic purposes in combination with a pharmaceutically acceptable carrier, additive or excipient in pharmaceutical dosage form. For diagnostic purposes pharmaceutical compositions are formulated generally in parenteral dosage form, especially for intravenous administration, although oral or topical formulations may be useful in certain instances. In the case of the use of compounds according to the present invention for therapeutic purposes, the compositions are formulated preferably in parenteral or topical dosage forms, although orally administered dosage forms are also useful.

The compounds of the present invention, may, in accordance with the invention, be administered in single or divided doses by the oral, parenteral or topical routes. Administration of the active compound may range from a single intravenous injection to continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present invention as sprays, mists, or aerosols for intra-nasal, intra-tracheal or pulmonary administration may also be used. The present invention therefore also is directed to pharmaceutical compositions comprising an effective amount of compound according to the present invention, optionally in combination with a pharmaceutically acceptable carrier, additive or excipient.

The amount of compound used is that amount effective within the context of the administration, whether that administration is for diagnostic purposes or therapeutic purposes. A suitable oral dosage for a compound according to the present invention would be in the range of about 0.01 mg to 10 g or more per day, preferably about 0.1 mg to about 1 g per day. In parenteral formulations, a suitable dosage unit may contain from 0.1 to 250 mg of said compounds, which may be administered from one to four times per day (for diagnostic purpose, preferably once in a bolus dose), whereas for topical administration, formulations containing 0.01 to 1% active ingredient are preferred. It should be understood, however, that the dosage administration from patient to patient will vary and the dosage for any particular patient will depend upon the clinician's judgment, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier, additive or excipient material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like.

The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound according to the present invention can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds. In certain preferred diagnostic and/or therapeutic embodiments, compounds according to the present invention are administered intravenously in sterile saline solution.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Preservatives added may include benzalkonium chloride, chloro-butanol or phenylethyl alcohol, among numerous others.

Additionally, the compounds provided by the invention can be administered by suppository.

In certain aspects according to the present invention, where various cancers are to be treated, the compounds may be co-administered with at least one other anti-cancer agent such as dacarbazine (DTIC) or an immunotherapeutic agent such as IL-2 and/or α-interferon. In addition, compounds according to the present invention may be administered prior to, during or after surgery to remove melanoma tissue.

Preparation of compounds according to the present invention proceeds using standard synthetic chemical techniques which are readily available in the art. Synthetic methods for obtaining compounds related to the present invention may be found in the examples section of the present specification. These methods can serve as guides for obtaining compounds according to the present invention. In general, the present compounds may be made by condensing an activated DOTA or other chelating group (containing a leaving group or using a coupling agent to facilitate the binding of the carboxyl group on DOTA or other chelating group to the amine terminal group of the amino acid linker (including, in certain cases, the lysine side chain amine group) or, in the case where the linker is absent directly to the amine group). The radionuclide may be complexed to the chelate (DOTA) group either before or after the activated chelate (DOTA) group is condensed onto the linker-Cyclic peptide or the Cyclic peptide (linker not present). The linker-cyclic peptide and/or the cyclic peptide with no linker is synthesized using conventional peptide synthesis (as otherwise described in the examples section or using methods readily available in the art using protecting group chemistry) and the lactam coupling between the lysine amino acid and the amino acid (aspartic acid or glutamic acid) at the carboxylic acid end of the precyclized oligopeptide is readily performed using methods described herein or as otherwise as readily known in the art.

Once the compounds are synthesized, they may be formulated in pharmaceutical dosage form using convention pharmaceutical formulation methods readily available in the art by simply admixing compounds with chosen carriers, additives and/or excipients, depending upon the dosage form to be used and depending upon the use (diagnostic or therapeutic) of the compositions.

The following examples are provided to assist in describing the present invention. The details of these examples and the general description of the examples are for description purposes only and should be seen or taken to limit the scope of the invention in any way.

EXAMPLES

First Set of Examples—Directed to Synthesis and Applicability of Compounds According to the Present Invention[1]

[1] Note that the first set of references presented in the reference section applies to this set of experiments/examples.

The strategy of peptide cyclization was used to improve binding affinity, in vivo stability and receptor selectivity of the α-MSH peptides (14-16). Compared to the linear peptides, the cyclic peptides possess less conformational freedom due to the stabilization of secondary structures such as beta turns, which results in greater receptor binding affinities. Furthermore, the constrained cyclic peptides confer higher stability against the proteolytic degradations in vivo (17). Peptide cyclization strategies can be generally classified into four types, namely, 1) backbone to backbone; 2) N-terminus to C-terminus; 3) one side chain to C-terminus or N-terminus; 4) two side chains via disulfide or lactam bridges. Over the past several years, peptide cyclization through metal coordination has been successfully employed in developing radiolabeled cyclic α-MSH peptide analogues for melanoma imaging and therapy. Metal cyclization made the α-MSH peptide analogues resistant to chemical and proteolytic degradation in vivo (18, 19). $^{111}$In-DOTA-Re[Cys$^{3,4,10}$, D-Phe$^{7}$]-α-MSH$_{3-13}$}($^{111}$In-DOTA-ReCCMSH) exhibited 11.4±2.89% injected dose/gram (% ID/g) tumor uptake 2 h post-injection in B16/F1 murine melanoma mouse model (19). A comparison of biodistribution data between $^{111}$In-labeled DOTA-conjugated metal-cyclized and disulfide bridge-cyclized α-MSH peptide analogues demonstrated that the metal cyclization resulted in more favorable pharmacokinetics of radiolabeled peptides, such as higher tumor uptake and lower renal uptake values (19), indicating that the different cyclization strategies might dramatically affect the biodistribution properties of peptides with comparable in vitro binding affinities.

In these examples, Lys-Asp lactam bridge cyclization was employed to the α-MSH peptides to examine its effect on melanoma targeting and pharmacokinetics of the radiolabeled peptides. Two novel DOTA-conjugated lactam bridge-cyclized α-MSH peptide analogues, namely DOTA-CycMSH and DOTA-GlyGlu-CycMSH, were synthesized and characterized by liquid chromatography-mass spectrometry (LC-MS). A negatively-charged linker of -Gly-Glu- was introduced between DOTA and CycMSH sequences to determine its effect in reducing the renal uptake value of the radiolabeled peptide. The pharmacokinetics and SPECT/CT imaging of $^{111}$In-labeled lactam bridge-cyclized α-MSH peptides were determined in B16/F1 melanoma-bearing C57 mice to evaluate their potential as SPECT imaging probes for melanoma detection.

Figure 2:
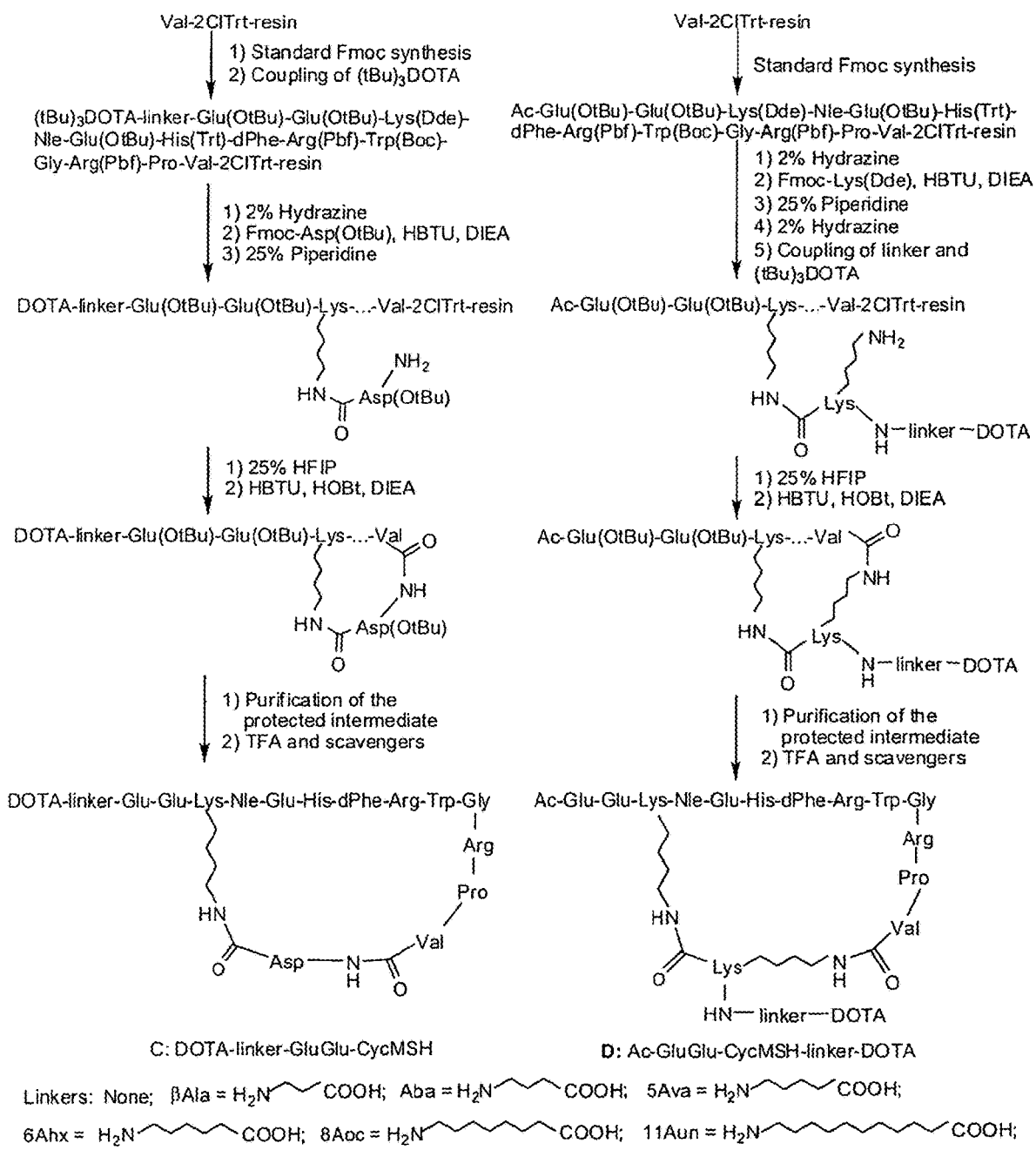
FIG. 2 shows a general synthesis scheme for compounds which are set forth in FIG. 1, which may be adapted and modified generically to compounds according to the present invention.

General synthetic methods follow the general approach which is presented in attached FIG. 2. These methods may be readily modified or practiced by analogy within the routineer's ordinary skill to provide modified compounds according to the present invention.

Experimental Procedures

Chemicals and Reagents: Amino acid and resin were purchased from Advanced ChemTech Inc. (Louisville, Ky.) and Novabiochem (San Diego, Calif.). DOTA-tri-t-butyl ester was purchased from Macrocyclics Inc. (Richardson, Tex.). $^{111}$InCl$_3$ was purchased from Mallinckrodt, Inc. (St. Louis, Mo.). All other chemicals used in this study were purchased from Thermo Fischer Scientific (Waltham, Mass.)

and used without further purification. B16/F1 murine melanoma cells were obtained from American Type Culture Collection (Manassas, Va.).

Peptide Synthesis: Intermediate scaffold of $H_2N$-Lys(Dde)-Nle-Glu(OtBu)-His(Trt)-D-Phe-Arg(Pbf)-Trp(Boc)-Gly-Arg(Pbf)-Pro-Val was synthesized on Val-2-Chlorotrityl Chloride (Val-2ClTrt) resin using standard 9-fluorenylmethyloxycarbonyl (Fmoc) chemistry by an Advanced ChemTech multiple-peptide synthesizer (Louisville, Ky.). A small aliquot of the scaffold material was cleaved and characterized by LC-MS. Gly-Glu(OtBu) and DOTA-tri-t-butyl ester were manually attached to the intermediate scaffold using standard Fmoc chemistry, respectively. Protected branched peptide was cleaved from the resin treating with 25% hexafluoroisopropanol (HFIP) and 5% triisopropylsilane (TIS) in dichloromethane (DCM) and characterized by LC-MS. Peptide cyclization between the acid moiety of Val and the amino group of Asp coupled to the Lys side chain was achieved by overnight reaction in DMF in presence of 1 mM 1-hydroxybenzotriazole (HOBT), 2-(1H-benzotriazole-1-yl)-1,1,3,3-tetranethyluronium hexafluorophosphate (HBTU) and N,N-diisopropylethylamine (DIEA) mixture. The protecting groups were totally removed by treating with a mixture of trifluoroacetic acid (TFA), thioanisole, phenol, water, ethanedithiol and triisopropylsilane (87.5:2.5:2.5:2.5:2.5:2.5) for 2 h at room temperature (25° C.). The peptides were precipitated and washed with ice-cold ether for four times. The final products were purified by RP-HPLC and characterized by LC-MS.

In vitro Competitive Binding Assay: The $IC_{50}$ values of DOTA-CycMSH and DOTA-GlyGlu-CycMSH were determined by using methods described previously (8). B16/F1 cells were harvested and seeded into a 24-well cell culture plate ($5\times10^5$/well) and incubated at 37° C. overnight. After being washed once with binding media (MEM with 25 mM HEPES, pH 7.4, 0.2% BSA, 0.3 mM 1,10-phenathroline), the cells were incubated at room temperature (25° C.) for 2 h with approximately 50,000 cpm of $^{125}$I-Tyr$^2$-[Nle$^4$, D-Phe$^7$]-α-MSH {NDP-MSH} (GE HealthCare, Piscataway, N.J.) in presence of increasing concentrations of DOTA-CycMSH or DOTA-GlyGlu-CycMSH in 0.3 ml of binding media. The reaction media were aspirated after incubation. Cells were rinsed with 0.5 ml of ice-cold pH 7.4, 0.2% BSA/0.01 M PBS twice and lysed in 0.5 ml of 1 N NaOH for 5 minutes. The activities in cells were measured in a gamma counter. The $IC_{50}$ values for the peptides were calculated by using the Grafit software (Erithacus Software Limited, UK).

Complexation of the Peptide with $^{111}$In: $^{111}$In-DOTA-CycMSH and $^{111}$In-DOTA-GlyGlu-CycMSH were prepared using a 0.5 M NH$_4$OAc-buffered solution at pH 5.4. Briefly, 50 μl of $^{111}$InCl$_3$ (18.5-37.0 MBq in 0.05 M HCl), 10 μl of 1 mg/ml DOTA-CycMSH or DOTA-GlyGlu-CycMSH aqueous solution and 400 μl of 0.5 M NH$_4$OAc (pH 5.4) were added into a reaction vial and incubated at 75° C. for 45 min. After the incubation, 20 μl of 0.5% EDTA aqueous solution was added into the reaction vial to scavenge potential unbound $^{111}$In. The radiolabeled complexes were purified to single species by Waters RP-HPLC (Milford, Mass.) on a Grace Vadyc C-18 reverse phase analytical column (Deerfield, Ill.) using a 20-minute gradient of 16-26% acetonitrile in 20 mM HCl aqueous solution with a flowrate of 1 ml/min. Purified peptide samples were purged with $N_2$ gas for 20 minutes to remove the acetonitrile. The pH of final solution was adjusted to 7.4 with 0.1 N NaOH and normal saline for animal studies. The stability of $^{111}$In-DOTA-CycMSH and $^{111}$In-DOTA-GlyGlu-CycMSH was determined by incubation in mouse serum at 37° C. according to the published procedure (20) for various time periods, and monitored for degradation by RP-HPLC.

Cellular Internalization and Efflux of $^{111}$In-labeled Peptides: Cellular internalization and efflux of $^{111}$In-DOTA-CycMSH and $^{111}$In-DOTA-GlyGlu-CycMSH were evaluated in B16/F1 cells as described by Miao et al (21). After being washed once with binding media (MEM with 25 mM HEPES, pH 7.4, 0.2% BSA, 0.3 mM 1,10-phenathroline), B16/F1 cells in cell culture plates were incubated at 25° C. for 20, 40, 60, 90 and 120 min (n=4) in presence of approximately 200,000 counts per minute (cpm) of HPLC purified $^{111}$In-DOTA-CycMSH (0.019 pmol) or $^{111}$In-DOTA-GlyGlu-CycMSH (0.019 pmol). After incubation, the reaction media were aspirated and cells were rinsed with 2×0.5 ml of ice-cold pH 7.4, 0.2% BSA/0.01 M PBS. Cellular internalization of radiolabeled peptides was assessed by washing the cells with acidic buffer [40 mM sodium acetate (pH 4.5) containing 0.9% NaCl and 0.2% BSA] to remove the membrane-bound radioactivity. The remaining internalized radioactivity was obtained by lysing the cells with 0.5 ml of 1N NaOH for 5 min. Membrane-bound and internalized $^{111}$In activities were counted in a gamma counter. Cellular efflux of radiolabeled peptides was determined by incubating B16/F1 cells with $^{111}$In-DOTA-CycMSH and $^{111}$In-DOTA-GlyGlu-CycMSH for 2 h at 25° C., removing non-specific-bound activity with 2×0.5 ml of ice-cold pH 7.4, 0.2% BSA/0.01 M PBS rinse, and monitoring radioactivity released into cell culture media. At time points of 20, 40, 60, 90 and 120 min, the radioactivities in media, on cell surface and in cells were separately collected and counted in a gamma counter.

Biodistribution Studies: All the animal studies were conducted in compliance with Institutional Animal Care and Use Committee approval. The pharmacokinetics of $^{111}$In-DOTA-CycMSH and $^{111}$In-DOTA-GlyGlu-CycMSH were determined in B16/F1 murine melanoma-bearing C57 female mice (Harlan, Indianapolis, Ind.). C57 mice were inoculated subcutaneously with $1\times10^6$ B16/F1 murine melanoma cells in the right flank. After 10 days, when the weight of tumors reached approximately 0.2 g, 0.037 MBq of $^{111}$In-DOTA-CycMSH or $^{111}$In-DOTA-GlyGlu-CycMSH was injected into each mouse through the tail vein. Groups of 5 mice were sacrificed at 2, 4 and 24 h post-injection, and tumors and organs of interest were harvested, weighed and counted. Blood values were taken as 6.5% of the whole-body weight. The tumor uptake specificity of $^{111}$In-DOTA-CycMSH and $^{111}$In-DOTA-GlyGlu-CycMSH was determined by blocking tumor uptake with the co-injection of 10 μg (6.07 nmol) of unlabeled NDP-MSH, a linear α-MSH peptide analogue with picomolar affinity for the MC1 receptors present on murine melanoma cells. Statistical analysis was performed using the Student's t-test for unpaired data. A 95% confidence level was chosen to determine the significance between radiolabeled compounds, with p<0.05 being significantly different.

Imaging Melanoma with $^{111}$In-DOTA-CycMSH and $^{111}$In-DOTA-GlyGlu-CycMSH: Two B16/F1 melanoma-bearing C57 mice were injected with 13.7 MBq of $^{111}$In-DOTA-CycMSH or $^{111}$In-DOTA-GlyGlu-CycMSH via the tail vein, respectively. The mice were euthanized for micro-CT imaging immediately followed by micro-SPECT imaging at 2 h post-injection. Micro-SPECT scans of 60 frames for each animal were acquired and total counts acquisitions of 524,672 and 278,242 counts (2 h acquisition) were achieved for both SPECT scans, respectively. The micro-SPECT images were obtained using the Micro-CAT II CT/SPECT (Siemens) unit equipped with high resolution 2 mm pinhole collimators (22). Reconstructed data from SPECT and CT were visualized and co-registered using Amira 3.1 (Ascent Media System & Technology Service, Northvale, N.J.).

Urinary Metabolites of $^{111}$In-DOTA-CycMSH and $^{111}$In-DOTA-GlyGlu-CycMSH: One hundred microliter of HPLC purified $^{111}$In-DOTA-CycMSH (0.74-1.11 MBq, 0.82-1.12 ng) or $^{111}$In-DOTA-GlyGlu-CycMSH (0.74-1.11 MBq, 0.90-1.35 ng) was injected into each B16/F1 murine melanoma-bearing C57 mouse through the tail vein. At 2 h after dose administration, mice were sacrificed and the urine was collected. The radioactive metabolites in the urine were analyzed by injecting aliquots of urine into HPLC. A 20-minute gradient of 16-26% acetonitrile/20 mM HCl was used for the urine analysis.

Results

Figure 3:
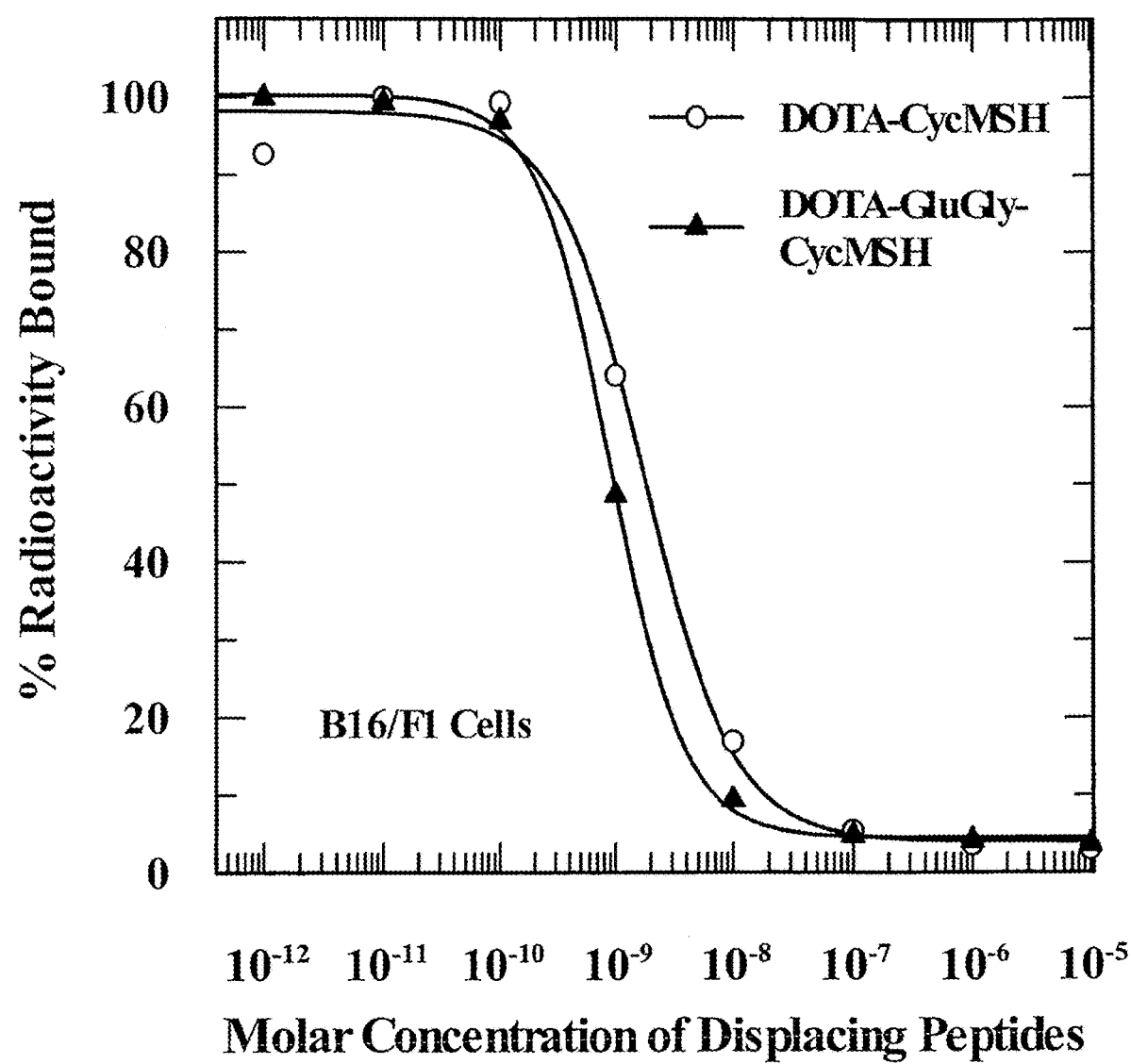
FIG. 3 shows the competitive binding curves of DOTA-CycMSH and DOTA-GlyGlu-CycMSH in B16/F1 murine melanoma cells. The IC$_{50}$ values of DOTA-CycMSH and DOTA-GlyGlu-CycMSH were 1.75 nM and 0.90 nM.
Figure 4:
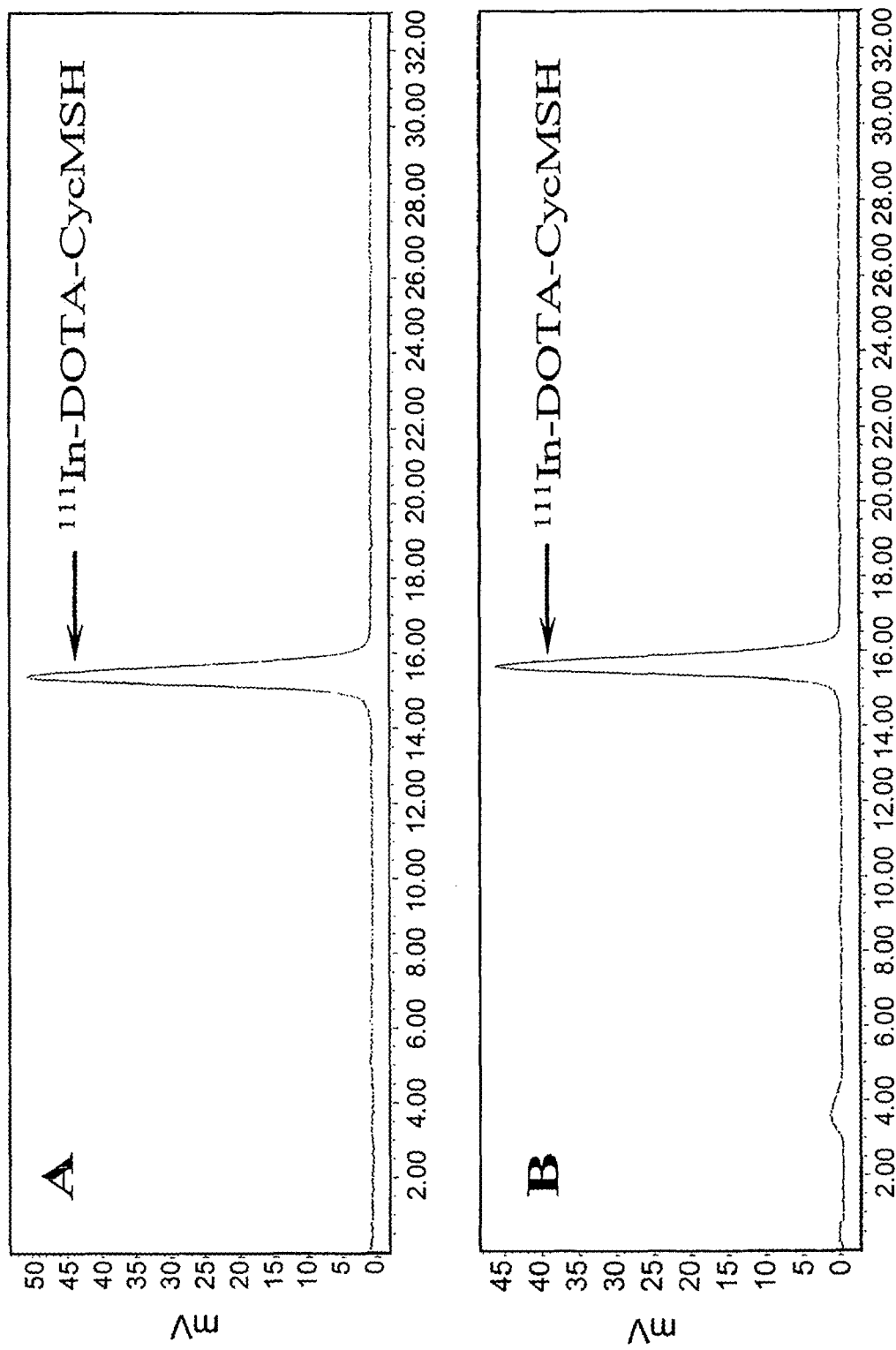
FIG. 4 shows the HPLC profiles of radioactive $^{111}$In-DOTA-CycMSH (A), $^{111}$In-DOTA-GlyGlu-CycMSH (C) and mouse serum stability of $^{111}$In-DOTA-CycMSH (B), CycMSH (D) after 24 h incubation at 37° C., respectively. The retention times of $^{111}$In-DOTA-CycMSH and $^{111}$In-DOTA-GlyGlu-CycMSH were 15.4 and 18.0 min, respectively.

DOTA-CycMSH and DOTA-GlyGlu-CycMSH were synthesized, purified by RP-HPLC and the identities of peptides were confirmed by electrospray ionization mass spectrometry. The synthetic schemes are presented in attached FIG. 2. The competitive binding curves of DOTA-CycMSH and DOTA-GlyGlu-CycMSH are shown in attached FIG. 3. The $IC_{50}$ values of DOTA-CycMSH and DOTA-GlyGlu-CycMSH were 1.75 nM and 0.90 nM in B16/F1 cells. The peptides were labeled with $^{111}$In using a 0.5 M $NH_4OAc$-buffered solution at pH 5.4. The radiolabeling yields were greater than 95% for both peptides. $^{111}$In-DOTA-CycMSH and $^{111}$In-DOTA-GlyGlu-CycMSH were completely separated from their excess non-labeled peptides by RP-HPLC. The retention times of $^{111}$In-DOTA-CycMSH and $^{111}$In-DOTA-GlyGlu-CycMSH were 15.4 and 18.0 min, respectively. The specific activities of $^{111}$In-DOTA-CycMSH and $^{111}$In-DOTA-GlyGlu-CycMSH were $9.03\times10^8$ and $8.23\times10^8$ MBq/g, respectively. $^{111}$In-DOTA-CycMSH and $^{111}$In-DOTA-GlyGlu-CycMSH were stable in mouse serum at 37° C. Only the $^{111}$In-labeled peptides were detected by RP-HPLC after 24 h of incubation (FIG. 4).

Figure 6:
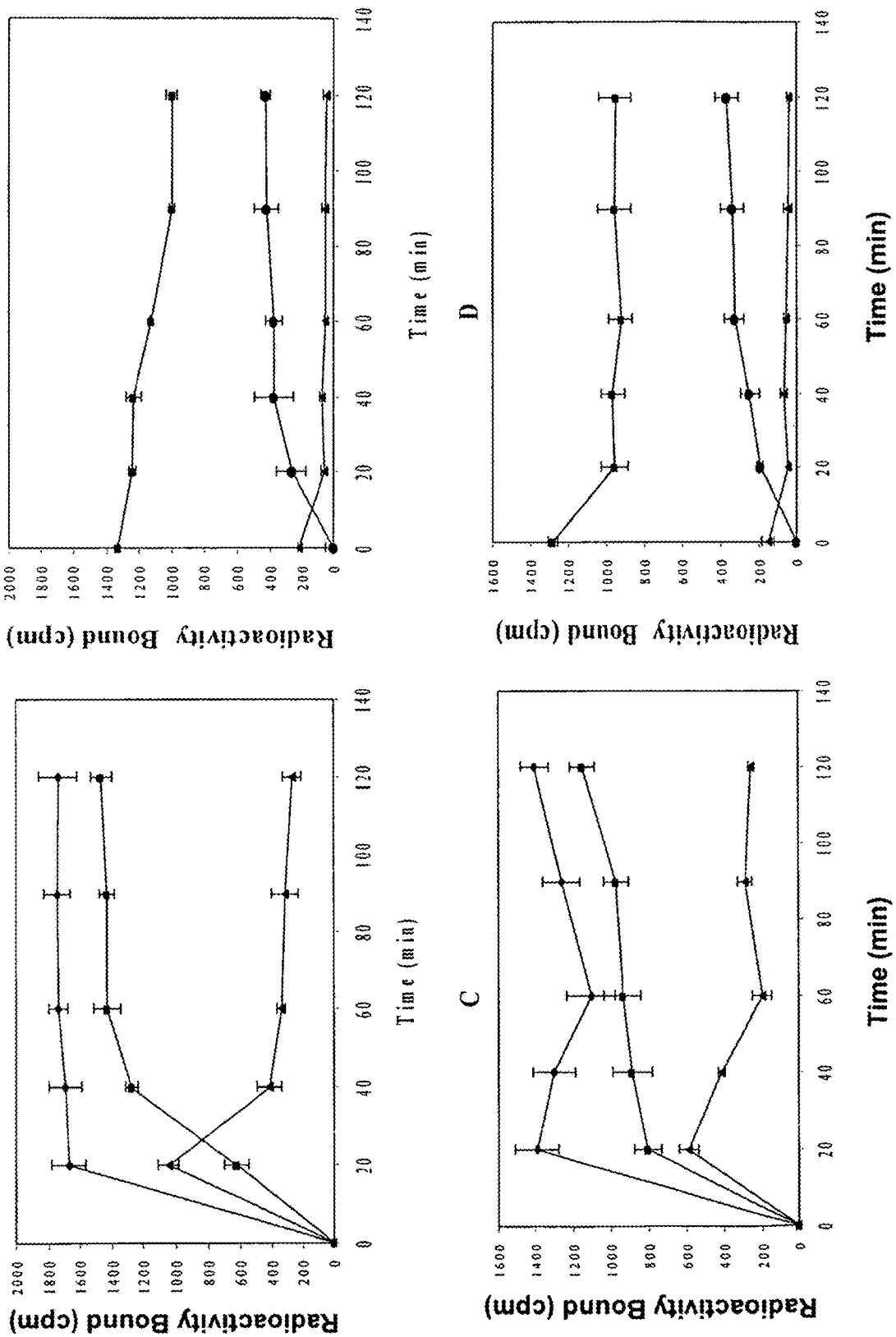
FIG. 6 shows the cellular internalization and efflux of $^{111}$In-DOTA-CycMSH (A and B) and In-DOTA-GlyGlu-CycMSH (C and D) in B16/F1 murine melanoma cells at 25° C. Total bound radioactivity (♦), internalized activity (■), cell membrane activity (▲) and cell culture media activity (•) were presented as counts per minute (cpm).

Cellular internalization and efflux of $^{111}$In-DOTA-CycMSH and $^{111}$In-DOTA-GlyGlu-CycMSH were evaluated in B16/F1 cells at 25° C. FIG. 6 illustrates cellular internalization and efflux of $^{111}$In-DOTA-CycMSH and $^{111}$In-DOTA-GlyGlu-CycMSH. Both $^{111}$In-DOTA-CycMSH and $^{111}$In-DOTA-GlyGlu-CycMSH exhibited rapid cellular internalization and extended cellular retention. There were 73.71±1.71% of the $^{111}$In-DOTA-CycMSH and 66.19±2.12% of the $^{111}$In-DOTA-GlyGlu-CycMSH activity internalized in the B16/F1 cells 40 min post incubation. There were 81.98±2.02% of the $^{111}$In-DOTA-CycMSH and 78.93±0.64% of the $^{111}$In-DOTA-GlyGlu-CycMSH activity internalized in the cells after 2 h incubation. Cellular efflux experiments demonstrated that 90.26±1.71% of the $^{111}$In-DOTA-CycMSH activity and 90.00±1.10% of the $^{111}$In-DOTA-GlyGlu-CycMSH activity remained inside the cells 2 h after incubating cells in culture media at 25° C.

Figure 5:
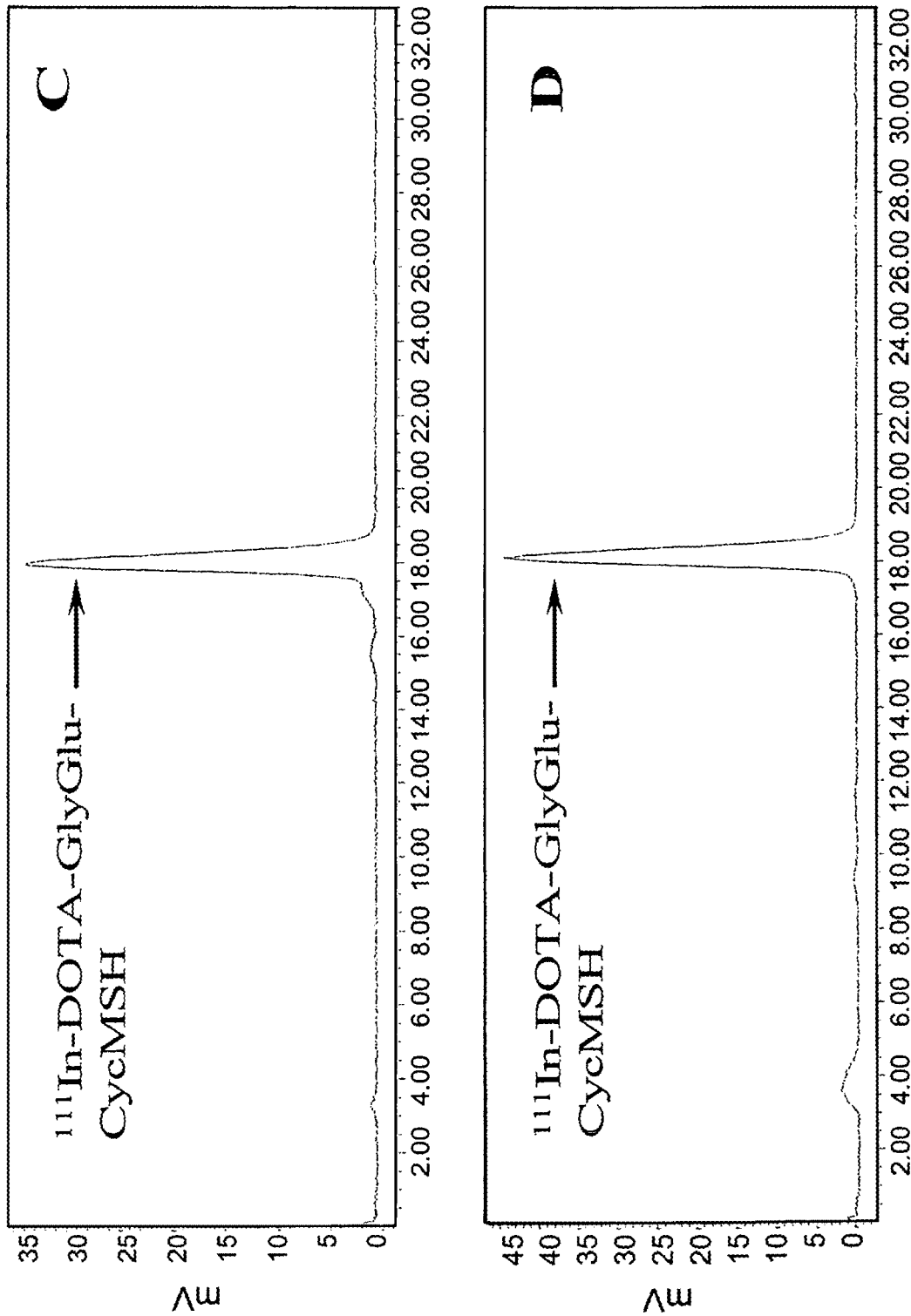
FIG. 5 shows a table 1 wherein the biodistribution of $^{111}$In-DOTA-CycMSH and $^{111}$In-DOTA-GlyGlu-CycMSH in B16/F1 murine melanoma-bearing C57 mice is presented. The data were presented as percent injected dose/gram or as percent injected dose (Mean±SD, n=5).

The pharmacokinetics and tumor targeting properties of $^{111}$In-DOTA-CycMSH and $^{111}$In-DOTA-GlyGlu-CycMSH were determined in B16/F1 murine melanoma-bearing C57 mice. The biodistribution of $^{111}$In-DOTA-CycMSH and $^{111}$In-DOTA-GlyGlu-CycMSH are shown in Table 1, FIG. 5. Both $^{111}$In-DOTA-CycMSH and $^{111}$In-DOTA-GlyGlu-CycMSH exhibited very rapid and high tumor uptakes. At 2 h post-injection, $^{111}$In-DOTA-CycMSH and $^{111}$In-DOTA-GlyGlu-CycMSH reached their peak tumor uptake values of 9.53±1.41 and 10.40±1.40% ID/g, respectively. There were 7.54±0.70% ID/g of the $^{111}$In-DOTA-CycMSH and 7.40±0.43% ID/g of the $^{111}$In-DOTA-GlyGlu-CycMSH activities remained in the tumors 4 h post-injection. The tumor uptake values of $^{111}$In-DOTA-CycMSH and $^{111}$In-DOTA-GlyGlu-CycMSH decreased to 2.22±0.51 and 2.37±0.28% ID/g at 24 h post-injection. In competition studies, the tumor uptakes of $^{111}$In-DOTA-CycMSH and $^{111}$In-DOTA-GlyGlu-CycMSH with 10 μg (6.07 nmol) of non-radiolabeled NDP co-injection were only 3.0% and 2.6% of the tumor uptake without NDP co-injection at 2 h after dose administration (P<0.01), demonstrating that the tumor uptakes were specific and receptor-mediated. Whole-body clearance of $^{111}$In-DOTA-CycMSH and $^{111}$In-DOTA-GlyGlu-CycMSH was very rapid, with approximately 90% of the injected radioactivity cleared through the urinary system by 2 h post-injection (Table 1, presented in FIG. 5). Normal organ uptakes of $^{111}$In-DOTA-CycMSH and $^{111}$In-DOTA-GlyGlu-CycMSH were generally very low (<0.8% ID/g) except for the kidneys at all time points investigated in this study. High tumor/blood and tumor/normal organ uptake ratios were demonstrated 2 h post-injection (Table 1, FIG. 5). Although there was no statistical difference in tumor uptake between $^{111}$In-DOTA-CycMSH and $^{111}$In-DOTA-GlyGlu-CycMSH, the renal uptake of $^{111}$In-DOTA-GlyGlu-CycMSH was significantly lower (p<0.05, Table 1) than that of $^{111}$In-DOTA-CycMSH at 2, 4 and 24 h post-injection. $^{111}$In-DOTA-GlyGlu-CycMSH displayed 44% less renal uptake value than $^{111}$In-DOTA-CycMSH at 4 h post-injection. At 24 h after dose administration, the kidney uptake values of $^{111}$In-DOTA-CycMSH and $^{111}$In-DOTA-GlyGlu-CycMSH decreased to 16.00±2.30 and 9.06±1.82% ID/g, respectively. Bone uptake values of $^{111}$In-DOTA-CycMSH and $^{111}$In-DOTA-GlyGlu-CycMSH were low (<0.2% ID/g) at all time points investigated in this study.

Figure 7:
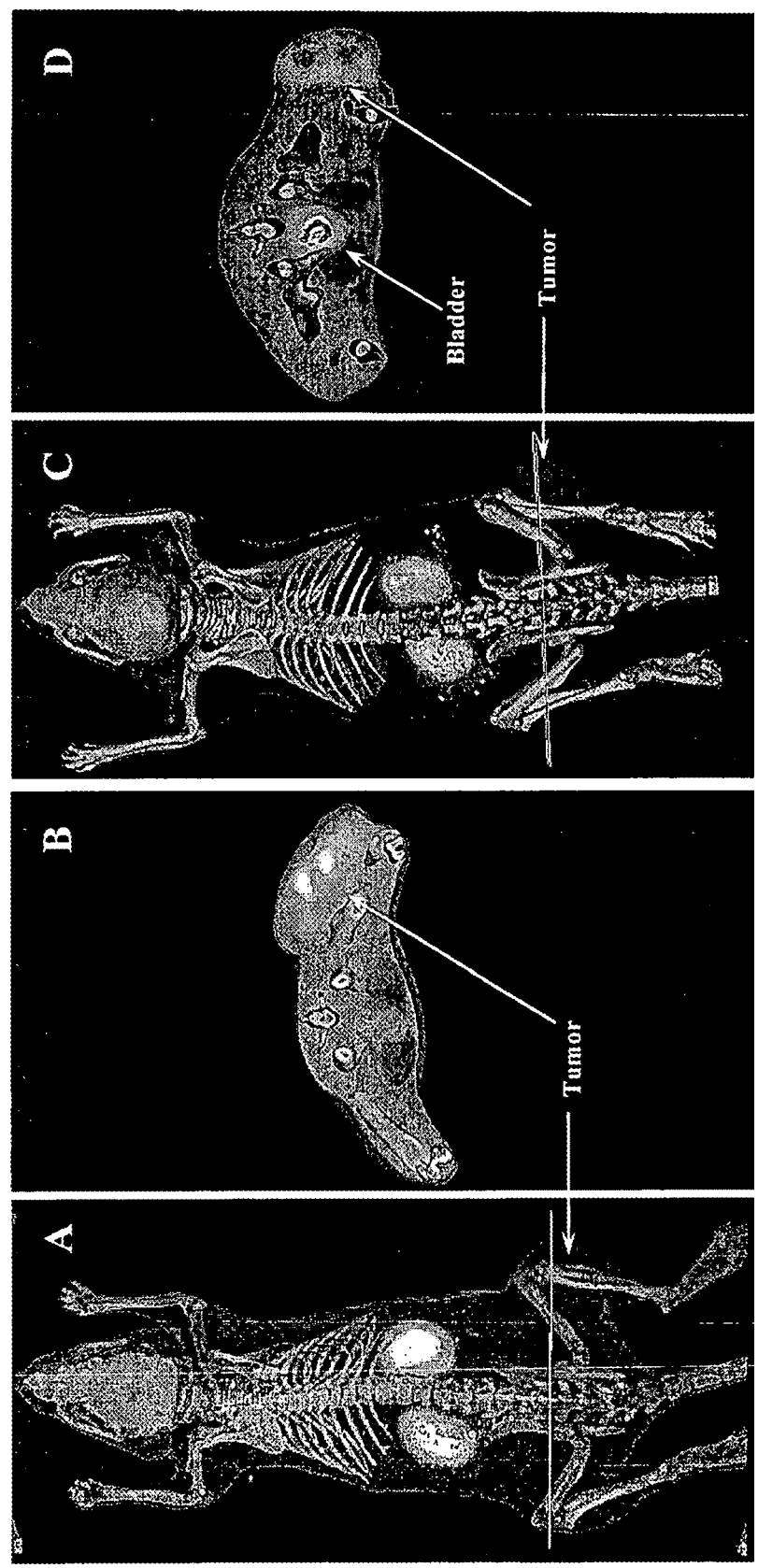
FIG. 7 shows whole-body and transaxial images of $^{111}$In-DOTA-CycMSH (A, B) and $^{111}$In-DOTA-GlyGlu-CycMSH (C, D) in B16/F1 flank melanoma-bearing C57 mice at 2 h post-injection.
Figure 8:
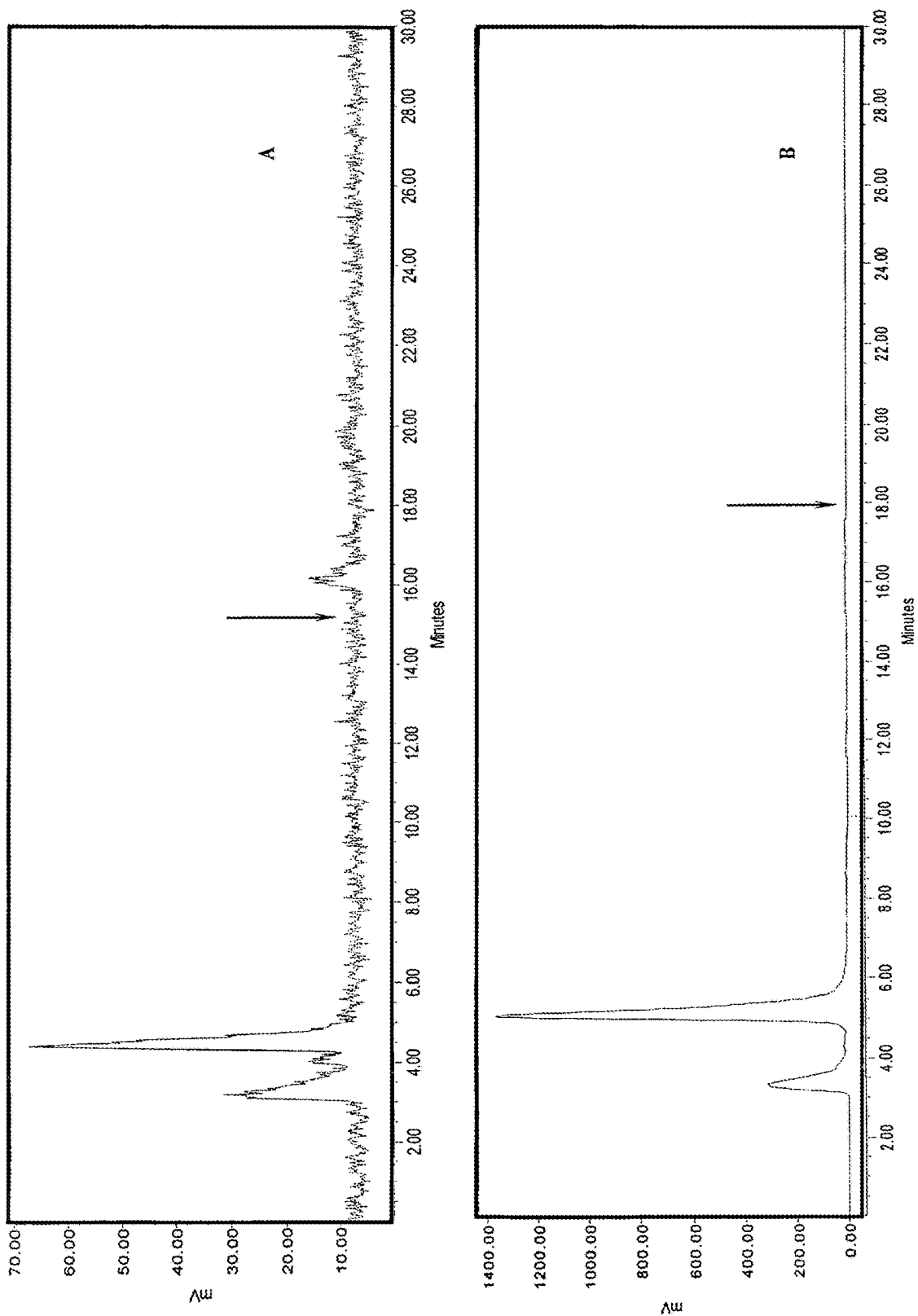
FIG. 8 shows the HPLC profiles of radioactive urine samples of B16/F1 murine melanoma-bearing C57 mice at 2 h post-injection of $^{111}$In-DOTA-CycMSH (A) and $^{111}$In-DOTA-GlyGlu-CycMSH (B). Arrows indicate retention time of the original compound of $^{111}$In-DOTA-CycMSH and $^{111}$In-DOTA-GlyGlu-CycMSH prior to the tail vein injection.

Two B16/F1 murine melanoma-bearing C57 mice were separately injected with $^{111}$In-DOTA-CycMSH (13.7 MBq, 15.2 ng) and $^{111}$In-DOTA-GlyGlu-CycMSH (13.7 MBq, 16.6 ng) through the tail vein to visualize the tumors at 2 h after dose administration. The whole-body SPECT images of the mice were fused with CT images, respectively. The transaxial tumor images and the whole-body images are presented in FIG. 7. Flank melanoma tumors were visualized clearly by both $^{111}$In-DOTA-CycMSH and $^{111}$In-DOTA-GlyGlu-CycMSH at 2 h post-injection. Both $^{111}$In-DOTA-CycMSH and $^{111}$In-DOTA-GlyGlu-CycMSH exhibited high tumor to normal organ uptake ratios except for the kidney, which was coincident with the trend observed in the biodistribution results. In view of the substantial renal uptake values of $^{111}$In-DOTA-CycMSH and $^{111}$In-DOTA-GlyGlu-CycMSH in the biodistribution results, the urinary metabolites of $^{111}$In-DOTA-CycMSH and $^{111}$In-DOTA-GlyGlu-CycMSH were analyzed by RP-HPLC at 2 h post-injection. The HPLC elution profiles of $^{111}$In-DOTA-CycMSH and $^{111}$In-DOTA-GlyGlu-CycMSH are shown in FIG. 8. All of $^{111}$In-DOTA-CycMSH and $^{111}$In-DOTA-GlyGlu-CycMSH were transformed to two more polar metabolites at 2 h post-injection, respectively.

Discussion

Previous publications have demonstrated that cyclization of α-MSH peptide analogues was able to improve the binding affinities and in vivo stability of peptides (14-16). The cyclic peptides possess less conformational freedom and higher stability than the linear peptides due to the stabilization of secondary structures, such as beta turns. The stabilization of secondary structures makes the cyclic peptides better fit receptor binding pocket, enhancing the binding affinities of the cyclic peptides. Peptide cyclization can be achieved through disulfide bridges, lactam bridges, covalent bonds such as N—N and N—C bonds or metal coordination. Site-specific bond formation or metal coordination allows one to control the ring size of the cyclic peptide, which is critical for optimal receptor binding. Over the past several years, we have successfully employed radiometal to cyclize CCMSH peptides through radiolabeling processes (6, 7, 18). Labeling the CCMSH peptides with $^{99m}$Tc or $^{188}$Re simultaneously completed the peptide cyclization and the coupling of radionuclides to the peptides for melanoma imaging or therapy. The metal cyclization made α-MSH peptide analogues resistant to chemical and proteolytic degradation in vivo (18, 19). Furthermore, the metal cyclization resulted in greater tumor uptake and lower renal uptake values of the radiolabeled peptides compared to the disulfide bridge cyclization (19), demonstrating that the different cyclization strategies affect the biodistribution properties of radiolabeled peptides with similar in vitro receptor binding affinities.

Two novel lactam bridge-cyclized α-MSH peptide analogues were synthesized to examine the effect of lactam bridge cyclization on the tumor targeting and pharmacokinetics of the radiolabeled peptides. DOTA-CycMSH and DOTA-GlyGlu-CycMSH displayed $IC_{50}$ values of 1.75 and 0.9 nM, that were comparable to metal- and disulfide-cyclized α-MSH peptide analogues previously reported (19). The lactacm bridge cyclization remained the nanomolar receptor binding affinities of the peptides, demonstrating its suitability and feasibility as a strategy to cyclize the peptides. Both $^{111}$In-DOTA-CycMSH and $^{111}$In-DOTA-GlyGlu-CycMSH exhibited rapid cellular internalization and extended cellular retention in B16/F1 cells, with approximately 70% of the activity internalized in the cells 40 min post incubation and 90% of internalized activity remained in the cells after 2 h incubation in culture media. Efficient cellular internalization coupled with extended retention made the lactam bridge-cyclized α-MSH peptide analogues suitable for melanoma imaging and therapy (6, 23).

Both $^{111}$In-DOTA-CycMSH and $^{111}$In-DOTA-GlyGlu-CycMSH exhibited high receptor-mediated tumor uptakes of 9.53±1.41 and 10.40±1.40% ID/g at 2 h post-injection, respectively. The tumor uptakes of $^{111}$In-DOTA-CycMSH and $^{111}$In-DOTA-GlyGlu-CycMSH (lactam bridge-cyclized α-MSH peptides) were comparable to that of $^{111}$In-DOTA-ReCCMSH (a metal-cyclized α-MSH peptide), but slightly higher than the tumor uptake of $^{111}$In-DOTA-[$Cys^{4,10}$, D-$Phe^7$]-α-$MSH_{4-13}$ ($^{111}$In-DOTA-CMSH, a disulfide bridge-cyclized α-MSH peptide) (19). Two novel $^{111}$In-labeled DOTA-conjugated linear α-MSH peptide analogues, [$Nle^4$, $Asp^5$, D-$Phe^7$, $Lys^{11}$(DOTA)-$^{111}$In]-α-$MSH_{4-11}$ ($^{111}$In-DOTA-NAPamide) and $^{111}$In-DOTA-[β-$Ala^3$, $Nle^4$, $Asp^5$, D-$Phe^7$, $Lys^{10}$]-α-$MSH_{3-10}$ ($^{111}$In-DOTA-$MSH_{oct}$), were reported for melanoma imaging (11, 12). $^{111}$In-DOTA-NAPamide displayed greater tumor uptake values and better pharmacokinetics than $^{111}$In-DOTA-$MSH_{oct}$. The tumor uptake values of $^{111}$In-DOTA-NAPamide were 7.56±0.51% ID/g at 4 h and 2.32±0.28% ID/g at 24 h post-injection in the B16/F1 melanoma mouse model (12). Both $^{111}$In-DOTA-CycMSH and $^{111}$In-DOTA-GlyGlu-CycMSH exhibited comparable tumor uptake values with $^{111}$In-DOTA-NAPamide at 4 and 24 h post-injection. Flank melanoma tumors were clearly visualized with $^{111}$In-DOTA-CycMSH and $^{111}$In-DOTA-GlyGlu-CycMSH at 2 h post-injection by SPECT/CT images (FIG. 7). The SPECT imaging of tumors accurately matched the anatomical information from CT images. $^{111}$In-DOTA-CycMSH and $^{111}$In-DOTA-GlyGlu-CycMSH displayed high tumor to normal organ uptake ratios except for the kidney, which was coincident with the trend observed in biodistribution results. The high receptor-mediated tumor uptake and tumor to normal organ uptake ratios highlighted the potential of radiolabeled lactam bridge-cyclized α-MSH peptides as a novel class of peptide radiopharmaceuticals for melanoma imaging.

Both biodistribution results and SPECT/CT images demonstrated that the kidney was primary excretion pathway of the radiolabeled lactam bridge-cyclized α-MSH peptides. The strategy of infusing basic amino acids such as lysine or arginine has been employed to decrease the renal uptakes of radiolabeled peptides by shielding the electrostatic interaction between positively-charged peptides and negatively-charged surface of tubule cells (7, 24, 25). Recently, it has been reported that different pathways may play roles in the mechanism of the renal uptake of radiolabeled peptides besides the electrostatic interaction between the positively-charged peptides and negatively-charged tubule cells (26, 27). For instance, the use of colchicine, which prevents endocytosis in tubular cells, has successfully decreased the renal uptake up to 25% in a rat model (27). Moreover, transmembrane glycoproteins such as megalin, have been reported to be involved in the renal uptakes of radiolabeled somatostatin analogues (28). Since the extracellular domains of megalin can accommodate a variety of ligands, megalin may be involved in the renal uptakes of other radiolabeled peptides.

Glutamic acid has been introduced into the peptide sequences to reduce the renal uptakes of radiolabeled metal-cyclized α-MSH peptides (29), as well as a PKM linker to modify the biodistribution of radiolabeled RGD peptides (30-35). In this study, the structural modification of increasing the overall negative charge of the peptide (introducing a glutamic acid) was investigated to demonstrate whether the structural modification could reduce the renal uptake values of the radiolabeled peptides. As a matter of fact, the introduction of a negatively-charged glutamic acid as a linker significantly ($p<0.05$) decreased the renal uptake of $^{111}$In-DOTA-GlyGlu-CycMSH by 44% compared to $^{111}$In-DOTA-CycMSH (Table 1, FIG. 5) 4 h post-injection, suggesting that the electrostatic interaction played an important role in the renal uptakes of $^{111}$In-DOTA-CycMSH and $^{111}$In-DOTA-GlyGlu-CycMSH. The urine analysis showed that both $^{111}$In-DOTA-CycMSH and $^{111}$In-DOTA-GlyGlu-CycMSH were metabolized into two moieties that might be responsible for the activity retention in kidneys. The kidney uptake value of $^{111}$In-DOTA-GlyGlu-CycMSH was 29% higher than $^{111}$In-DOTA-ReCCMSH at 4 h post-injection. However, the renal uptake value of $^{111}$In-DOTA-GlyGlu-CycMSH was only 34% of that of $^{111}$In-DOTA-CMSH at 4 h post-injection, demonstrating that the lactam cyclization was better than the disulfide cyclization in terms of less renal uptake value. Introduction of one more negatively-charged glutamic acid or lysine co-injection might further decrease the renal uptake of In-DOTA-GlyGlu-CycMSH. Another potential strategy to further reduce the kidney uptake would be to use shorter lactam bridge-cyclized α-MSH peptide since lower molecular weight $^{111}$In-DOTA-NAPamide exhibited less kidney uptake than $^{111}$In-DOTA-GlyGlu-CycMSH. Further reduction of the renal uptakes will facilitate the clinical evaluations of this novel class of radiolabeled α-MSH peptides as melanoma imaging probes, as well as promote the potential use of this novel class of radiolabeled α-MSH peptides as therapeutic agents for peptide-targeted radionuclide therapy of melanoma.

In conclusion, $^{111}$In-labeled DOTA-conjugated lactam bridge-cyclized α-MSH peptides exhibited high receptor-mediated tumor uptake coupled with fast whole-body clearance in B16/F1 murine melanoma model. Introduction of a negatively-charged linker (-Gly-Glu-) into the peptide sequence decreased the renal uptakes by 44% without affecting the tumor uptakes 4 h post-injection, considerably enhancing resident time in the animal model. $^{111}$In-labeled lactam bridge-cyclized α-MSH peptide analogues are novel class of peptide radiopharmaceuticals useful for receptor-targeting melanoma imaging and therapy.

Second Set of Examples—Directed to Metastatic Melanoma[2]

[2] Note that the second set of references presented in the reference section applies to this set of experiments/examples directed to metastatic melanoma.

G protein-coupled melanocortin-1 (MC1) receptors have been used as targets to develop melanoma-specific imaging probes due to their over-expression on human and mouse melanoma cells (8-12). Radiolabeled α-melanocyte stimulating hormone (α-MSH) peptide analogues, derived from wild-type α-MSH, are very promising candidates for melanoma imaging and therapy due to their nanomolar MC1 receptor binding affinities and high receptor-mediated tumor uptakes in murine melanoma-bearing mice and human melanoma xenografts (13-17). Novel $^{111}$In-labeled 1,4,7,10-Tetraazacyclododecane-1,4,7,10-tetraacetic acid (DOTA)-conjugated lactam bridge-cyclized α-MSH peptides were developed to target MC1 receptors for melanoma imaging as described in the examples above. Lactam bridge-cyclization was employed to improve the stabilities of the peptides against the proteolytic degradations in vivo and enhance the binding affinities of the peptides through stabilizing their secondary structures such as beta turns (19-22). DOTA was coupled to the lactam bridge-cyclized peptides directly or through a negatively-charged amino acid linker (-Gly-Glu-) to determine the effect of a negatively-charged linker in reducing the renal uptakes of $^{111}$In-labeled lactam bridge-cyclized peptides. Introduction of a negatively-charged amino acid linker (-Gly-Glu-) into the peptide sequence decreased the renal uptakes by 44% without affecting the tumor uptakes 4 h post-injection. $^{111}$In-labeled DOTA-Gly-Glu-CycMSH (DOTA-Gly-Glu-c[Lys-Nle-Glu-His-DPhe-Arg-Trp-Gly-Arg-Pro-Val-Asp]) exhibited high receptor-mediated tumor uptake (10.40±1.40% ID/g at 2 h post-injection) in flank B16/F1 murine melanoma-bearing mouse model (18), highlighting the potential of using DOTA-GlyGlu-CycMSH as a melanoma-specific imaging probe for metastatic melanoma detection.

In these examples, $^{111}$In-labeled DOTA-GlyGlu-CycMSH was further evaluated in B16/F10 pulmonary metastatic melanoma model to validate its feasibility as an effective melanoma-specific imaging probe for melanoma metastases detection. The biodistribution of $^{111}$In-labeled DOTA-GlyGlu-CycMSH was determined in the B16/F10 pulmonary metastatic melanoma-bearing C57 mice and compared with that in the normal C57 mice. Dual-modality small animal SPECT/CT (Nano-SPECT/CT®) was used to detect different-stage pulmonary melanoma metastases using $^{111}$In-labeled DOTA-GlyGlu-CycMSH as an imaging probe to monitor the development of melanoma metastatases. The imaging properties on melanoma metastases between $^{18}$F-FDG PET imaging and $^{111}$In-DOTA-GlyGlu-CycMSH SPECT/CT imaging were compared by injecting $^{18}$F-FDG and $^{111}$In-DOTA-GlyGlu-CycMSH with a time interval of 26 h in a pulmonary metastatic melanoma-bearing mouse, respectively.

Materials and Methods

Chemicals and Reagents: Amino acid and resin were purchased from Advanced ChemTech Inc. (Louisville, Ky.) and Novabiochem (San Diego, Calif.). DOTA-tri-t-butyl ester was purchased from Macrocyclics Inc. (Richardson, Tex.). $^{111}$InCl$_3$ was purchased from Trace Life Sciences, Inc. (Dallas, Tex.). $^{125}$I-Tyr$^2$-[Nle$^4$, D-Phe$^7$]-α-MSH {$^{125}$I-(Tyr$^2$)-NDP-MSH} was obtained from PerkinElmer, Inc. (Shelton, Conn.). All other chemicals used in this study were purchased from Thermo Fischer Scientific (Waltham, Mass.) and used without further purification. B16/F10 murine melanoma cells were obtained from American Type Culture Collection (Manassas, Va.).

MC1 Receptor Quantitation Assay: The MC1 receptor density was determined on B16/F10 melanoma cells. One million B16/F10 cells were incubated at room temperature (25° C.) for 2 h in the presence of an increasing concentration (2.5, 5.0, 10, 15, 20, 40, 60, 100 nCi) of $^{125}$I-(Tyr$^2$)-NDP-MSH in 0.5 mL of binding media {Minimum Essential Medium (MEM) with 25 mM N-2-hydroxyethylpiperazine-N'-2-ethanesulfonic acid (HEPES), 0.2% bovine serum albumin (BSA), 0.3 mM 1,10-phenanthroline}. The reaction media were aspirated after incubation. Cells were rinsed with 0.5 mL of ice-cold pH 7.4, 0.2% BSA/0.01 M phosphate buffered saline (PBS) twice, and then the levels of activity associated with the cells were measured in a Wallac 1480 automated gamma counter (PerkinElmer, N.J.). Non-specific binding was determined by incubating the cells and $^{125}$I-(Tyr$^2$)-NDP-MSH with non-radioactive NDP-MSH at a final concentration of 10 μM. Specific binding was obtained by subtracting the nonspecific binding from total binding. Maximum specific binding (Bmax) was estimated from nonlinear curve fitting of specific binding (dpm) versus the concentration of $^{125}$I-(Tyr$^2$)-NDP-MSH (fmole/mL) using Prism software (GraphPad Software, La Jolla, Calif.).

In vitro Competitive Binding Assay: The IC$_{50}$ value of DOTA-GlyGlu-CycMSH was determined in B16/F10 cells. The cells were harvested and seeded into a 24-well cell culture plate (5×10$^5$/well) and incubated at 37° C. overnight. After being washed once with binding media, the cells were incubated at 25° C. for 2 h with approximately 50,000 cpm of $^{125}$I-(Tyr$^2$)-NDP-MSH in the presence of increasing concentrations of DOTA-GlyGlu-CycMSH ($10^{-12}$ to $10^{-5}$ M) in 0.3 mL of binding media. The reaction media were aspirated after incubation. Cells were rinsed with 0.5 mL of ice-cold pH 7.4, 0.2% BSA/0.01 M PBS twice, and then lysed in 0.5 mL of 1 N NaOH for 5 min. The activities associated with the cells were measured in a gamma counter. The IC$_{50}$ value was calculated by using Prism software.

Cellular Internalization and Efflux of $^{111}$In-DOTA-Gly-Glu-CycMSH: DOTA-GlyGlu-CycMSH was synthesized as described previously (18) and identified by mass spectrometry. $^{111}$In-DOTA-GlyGlu-CycMSH was prepared in a 0.5 M NH$_4$OAc-buffered solution at pH 5.4 according to the published procedure (18). Briefly, 50 μl of $^{111}$InCl$_3$ (37-74 MBq in 0.05 M HCl), 10 μl of 1 mg/ml DOTA-GlyGlu-CycMSH aqueous solution and 400 μl of 0.5 M NH$_4$OAc (pH 5.4) were added into a reaction vial and incubated at 75° C. for 45 min. After the incubation, 20 μl of 0.5% EDTA aqueous solution was added into the reaction vial to scavenge potential unbound $^{111}$In. The radiolabeled complex was purified to single species by Waters RP-HPLC (Milford, Mass.) on a Grace Vadyc C-18 reverse phase analytical column (Deerfield, Ill.) using a 20-minute gradient of 16-26% acetonitrile in 20 mM HCl aqueous solution with a flowrate of 1 ml/min. Cellular internalization and efflux of $^{111}$In-DOTA-GlyGlu-CycMSH were evaluated in B16/F10 cells. After being washed once with binding media, B16/F10 cells in cell culture plates were incubated at 25° C. for 20, 40, 60, 90 and 120 min (n=4) in the presence of approximately 200,000 counts per minute (cpm) of HPLC-purified $^{111}$In-DOTA-GlyGlu-CycMSH (0.019 pmol). After incubation, the reaction media were aspirated and the cells were rinsed with 2×0.5 mL of ice-cold pH 7.4, 0.2% BSA/0.01 M PBS. Cellular internalization of $^{111}$In-DOTA-GlyGlu-CycMSH was assessed by washing the cells with acidic buffer [40 mM sodium acetate (pH 4.5) containing 0.9% NaCl and 0.2% BSA] to remove the membrane-bound radioactivity. The remaining internalized radioactivity was obtained by lysing the cells with 0.5 mL of 1 N NaOH for 5 min. Membrane-bound and internalized $^{111}$In activities were counted in a gamma counter. Cellular efflux of $^{111}$In-DOTA-GlyGlu-CycMSH was determined by incubating B16/F10 cells with In-DOTA-GlyGlu-CycMSH for 2 h at 25° C., removing non-specific-bound activity with 2×0.5 mL of ice-cold pH 7.4, 0.2% BSA/0.01 M PBS rinse, and monitoring radioactivity released into cell culture media. At time points of 20, 40, 60, 90 and 120 min, the radioactivities on the cell surface and in the cells were separately collected and counted in a gamma counter.

Biodistribution Studies: All the animal studies were conducted in compliance with Institutional Animal Care and Use Committee approval. B16/F10 pulmonary metastatic melanoma model was established by injecting 0.2 million of cultured B16/F10 cells into each C57 mouse (Harlan, Indianapolis, Ind.) through the tail vein. The B16/F10 pulmonary metastatic melanoma-bearing C57 mice were used for biodistribution studies 16 days after the cell injection. The pharmacokinetics of $^{111}$In-DOTA-GlyGlu-CycMSH was determined in B16/F10 pulmonary metastatic melanoma-bearing and normal C57 mice. HPLC-purified 0.037 MBq of $^{111}$In-DOTA-GlyGlu-CycMSH was injected into each mouse through the tail vein. Groups of 5 mice were sacrificed at 2, 4 and 24 h post-injection, and tumors and organs of interest were harvested, weighed and counted. Blood values were taken as 6.5% of the whole-body weight. Statistical analysis was performed using the Student's t-test for unpaired data. A 95% confidence level was chosen to determine the significance between the activity distribution in pulmonary metastatic melanoma-bearing and normal mice, with p<0.05 being significantly different.

Metastatic Melanoma Imaging: A pulmonary metastatic melanoma-bearing mouse was used for [$^{18}$F]FDG PET imaging 16 days after the cell injection and used for $^{111}$In-DOTA-GlyGlu-CycMSH SPECT/CT imaging on next day (a time interval of 26 h) to compare the difference in detection efficiency between [$^{18}$F]FDG and $^{111}$In-DOTA-GlyGlu-CycMSH. The mouse was injected with 35.15 MBq of commercial [$^{18}$F]FDG (Biotech, N. Mex.) via the tail vein. At 1 h post-injection, the mouse was anesthetized with 1.5% isoflurane and placed in the prone position near the center of the field of view of small animal PET (LabPET™) (Gamma Medica-Ideas, Sherbrooke, Quebec). A 30-min static scan was acquired, and the image was reconstructed by maximum likelihood estimation method (MLEM). The mouse was returned to the cage for recovery after the $^{18}$F-FDG PET imaging study was completed. The same mouse was injected with 24.05 MBq of $^{111}$In-DOTA-GlyGlu-CycMSH via the tail vein 24 h after the $^{18}$F-FDG PET imaging study. The mouse was anesthetized with 1.5% isoflurane for small animal SPECT/CT (Nano-SPECT/CT®, Bioscan) imaging 2 h post-injection. The 6-min CT imaging was immediately followed by the focused SPECT imaging of lung. The SPECT scans of 24 projections were acquired and total acquisition time was 45 min. After the focused lung imaging, the mouse was sacrificed with $CO_2$ inhalation for whole-body SPECT/CT imaging. The 9-min CT imaging was immediately followed by the SPECT imaging of whole-body. Reconstructed data from SPECT and CT were visualized and co-registered using InVivoScope (Bioscan, Washington D.C.). Necropsy analysis of the mouse was performed to confirm the pulmonary metastatic melanoma lesions after the SPECT/CT imaging studies were completed. To monitor the development of pulmonary melanoma metstases with $^{111}$In-DOTA-GlyGlu-CycMSH, a pulmonary metastatic melanoma-bearing mouse was injected with 10.36 MBq of $^{111}$In-DOTA-GlyGlu-CycMSH through the tail vein for small animal SPECT/CT imaging 20 days after the cell injection. The mouse was anesthetized with 1.5% isoflurane for SPECT/CT imaging 2 h post-injection as described above. The SPECT/CT images of pulmonary melanoma metastases developed 20 days after the cell injection were compared with the SPECT/CT images of pulmonary melanoma metastases developed 17 days after the cell injection. Necropsy analysis of the mouse was performed after the SPECT/CT imaging studies were completed. The metastatic melanoma-bearing lung was taken out for a SPECT imaging to confirm the uptake of $^{111}$In-DOTA-GlyGlu-CycMSH activity.

Results

Figure 9:
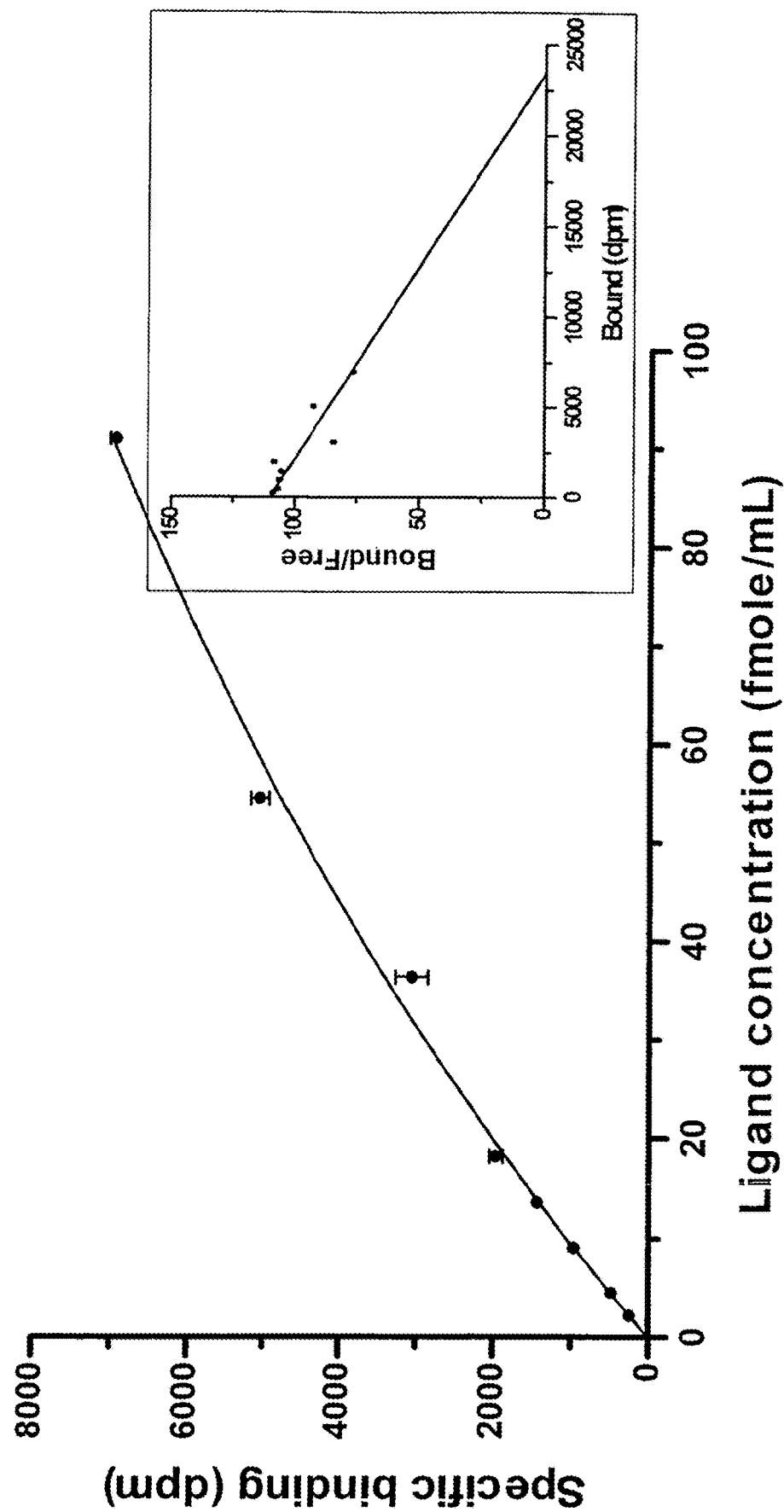
FIG. 9 shows MC1 receptor density in B16/F10 murine melanoma cells. The B$_{max}$ value was 23394 dpm/million cells (2884 receptors/cell).
Figure 10:
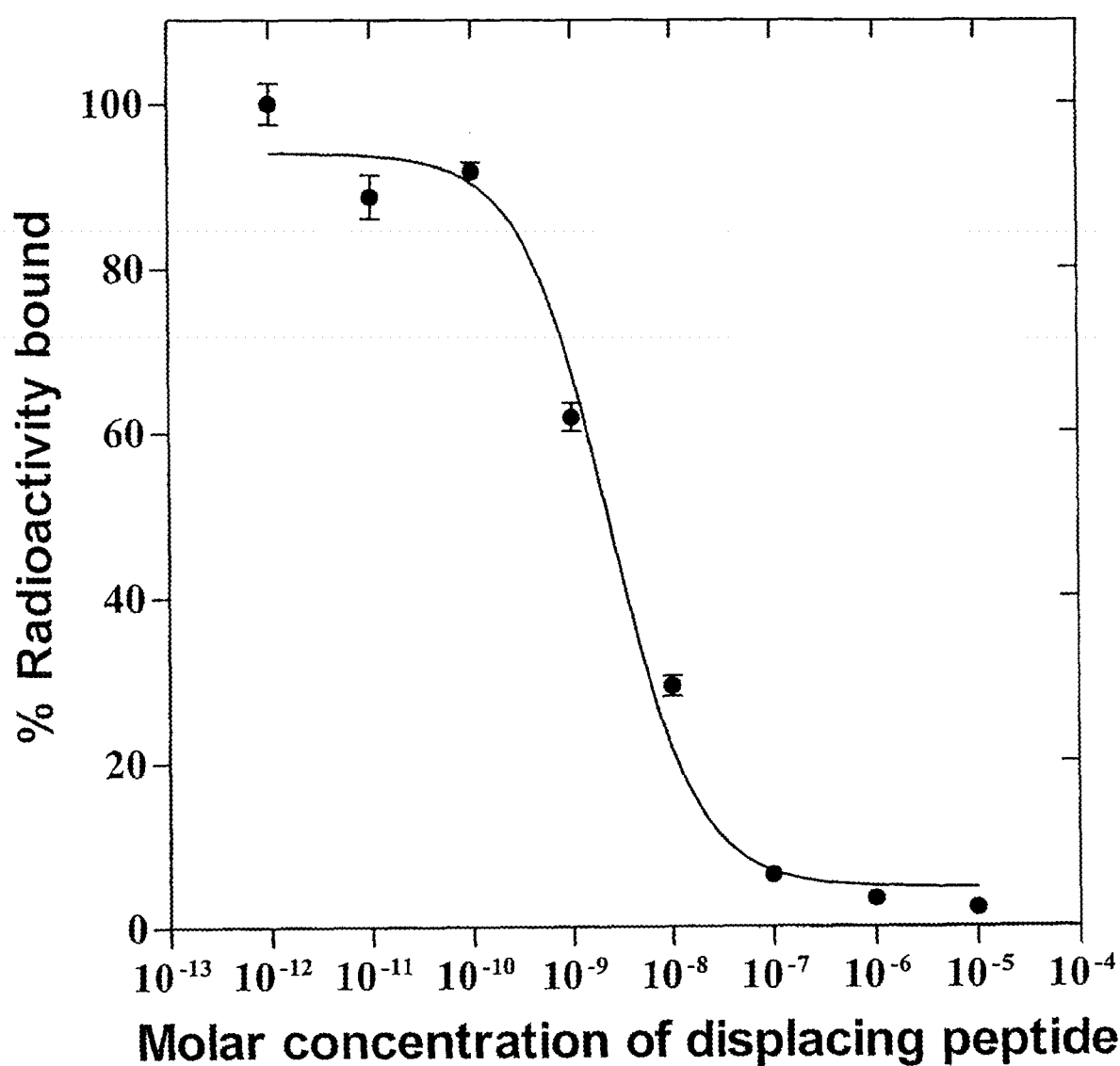
FIG. 10 shows the competitive binding curve of DOTA-GlyGlu-CycMSH in B16/F10 murine melanoma cells. The IC$_{50}$ value of DOTA-GlyGlu-CycMSH was 2.43 nM.
Figure 11:
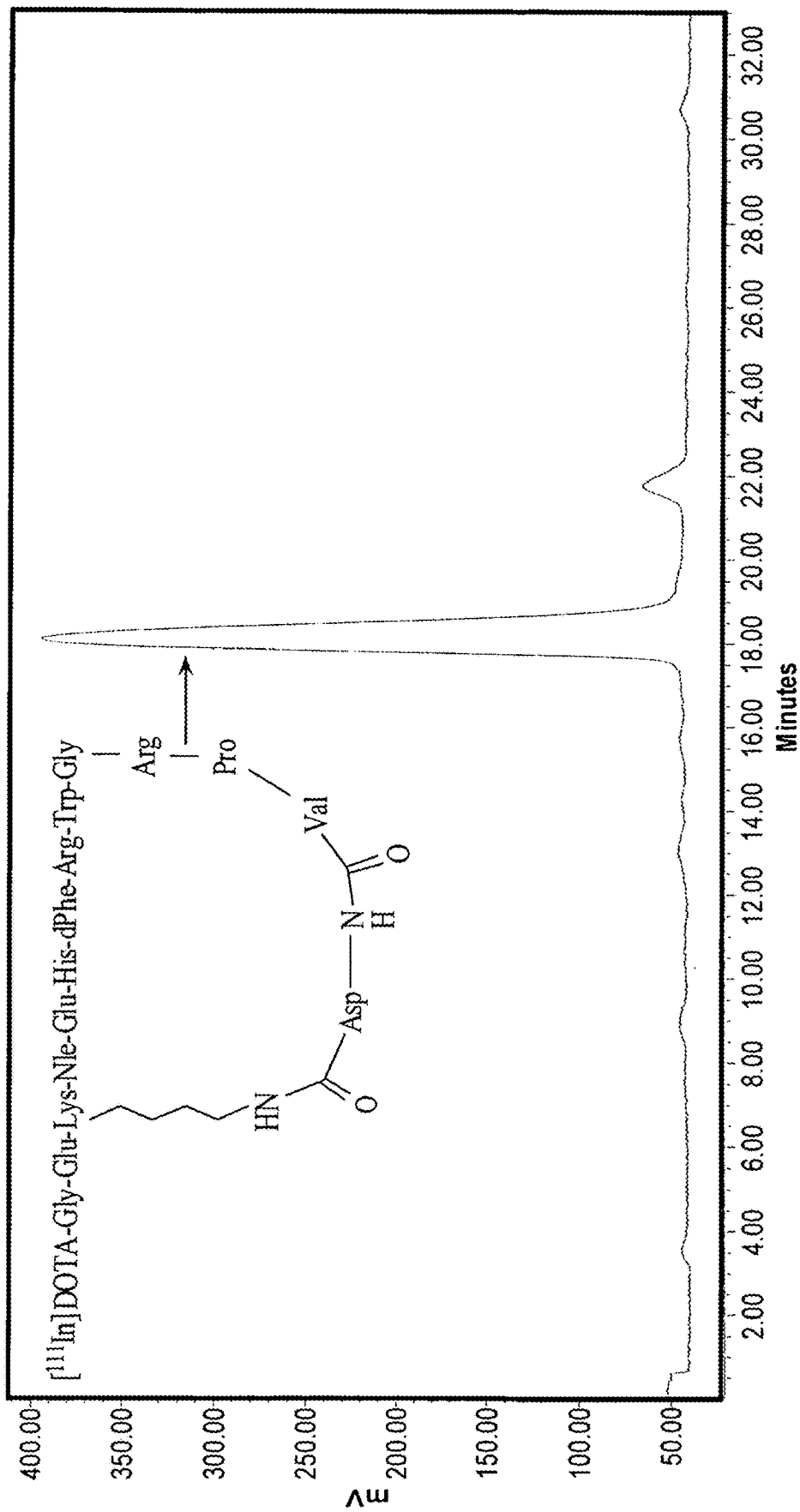
FIG. 11 shows a schematic structure and radioactive HPLC profile of $^{111}$In-DOTA-GlyGlu-CycMSH. The retention time of $^{111}$In-DOTA-GlyGlu-CycMSH was 18.1 min using a 20 min gradient of 16-26% acetonitrile in 20 mM HCl aqueous solution with a flow rate of 1 mL/min.

The MC1 receptor density of B16/F10 cell was determined by saturation binding assay using commercial $^{125}$I-(Tyr$^2$)-NDP-MSH as a radioactive tracer. The saturation curve and scatchard plot are presented in FIG. 9. The Bmax of B16/F10 cells was 23394 dpm/million cells (2884 receptors/cell). DOTA-GlyGlu-CycMSH was synthesized, purified by RP-HPLC and identified by electrospray ionization mass spectrometry. FIG. 10 illustrates the competitive binding curve of DOTA-GlyGlu-CycMSH in B16/F10 cells. The IC$_{50}$ value of DOTA-GlyGlu-CycMSH was 2.43 nM in B16/F10 cells. The peptide was easily labeled with $^{111}$In using a 0.5 M NH$_4$OAc-buffered solution at pH 5.4 with greater than 95% labeling yield. $^{111}$In-DOTH-GlyGlu-CycMSH was completely separated from its excess non-labeled peptide by RP-HPLC. The retention time of $^{111}$In-DOTA-GlyGlu-CycMSH was 18.1 min using a 20 mM gradient of 16-26% acetonitrile in 20 mM HCl aqueous solution with a flow rate of 1 mL/min (FIG. 11). The specific activity of $^{111}$In-DOTA-GlyGlu-CycMSH was 8.23× 10$^8$MBq/g. $^{111}$In-DOTA-GlyGlu-CycMSH was stable in mouse serum at 37° C. for 24 h. The schematic structure of $^{111}$In-DOTA-GlyGlu-CycMSH is shown in FIG. 11.

Figure 12:
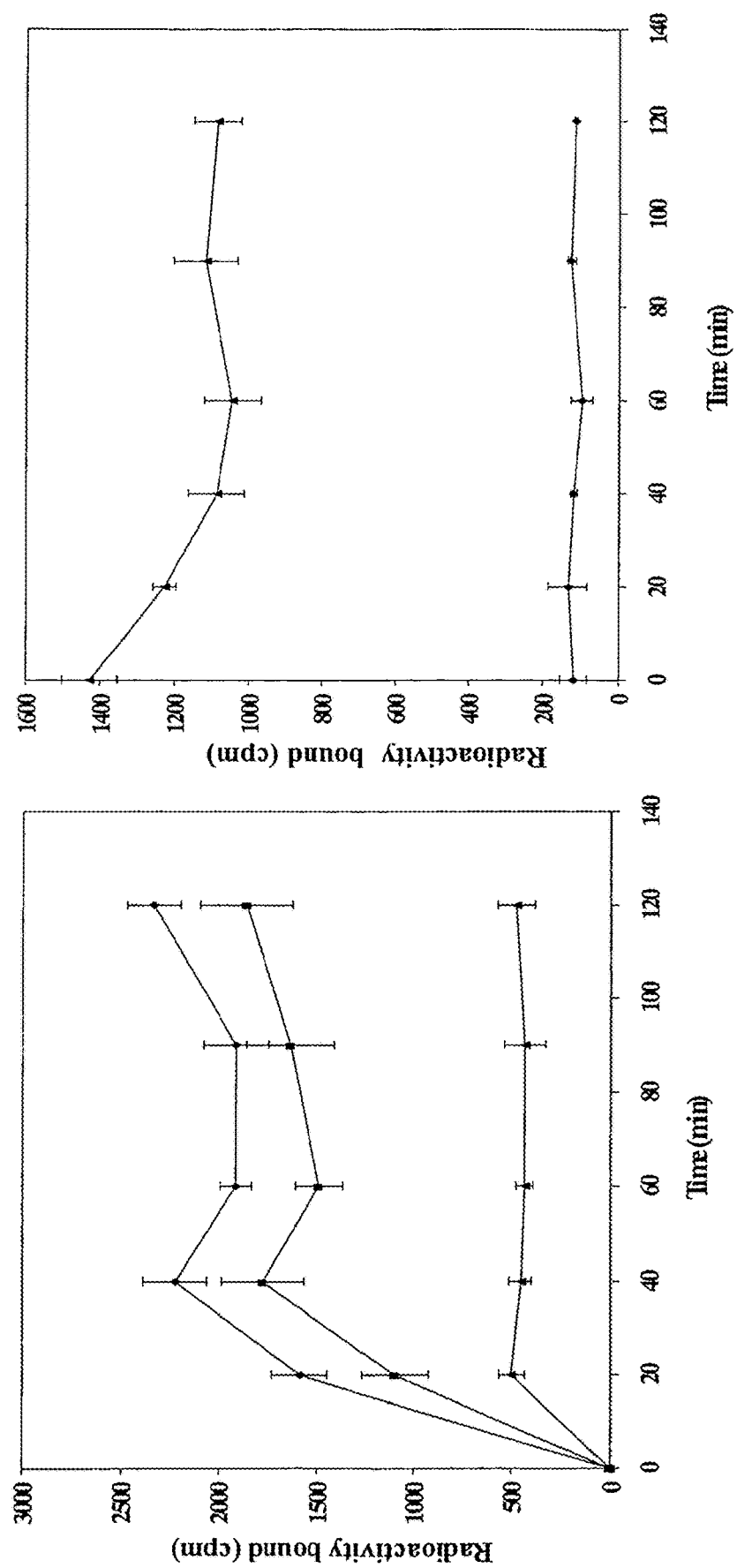
FIG. 12 shows cellular internalization and efflux of $^{111}$In-DOTA-GlyGlu-CycMSH (A and B) in B16/F10 murine melanoma cells at 25° C. Total bound radioactivity (♦), internalized activity (■) and cell membrane activity (▲) were presented as counts per minute (cpm).

Cellular internalization and efflux of $^{111}$In-DOTA-GlyGlu-CycMSH were evaluated in B16/F10 cells. FIG. 12 illustrates cellular internalization and efflux of $^{111}$In-DOTA-GlyGlu-CycMSH. $^{111}$In-DOTA-GlyGlu-CycMSH exhibited rapid cellular internalization and extended cellular retention. There was 68.7±10.8% of $^{111}$In-DOTA-GlyGlu-CycMSH activity internalized in the B16/F10 cells 20 min post incubation. There was 79.7±10.1% of $^{111}$In-DOTA-GlyGlu-CycMSH activity internalized in the cells after 2 h incubation. Cellular efflux experiments demonstrated that 90.6±5.3% of $^{111}$In-DOTA-GlyGlu-CycMSH activity remained inside the cells 2 h after incubating cells in culture media.

The pharmacokinetics and tumor targeting properties of $^{111}$In-DOTA-GlyGlu-CycMSH were determined in B16/F10 pulmonary metastatic melanoma-bearing C57 mice and compared with normal C57 mice at 2, 4 and 24 h post-injection. The biodistribution results of $^{111}$In-DOTA-GlyGlu-CycMSH are shown in Table 2, FIG. 13. $^{111}$In-DOTA-GlyGlu-CycMSH exhibited significantly (p<0.05) higher uptake value in metastatic melanoma-bearing lung than that in normal lung. The uptake values of $^{111}$In-DOTA-GlyGlu- CycMSH radioactivity in the metastatic melanoma-bearing and normal lungs were 2.00±0.74 and 0.08±0.08% ID/g, 1.83±0.12 and 0.05±0.05% ID/g at 2 and 4 h post-injection, respectively. The uptake values of $^{111}$In-DOTA-GlyGlu-CycMSH radioactivity in the metastatic melanoma-bearing and normal lungs were 0.29±0.06 and 0.03±0.02% ID/g at 24 h post-injection. The $^{111}$In-DOTA-GlyGlu-CycMSH displayed higher lung/normal organ uptake ratios in pulmonary metastatic melanoma-bearing mice than that in normal mice (Table 2, FIG. 13). Whole-body clearance of $^{111}$In-DOTA-GlyGlu-CycMSH was rapid, with approximately 84% of the injected radioactivity cleared through the urinary system by 2 h post-injection (Table 2). Approximately 96% of the injected radioactivity cleared out the body at 24 h post-injection.

Figure 14:
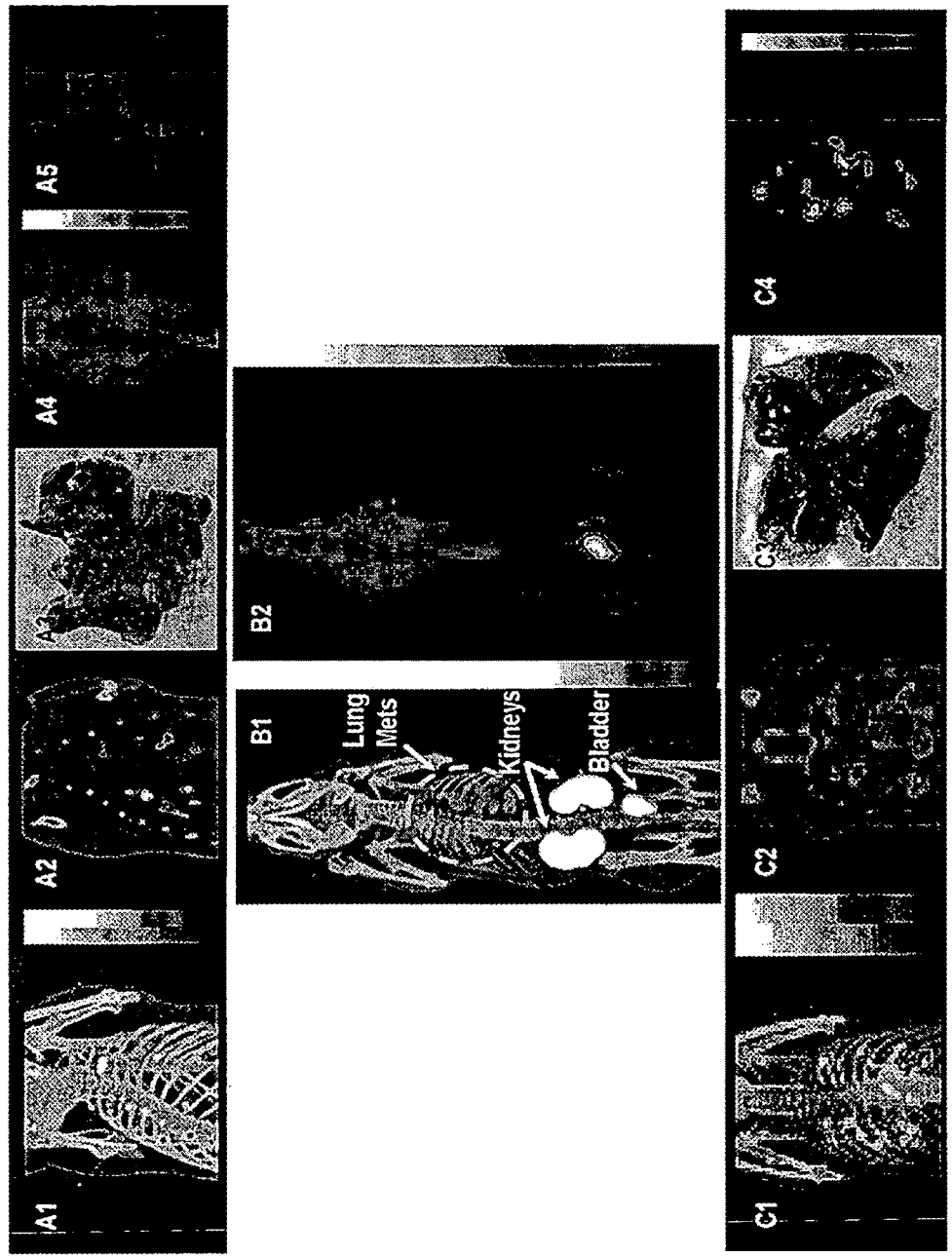
FIG. 14 shows focused 3-dimensional (A1) and coronal (A2) SPECT/CT images of metastatic melanoma-bearing lung (17 days post the cell injection) 2 h post-injection of $^{111}$In-DOTA-GlyGlu-CycMSH; Necropsy picture (A3) of the metastatic melanoma-bearing lung (17 days post the cell injection); Focused 3-dimensional (A4) and saggital (A5) PET images of metastatic melanoma-bearing lung (16 days post the cell injection) 1 h post-injection of [$^{18}$F]FDG; Whole-body SPECT/CT (B1) and PET (B2) images using $^{111}$In-DOTA-GlyGlu-CycMSH and [$^{18}$F]FDG as imaging probes, respectively; Focused 3-dimensional (C1) and coronal (C2) SPECT/CT images of metastatic melanoma-bearing lung (20 days post the cell injection) 2 h post-injection of $^{111}$In-DOTA-GlyGlu-CycMSH; Necropsy picture (C3) and 3-dimensional (C4) SPECT/CT image of the metastatic melanoma-bearing lung (20 days post the cell injection).

One B16/F10 pulmonary melanoma-bearing C57 mouse was injected with [18F]FDG and $^{111}$In-DOTA-GlyGlu-CycMSH via the tail vein (with a time interval of 26 h) to compare melanoma metastases imaging properties 16 and 17 days post the cell injection, respectively. The focused three-dimensional and transaxial SPECT/CT and PET images are presented in FIGS. 14A1-14A5, respectively. The pulmonary metastatic melanoma lesions were visualized by SPECT/CT using $^{111}$In-DOTA-GlyGlu-CycMSH as an imaging probe (FIGS. 14M and 14A2) rather than [18F]FDG PET imaging (FIGS. 14A4 and 14A5). $^{111}$In-DOTA-GlyGlu-CycMSH clearly identified individual metastatic melanoma deposits (FIGS. 14A1 and 14A2). Melanoma metastases were confirmed by necropsy picture (FIGS. 14A3). Whole-body SPECT/CT and PET images are also presented in FIGS. 14B1 and 14B2. Pulmonary metastatic melanoma lesions were visualized with $^{111}$In-DOTA-GlyGlu-CycMSH by whole-body SPECT/CT imaging (FIG. 14B1). $^{111}$In-DOTA-GlyGlu-CycMSH was mainly excreted through the urinary system. The accumulation of $^{111}$In-DOTA-GlyGlu-CycMSH activity in normal organs was extremely low except for the kidneys in the whole-body SPECT/CT image, which was consistent with the biodistribution results. [18F]FDG exhibited much higher normal organ accumulation than $^{111}$In-DOTA-GlyGlu-CycMSH except for the kidneys (FIG. 14B2). Another pulmonary melanoma-bearing C57 mouse was injected with $^{111}$In-DOTA-GlyGlu-CycMSH via the tail vein 20 days post the cell injection to monitor the development of melanoma metastases. The focused three-dimensional and transaxial tumor images are presented in FIGS. 14C1 and 14C2. Compared to the pulmonary melanoma metastases developed 17 days post the cell injection, more and bigger metastatic melanoma lesions appeared in the lung 20 days post the cell injection. $^{111}$In-DOTA-GlyGlu-CycMSH clearly identified both distinct metastatic melanoma deposits and bigger metastatic melanoma lesions (FIGS. 14C1 and 14C2). The lung was taken out for necropsy examination to confirm the melanoma metastases after the SPECT/CT imaging studies were completed. Furthermore, the metastatic melanoma-bearing lung was examined by SPECT imaging to confirm the uptake of $^{111}$In-DOTA-GlyGlu-CycMSH activity. The necropsy picture and SPECT image of the melanoma metastases-bearing lung are presented in FIGS. 14C3 and 14C4. Melanoma metastases were confirmed by both necropsy picture and SPECT image (FIGS. 14C3 and 14C4).

Discussion

High mortality of malignant melanoma is associated with the occurrence of metastatic melanoma due to its aggressiveness and resistance to current chemotherapy and immunotherapy regimens. Early diagnosis and prompt surgical removal of the malignant melanoma provide the patients the best opportunities for cures or prolonged survival. Despite the clinical use of [18F]FDG in melanoma staging and melanoma metastases identification, [18F]FDG is not a melanoma-specific imaging agent and is also not effective in imaging small melanoma metastases (<5 mm) and melanomas that have primary energy sources other than glucose (5-7). Alternatively, $^{111}$In-labeled lactam bridge-cyclized α-MSH peptide ($^{111}$In-DOTA-GlyGlu-CycMSH) was reported as a potential melanoma-specific SPECT imaging probe targeting the MC1 receptor for melanoma detection in our previous report (18), highlighting its potential as an effective imaging probe for metastatic melanoma detection. Hence, $^{111}$In-DOTA-GlyGlu-CycMSH was further evaluated in B16/F10 pulmonary metastatic melanoma mouse model in this report.

B16/F10 melanoma cell line is a murine melanoma cell line with high metastatic potential (23). Therefore, B16/F10 cells were injected into the tail vein to generate an experimental metastatic melanoma mouse model to evaluate the tumor targeting and imaging properties of $^{111}$In-DOTA-GlyGlu-CycMSH in this report. The number of experimental pulmonary melanoma metastases was reported to be proportional to the number of melanoma cells intravenously injected (23). The pulmonary metastatic melanoma increased in size and number with time after the melanoma cell injection (24). More and bigger metastatic melanoma lesions appeared in lung 17 days post the cell injection than that in lung 14 days post the cell injection (24). Beside the lung metastases, intravenous injection of B16/F10 melanoma cells also induced extra-pulmonary metastases such as bone, adrenal gland, liver and muscle metastases (25-31). In this report, the mouse was injected with $2 \times 10^5$ B16/F10 cells to generate pulmonary melanoma metastases to evaluate the tumor targeting and imaging properties of $^{111}$In-DOTA-GlyGlu-CycMSH. The pulmonary metastatic melanoma-bearing mice were used for the biodistribution studies 16 days post the cell injection. All the mice used in the biodistribution studies developed pulmonary melanoma metastases. Recently, small animal CT has been investigated to follow the development and progression of melanoma metastases after the intravenous injection of B16/F10 melanoma cells (25). Among the pulmonary and extra-pulmonary melanoma metastases, the small animal CT imaging was reported to be best suited to detect the lesions in the lung and bone that provide high contrast between the tumor lesions and normal lung or bone tissues. Pulmonary metastatic melanoma deposits were initially detectable by small animal CT approximately 15-18 days post tail vein inoculation of B16/F10 melanoma cells (25). The growth of melanoma metastases in the lung could be monitored with additional CT studies over time (25). In this report, small animal CT imaging was performed 15 days post the cell injection to select pulmonary metastatic melanoma-bearing mice for PET and SPECT/CT imaging studies 16 and 20 days post the cell injection, respectively.

The characteristics of the cells played important roles in the development of melanoma metastases (23). Hence, the MC1 receptor density of B16/F10 cell and the binding affinity of DOTA-GlyGlu-CycMSH were determined in this report. The Bmax of the B16/F10 cell was 2884 receptors/cell, which was in the range of receptor densities of human melanoma cell lines (12). DOTA-GlyGlu-CycMSH exhibited 2.43 nM MC1 receptor binding affinity in B16/F10 cells, making the receptor-targeting B16/F10 melanoma imaging possible. $^{111}$In-DOTA-GlyGlu-CycMSH exhibited rapid cellular internalization and extended cellular retention in B16/F10 cells, with approximately 70% of the activity internalized in the cells 20 min post incubation and 90% of internalized activity remained in the cells after 2 h incubation in culture media. Efficient cellular internalization coupled with extended retention made the diagnostic and therapeutic radionuclide-labeled DOTA-GlyGlu-CycMSH suitable for melanoma imaging and therapy (10, 32). The comparison of biodistribution results of the $^{111}$In-DOTA-GlyGlu-CycMSH in pulmonary metastatic melanoma-bearing and normal mice demonstrated the feasibility of using $^{111}$In-DOTA-GlyGlu-CycMSH to identify the pulmonary melanoma metastases. The uptake values of $^{111}$In-DOTA-GlyGlu-CycMSH radioactivity in the metastatic melanoma-bearing lung (16 days post the cell injection) were 25.0 and 36.6 times the lung uptake values in normal lung at 2 and 4 h post-injection, respectively. Even 24 h post-injection, the uptake value of $^{111}$In-DOTA-GlyGlu-CycMSH radioactivity in the metastatic melanoma-bearing lung was 9.7 times the lung uptake value in normal lung.

MC1 receptor-targeting radiolabeled α-MSH peptides were reported to be effective in detecting experimental melanoma metastases (15, 16, 33). For instance, $^{111}$In-DOTA-MSH$_{oct}$ and $^{67}$Ga-DOTA-NAPamide were able to image the B16/F1 lung or liver melanoma metastases by tissue autoradiograph (15, 16). $^{111}$In-DOTA-MSH$_{oct}$ and $^{67}$Ga-DOTA-NAPamide identified both melanotic and amelanotic melanoma metastases in lung (15, 16), demonstrating the possibilities of radiolabeled linear NDP derivatives for metastatic melanoma detection. Recently, $^{99m}$Tc- and $^{111}$In-labeled metal-cyclized α-MSH peptides were reported to be successful in visualizing B16/F10 pulmonary melanoma metastases (24 days post the cell injection) by small animal SPECT/CT (Micro-CAT II SPECT/CT) in sacrificed melanoma-bearing mice (33), validating the feasibility of using radiolabeled metal-cyclized α-MSH peptides for non-invasive melanoma metastases imaging. In this report, lactam bridge-cyclized $^{111}$In-DOTA-GlyGlu-CycMSH was evaluated in live B16/F10 pulmonary metastatic melanoma-bearing mice (17 and 20 days post the cell injection) for its ability for non-invasive imaging melanoma metastases and monitoring the development of melanoma metastases. Dual-modality small animal SPECT/CT (Nano-SPECT/CT®) was used to detect the pulmonary melanoma metastases using $^{111}$In-DOTA-GlyGlu-CycMSH as an imaging probe to target the MC1 receptors on the melanoma metastases. Nano-SPECT/CT® is a powerful tool combining the high spatial resolution of CT and high sensitivity of SPECT. Co-registration of the CT data with the SPECT data allowed accurate identification and localization of the melanoma metastases which improves the detection of metastatic deposits in the body cavity where small animal CT alone faces challenges without the addition of a contrast agent. Pulmonary metastatic melanoma lesions in live mice were clearly imaged by Nano-SPECT/CT® with $^{111}$In-DOTA-GlyGlu-CycMSH 2 h post-injection (FIGS. 14A1 and 14A2). The SPECT/CT images were coincident with the biodistribution results in B16/F10 pulmonary metastatic melanoma model (Table 2, FIG. 13). $^{111}$In-DOTA-GlyGlu-CycMSH clearly identified the individual metastatic deposits developed in the lung 17 days post the cell injection (FIGS. 14A1 and 14A2). The comparison of $^{111}$In-DOTA-GlyGlu-CycMSH images and [$^{18}$F]FDG images (FIGS. 14A4 and 14A5) in the same melanoma-bearing mouse demonstrated that $^{111}$In-DOTA-GlyGlu-CycMSH was a superior imaging probe for pulmonary melanoma metastases detection. [$^{18}$F]FDG failed in identifying the pulmonary melanoma metastases that were clearly imaged with $^{111}$In-DOTA-GlyGlu-CycMSH. Compared with the SPECT/CT images of pulmonary metastatic melanoma-bearing mouse 17 days post the cell injection (FIGS. 14A1 and 14A2), more and bigger metastatic melanoma lesions were observed in the SPECT/CT images of pulmonary metastatic melanoma-bearing mouse 20 days post the cell injection (FIGS. 14C1 and 14C2). Both individual metastatic foci and bigger lesions (20 days post the cell injection) developed in the lung were clearly visualized with $^{111}$In-DOTA-GlyGlu-CycMSH (FIGS. 14C1 and 14C2), demonstrating the feasibility of using $^{111}$In-DOTA-GlyGlu-CycMSH as an imaging probe to monitor tumor response to therapy. Although more studies need to be conducted, the imaging of metastatic melanoma foci in the earlier stage of development (<17 days) seems possible since the spatial resolution of Nano-SPECT with multiple-pinhole collimator is approximately 0.8-mm for Jaszczak phantom filled with $^{111}$In aqueous solution.

The successful detection of melanoma metastases by Nano-SPECT/CT® with $^{111}$In-DOTA-GlyGlu-CycMSH highlighted the potential application of radiolabeled DOTA-GlyGlu-CycMSH for peptide-targeted radionuclide therapy of metastatic melanoma if the non-specific renal uptake could be further reduced through the administration of positively-charged amino acids. The introduction of a negatively-charged amino acid linker (-Gly-Glu-) successfully reduced the renal uptake of $^{111}$In-DOTA-GlyGlu-CycMSH by 44% without affecting the tumor uptake (18), demonstrating that the electrostatic interaction played an important role in the renal uptake of $^{111}$In-DOTA-GlyGlu-CycMSH. Positively-charged amino acids such as lysine and arginine were successful in reducing the renal uptake of $^{188}$Re-labeled metal-cyclized α-MSH peptides by up to 50% (11). It is highly likely that co-injection of lysine or arginine will further decrease the renal uptake of $^{111}$In-DOTA-GlyGlu-CycMSH. Since DOTA can form stable complexes with a variety of radiometals including diagnostic and therapeutic radionuclides, DOTA-GlyGlu-CycMSH can be potentially labeled with a variety of therapeutic radionuclides such as alpha- and beta-emitters (14, 34-37) to treat the metastatic melanoma at the different stage. For instance, high-energy β-emitters such as $^{90}$Y appear appropriate for the treatment of larger tumors or large tumor burdens (35). Medium- and lower-energy β-emitters, such as $^{177}$Lu (37), may be more suitable for treating smaller tumors or metastatic deposits. Alpha-emitters such as $^{212}$Pb/Bi (14) are attractive for treating small tumor and metastases due to their short path-length and high linear energy transfer (LET). The efficient internalization and extended retention of $^{111}$In-DOTA-GlyGlu-CycMSH demonstrated that the therapeutic effects of alpha- and beta-emitter-labeled DOTA-GlyGlu-CycMSH could be maximized due to the shortened distance between the radiation generated from the radionuclide and the target cell nucleus. Moreover, the toxicity of targeted radionuclide therapy would also be potentially decreased by the efficient internalization and extended retention since the cytotoxic radiation could be selectively and specifically delivered to the tumor cells in an efficient fashion. The combined utilization of diagnostic and therapeutic DOTA-GlyGlu-CycMSH could potentially improve the success of the peptide-targeted radionuclide therapy of melanoma. Imaging patients with $^{111}$In-DOTA-GlyGlu-CycMSH prior to the therapy would allow clinicians to accurately determine accurate patient-specific dosimetry, which would improve the safe and efficacious application of peptide-targeted radionuclide therapy of melanoma.

In conclusion, $^{111}$In-DOTA-GlyGlu-CycMSH exhibit favorable metastatic melanoma targeting and imaging properties and are effective imaging probe and therapeutic agents for metastatic melanoma detection.

Third Set of Examples—Directed to Synthesis and Applicability of Alternative Compounds According to the Present Invention[1]

[1] Note that the third set of references presented in the reference section applies to this third set of experiments/examples.

In this third set of examples, the inventors further examined the effect of structural modifications on receptor binding affinities of lactam bridge-cyclized α-MSH peptides. Two novel DOTA-conjugated lactam bridge-cyclized α-MSH peptides, namely DOTA-GluGlu-CycMSH (1,4,7,10-tetraazacyclododecane-1,4,7,10-tetraacetic acid-Glu-Glu-c[Lys-Nle-Glu-His-DPhe-Arg-Trp-Gly-Arg-Pro-Val-Asp]) and Ac-GluGlu-CycMSH[DOTA](Ac-Glu-Glu-c[Lys(DOTA)-Nle-Glu-His-DPhe-Arg-Trp-Gly-Arg-Pro-Val-Asp]) were synthesized. A negatively-charged linker of -Glu-Glu- was introduced between DOTA and CycMSH sequences to yield DOTA-GluGlu-CycMSH. DOTA was directly attached to the cyclic ring while the N-terminus of the peptide was acetylated to generate Ac-GluGlu-CycMSH [DOTA]. The receptor binding affinities of the lactam-bridged cyclized peptides were determined in B16/F1 melanoma cells.

Experimental Procedures

Chemicals and Reagents: Amino acid and resin were purchased from Advanced ChemTech Inc. (Louisville, Ky.) and Novabiochem (San Diego, Calif.). DOTA-tri-t-butyl ester was purchased from Macrocyclics Inc. (Richardson, Tex.). [111]InCl$_3$ was purchased from Trace Life Sciences, Inc. (Dallas, Tex.). [125]I-Tyr$^2$-[Nle$^4$, D-Phe$^7$]-α-MSH {[125]I-(Tyr$^2$)-NDP-MSH} was obtained from PerkinElmer, Inc. (Shelton, Conn.). All other chemicals used in this study were purchased from Thermo Fischer Scientific (Waltham, Mass.) and used without further purification. B16/F1 murine melanoma cells were obtained from American Type Culture Collection (Manassas, Va.).

Peptide Synthesis: Intermediate scaffolds of (tBu)$_3$ DOTA-Glu(OtBu)-Glu(OtBu)-Lys(Dde)-Nle-Glu(OtBu)-His(Trt)-DPhe-Arg(Pbf)-Trp(Boc)-Gly-Arg(Pbf)-Pro-Val and Ac-Glu(OtBu)-Glu(OtBu)-Lys(Dde)-Nle-Glu(OtBu)-His(Trt)-dPhe-Arg(Pbf)-Trp(Boc)-Gly-Arg(Pbf)-Pro-Val were synthesized on Val-2-Chlorotrityl Chloride (Val-2Cl-Trt) resin using standard 9-fluorenylmethyloxycarbonyl (Fmoc) chemistry by an Advanced ChemTech multiple-peptide synthesizer (Louisville, Ky.). A small aliquot of the scaffold material was cleaved and characterized by liquid chromatography-mass spectroscopy (LC-MS) prior to further peptide synthesis and cyclization. The protecting group (Dde) of the Lys was removed by 2% Hydrazine and branching moieties of the peptides were generated by coupling Fmoc-Asp(OtBu) or Fmoc-Lys(Dde) on the amino group of the Lys side chain manually. For Ac-GluGlu-CycMSH-DOTA peptide, DOTA moiety was coupled to the peptide manually using standard Fmoc chemistry. Protected branched peptides were cleaved from the resin treating with 25% Hexafluoroisopropanol (HFIP) and 5% triisopropylsilane (TIS) in dichloromethane (DCM) and characterized by LC-MS. Peptide cyclization between the acid moiety of Val and the amino group of Asp or Lys coupled to the Lys side chain was achieved by overnight reaction in DMF in the presence of a mixture of 1 mM 1-hydroxybenzotriazole (HOBT), 2-(1H-benzotriazole-1-yl)-1,1,3,3-tetranethyluronium hexafluorophosphate (HBTU) and N,N-diisopropylethylamine (DIEA). The protecting groups were totally removed by treating with a mixture of trifluoroacetic acid (TFA), thioanisole, phenol, water, ethanedithiol and triisopropylsilane (87.5:2.5:2.5:2.5:2.5:2.5) for 2 h at room temperature (25° C.). The peptides were precipitated and washed with ice-cold ether for four times, purified by reverse phase-high performance liquid chromatography (RP-HPLC) and characterized by LC-MS.

In vitro Competitive Binding Assay: The $IC_{50}$ values of DOTA-GluGlu-CycMSH and Ac-GluGlu-CycMSH[DOTA] were determined by using methods described previously (12). B16/F1 cells were harvested and seeded into a 24-well cell culture plate ($5 \times 10^5$/well) and incubated at 37° C. overnight. After being washed once with binding media (MEM with 25 mM HEPES, pH 7.4, 0.2% BSA, 0.3 mM 1,10-phenanthroline), the cells were incubated at 25° C. for 2 h with approximately 50,000 cpm of $^{125}$I-(Tyr$^2$)-NDP-MSH in the presence of increasing concentrations ($10^{-13}$ to $10^{-6}$ M) of DOTA-GluGlu-CycMSH or Ac-GluGlu-CycMSH [DOTA] in 0.3 ml of binding media. The reaction media were aspirated after incubation. Cells were rinsed with 0.5 ml of ice-cold pH 7.4; 0.2% BSA/0.01 M PBS twice and lysed in 0.5 ml of 1 N NaOH for 5 min. The activities associated with cells were measured in a Wallac 1480 automated gamma counter (PerkinElmer, N.J.). The $IC_{50}$ values of the peptides were calculated by using Prism software (GraphPad Software, La Jolla, Calif.).

Results

Figure 15:
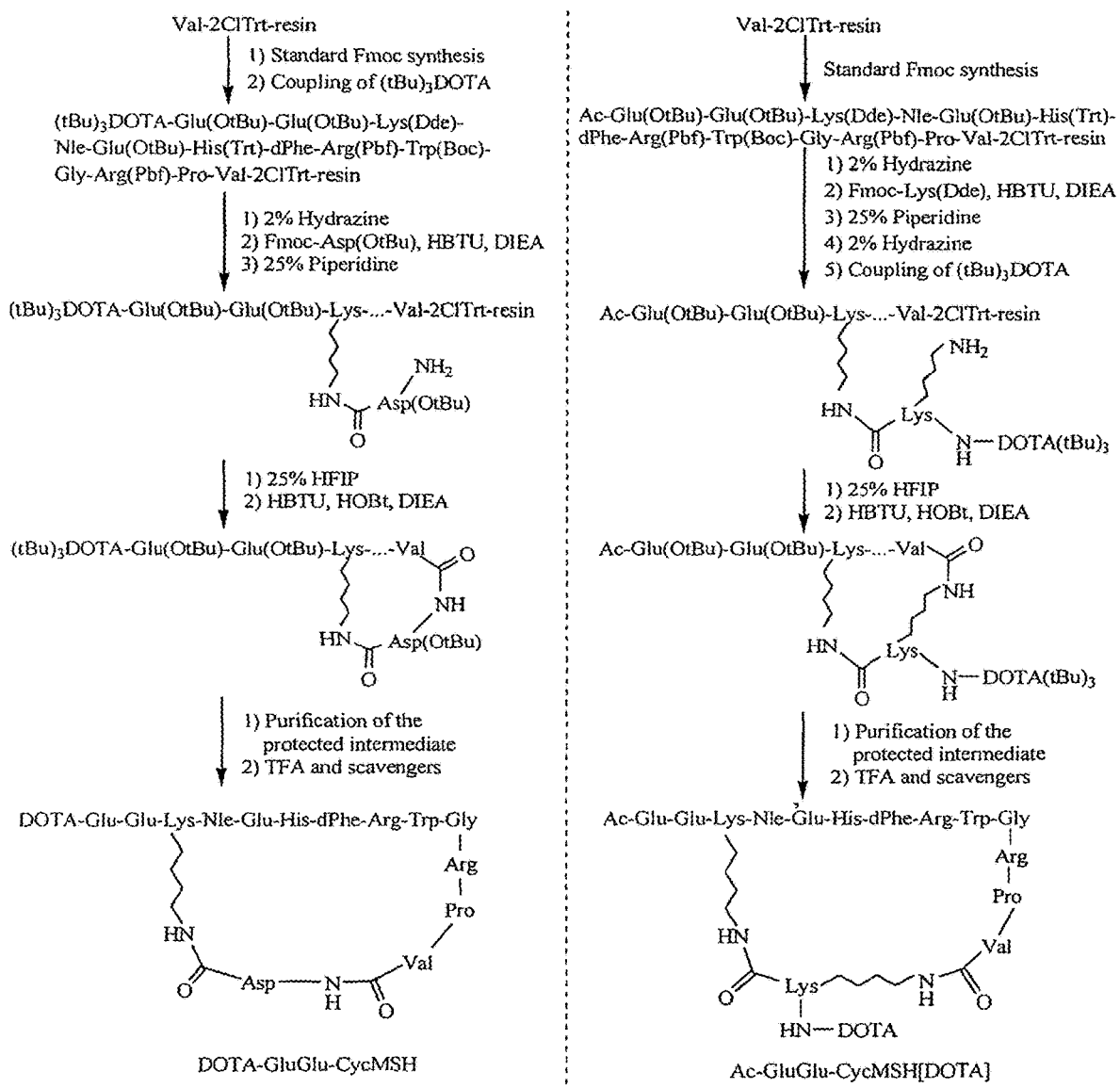
FIG. 15 shows a specific synthesis scheme for compounds which are set forth in examples section 3, which may be adapted and modified generically to compounds according to the present invention.
Figure 16:
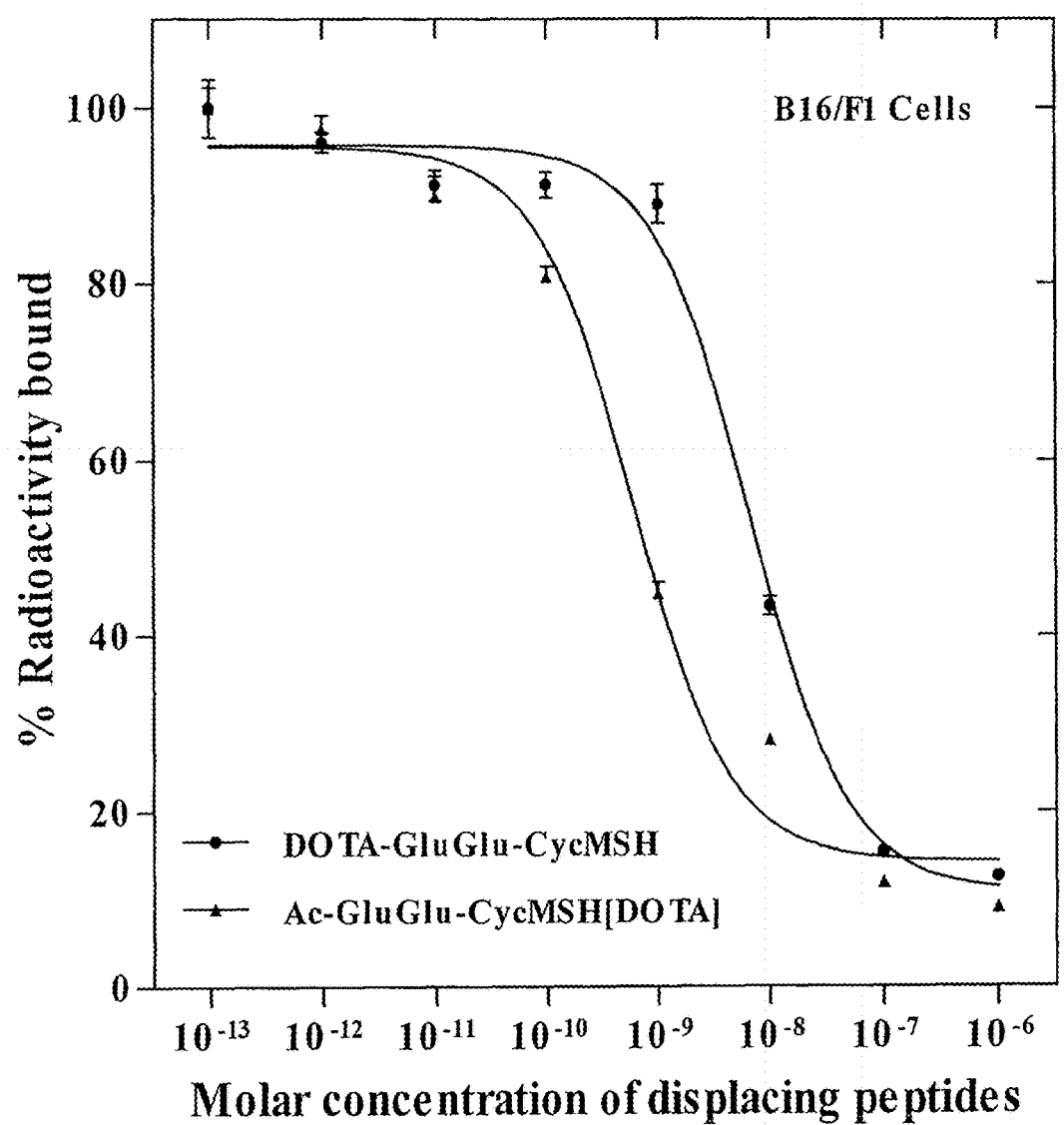
FIG. 16 shows the competitive binding curves of DOTA-GluGlu-CycMSH and Ac-GluGlu-CycMSH[DOTA] in B16/F1 murine melanoma cells. The $IC_{50}$ values of DOTA-GluGlu-CycMSH and Ac-GluGlu-CycMSH[DOTA] were 6.73 nM and 0.60 nM.

DOTA-GluGlu-CycMSH and Ac-GluGlu-CycMSH-DOTA were synthesized, purified by RP-HPLC and the identities of peptides were confirmed by electrospray ionization mass spectrometry. The synthetic schemes are presented in FIG. 15, which represents a minor variation of the general synthetic scheme which is presented in FIG. 2. The competitive binding curves of DOTA-GluGlu-CycMSH and Ac-GluGlu-CycMSH-DOTA are shown in FIG. 15. The $IC_{50}$ values of DOTA-GluGlu-CycMSH and Ac-GluGlu-CycMSH-DOTA were 6.73 nM and 0.60 nM in B16/F1 cells. The results evidence that these compounds may also be used as compounds for imaging and treating melanoma, including metastatic melanoma as otherwise disclosed herein.

The terms and expressions that have been employed in this application are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

REFERENCES

First Set of References

1. Jemal, A., Siegel, R., Ward, E., Murray, T., Xu, J., Thun, M. J. Cancer statistics, 2007. (2007) *CA Cancer J. Clin.* 57, 43-66.
2. Nabi, H. A., Zubeldia, J. M. (2002) Clinical application of 18F-FDG in oncology. *J. Nucl. Med. Technol.* 30, 3-9.
3. Dimitrakopoulou-Strauss, A., Strauss, L. G., Burger, C. (2001) Quantitative PET studies in pretreated melanoma patients: A comparison of 6-[$^{18}$F]fluoro-L-DOPA with $^{18}$F-FDG and $^{15}$O-water using compartment and non-compartment analysis. *J. Nucl. Med.* 42, 248-256.
4. Tatro, J. B., Reichlin, S. (1987) Specific receptors for alpha-melanocyte-stimulating hormone are widely distributed in tissues of rodents. *Endocrinology* 121, 1900-1907.
5. Siegrist, W., Solca, F., Stutz, S., Giuffre, L., Carrel, S.; Girard, J., Eberle, A. N. (1989) Characterization of receptors for alpha-melanocyte-stimulating hormone on human melanoma cells. *Cancer Res.* 49, 6352-6358.
6. Chen, J., Cheng, Z., Hoffman, T. J., Jurisson, S. S., Quinn, T. P. (2000) Melanoma-targeting properties of $^{99m}$Technetium-labeled cyclic α-melanocyte-stimulating hormone peptide analogues. *Cancer Res.* 60, 5649-5658.
7. Miao, Y., Owen, N. K., Whitener, D., Gallazzi, F., Hoffman, T. J., Quinn, T. P. (2002) In vivo evaluation of $^{188}$Re-labeled alpha-melanocyte stimulating hormone peptide analogs for melanoma therapy. *Int. J. Cancer* 101, 480-487.
8. Miao, Y., Whitener, D., Feng, W., Owen, N. K., Chen, J., Quinn, T. P. (2003) Evaluation of the human melanoma targeting properties of radiolabeled alpha-Melanocyte stimulating hormone peptide analogues. *Bioconjug. Chem.* 14, 1177-1184.
9. Miao, Y., Owen, N. K., Fisher, D. R., Hoffman, T. J., Quinn, T. P. (2005) Therapeutic efficacy of a $^{188}$Re labeled α-melanocyte stimulating hormone peptide analogue in murine and human melanoma-bearing mouse models. *J. Nucl. Med.* 46, 121-129.
10. Miao, Y., Hylarides, M., Fisher, D. R., Shelton, T., Moore, H., Wester, D. W., Fritzberg, A. R., Winkelmann, C. T., Hoffman, T. J., Quinn, T. P. (2005) Melanoma therapy via peptide-targeted α-radiation. *Clin. Cancer Res.* 11, 5616-5621.
11. Froidevaux, S., Calame-Christe, M., Tanner, H., Sumanovski, L., Eberle, A. N. (2002) A novel DOTA-α-melanocyte-stimulating hormone analog for metastatic melanoma diagnosis. *J. Nucl. Med.* 43, 1699-1706.
12. Froidevaux, S., Calame-Christe, M., Schuhmacher, J., Tanner, H., Saffrich, R., Henze, M., Eberle, A. N. (2004) A Gallium-labeled DOTA-α-melanocyte-stimulating hormone analog for PET imaging of melanoma metastases. *J. Nucl. Med.* 45, 116-123.
13. Froidevaux, S., Calame-Christe, M., Tanner, H., Eberle, A. N. (2005) Melanoma targeting with DOTA-alpha-melanocyte-stimulating hormone analogs: structural parameters affecting tumor uptake and kidney uptake. *J. Nucl. Med.* 46, 887-895.
14. Sawyer, T. K., Hruby, V. J., Darman, P. S., Hadley, M. E. (1982) [half-Cys$^4$, half-Cys$^{10}$]-α-melanocyte-stimulating hormone: a cyclic α-melanotropin exhibiting superagonist biological activity. *Proc. Natl. Acad. Sci. U.S.A.* 79, 1751-1755.
15. Al-Obeidi, F., Hadley, M. E., Pettitt, B. M., Hruby, V. J. (1989) Design of a new class of superpotent cyclic α-melanotropins based on quenched dynamic simulations. *J. Am. Chem. Soc.* 111, 3413-3416.
16. Al-Obeidi, F., de L. Castrucci, A. M., Hadley, M. E., Hruby, V. J. (1989) Potent and prolonged-acting cyclic lactam analogs of α-melanotropin: design based on molecular dynamics. *J. Med. Chem.* 32, 2555-2561.
17. Fung, S., Hruby, V. J. (2005) Design of cyclic and other templates for potent and selective peptide α-MSH analogues. *Current Opinion in Chem. Biol.* 9, 352-358.
18. Giblin, M. F., Wang, N. N., Hoffman, T. J., Jurisson, S. S., Quinn, T. P. (1998) Design and characterization of α-melanotropin peptide analogs cyclized through rhenium and technetium metal coordination. *Proc. Natl. Acad. Sci. U.S.A.* 95, 12814-12818.
19. Chen, J., Cheng, Z., Owen, N. K., Hoffman, T. J., Miao, Y., Jurisson, S. S., Quinn, T. P. (2001) Evaluation of an $^{111}$In-DOTA-rhenium cyclized α-MSH analog: a novel cyclic-peptide analog with improved tumor-targeting properties. *J. Nucl. Med.* 42, 1847-1855.
20. Aloj, L., Panico, M., Caraco, C., Del Vecchio, S., Arra, C., Affuso, A., Accardo, A., Mansi, R., Tesauro, D., De Luca, S., Pedone, C., Visentin, R., Mazzi, U., Morelli, G., Salvatore, M. (2004) In vitro and in vivo characterization of Indium-111 and Technetium-99m labeled CCK-8 derivatives for CCK-B receptor imaging. *Cancer Biotherapy Radiopharm.* 19, 93-98.
21. Miao, Y., Hoffman, T. J., Quinn, T. P. (2005) Tumor-targeting properties of $^{90}$Y- and $^{177}$Lu-labeled α-melanocyte stimulating hormone peptide analogues in a murine melanoma model. *Nucl. Med. Biol.* 32, 485-493.
22. Miao, Y., Benwell, K., Quinn, T. P. (2007) $^{99m}$Tc and $^{111}$In labeled alpha-melanocyte stimulating hormone peptides as imaging probes for primary and pulmonary metastatic melanoma detection. *J. Nucl. Med.* 48, 73-80.
23. Volkert, W. A., Hoffman, T. J. (1999) Therapeutic radiopharmaceuticals. *Chem. Rev.* 99, 2269-2292.
24. Behr, T. M., Sharkey, R. M., Juweid, M. E., Blumenthal, R. D., Dunn, R. M., Bair, H. J., Wolf, F. G., Becker, W. S., Goldenberg, D. M. (1995) Reduction of the renal uptake of radiolabeled monoclonal antibody fragments by cationic amino acids and their derivatives. *Cancer Res.* 55, 3825-3834.
25. Behr, T. M., Becker, W. S., Sharkey, R. M., Juweid, M. E., Dunn, R. M., Bair, H. J., Wolf, F. G., Goldenberg, D. M. (1996) Reduction of renal uptake of monoclonal antibody fragments by amino acid infusion. *J. Nucl. Med.* 37, 829-833.
26. Béhé, M., Kluge, G., Becker, W., Gotthardt, M., Behr, T. M. (2005) Use of polyglutamic acids to reduce uptake of radiometal-labeled minigastrin in the kidneys. *J. Nucl. Med.* 46, 1012-1015.
27. Rolleman, E. J., Krenning, E. P., Van Gameren, A., Bernard, B. F., De Jong, M. (2004) Uptake of [$^{111}$In-DTPA0]octreotide in the rat kidney is inhibited by colchicine and not by fructose. *J. Nucl. Med.* 45, 709-713.
28. De Jong, M., Barone, R., Krenning, E. P., Bernard, B. F., Melis, M., Vissor, T., Gekle, M., Willnow, T. E., Walrand, S., Jamar, F., Pauwels, S. (2005) Megalin is essential for renal proximal tubule reabsorption of $^{111}$In-DTPA-Octreotide. *J. Nucl. Med.* 46, 1696-1700.
29. Miao, Y., Fisher, D. R., Quinn, T. P. (2006) Reducing renal uptake of $^{90}$Y and $^{177}$Lu labeled alpha-melanocyte stimulating hormone peptide analogues. *Nucl. Med. Biol.* 33, 723-733.

30. Liu, S., He, Z., Hsieh, W. Y., Kim, Y. S., Jiang, Y. (2006) Impact of PKM linkers on biodistribution characteristics of the $^{99m}$Tc-labeled cyclic RGDfK dimer. *Bioconjug. Chem.* 17; 1499-1507.
31. Dijkgraaf, I., Liu, S., Kruijtzer, J. A., Soede, A. C., Oyen, W. J., Liskamp, R. M., Corstens, F. H., Boerman, O. C. (2007) Effects of linker variation on the in vitro and in vivo characteristics of an $^{111}$In-labeled RGD peptide. *Nucl. Med. Biol.* 34; 29-35.
32. Liu, S., Hsieh, W. Y., Jiang, Y., Kim, Y. S., Sreerama, S. G., Chen, X., Jia, B., Wang, F. (2007) Evaluation of a $^{99m}$Tc-labeled cyclic RGD tetramer for noninvasive imaging integrin $\alpha_v\beta_3$-positive breast cancer. *Bioconjug. Chem.* 18; 438-446.
33. Wu, Y., Zhang, X., Xiong, Z., Cheng, Z., Fisher, D. R., Liu, S., Gambhir, S. S., Chen, X. (2005) MicroPET imaging of glioma integrin $\alpha_v\beta_3$ expression using $^{64}$Cu-labeled tetrameric RGD peptide. *J. Nucl. Med.* 46; 1707-1718.
34. Li, Z. B., Cai, W., Cao, Q., Chen, K., Wu, Z., He, L., Chen, X. (2007) $^{64}$Cu-labeled tetrameric and octameric RGD peptides for small-animal PET of tumor $\alpha_v\beta_3$ integrin expression. *J. Nucl. Med.* 48; 1162-1171.
35. Dijkgraaf, I., Kruijtzer, J. A., Liu, S., Soede, A. C., Oyen, W. J., Corstens, F. H., Liskamp, R. M., Boerman, O. C. (2007) Improved targeting of the alpha(v)beta(3) integrin by multimerisation of RGD peptides. *Eur. J. Nucl. Med. Mol. Imaging.* 34; 267-273.

Second Set of References

1. Jemal A, Siegel R, Ward E, et al. Cancer statistics, 2008. *CA Cancer J Clin.* 2008; 58:71-96.
2. Balch C M, Soong S J, Gershenwald J E, et al. Prognostic factors analysis of 17,600 melanoma patients: validation of the American joint committee on cancer melanoma staging system. *J Clin Oncol.* 2001; 19:3622-3634.
3. Gambhir S S. Molecular imaging of cancer with positron emission tomography. *Nat Rev Cancer.* 2002; 2:683-693.
4. Sharma V, Luker G D, Piwnica-Worms D. Molecular imaging of gene expression and protein function in vivo with PET and SPECT. *J Magn Reson Imaging.* 2002; 16:336-351.
5. Alonso O, Martinez M, Delgado L, et al. Staging of regional lymph nodes in melanoma patients by means of $^{99m}$Tc-MIBI scintigraphy. *J Nucl Med.* 2003; 44:1561-1565.
6. Nabi H A, Zubeldia J M. Clinical application of $^{18}$F-FDG in oncology. *J Nucl Med Technol.* 2002; 30:3-9.
7. Dimitrakopoulou-Strauss A, Strauss L G, Burger C. Quantitative PET studies in pretreated melanoma patients: A comparison of 6-[$^{18}$F]fluoro-L-DOPA with $^{18}$F-FDG and $^{15}$O-water using compartment and non-compartment analysis. *J Nucl Med.* 2001; 42:248-256.
8. Tatro J B, Reichlin S. Specific receptors for alpha-melanocyte-stimulating hormone are widely distributed in tissues of rodents. *Endocrinology.* 1987; 121:1900-1907.
9. Siegrist W, Solca F, Stutz S, et al. Characterization of receptors for alpha-melanocyte-stimulating hormone on human melanoma cells. *Cancer Res.* 1989; 49:6352-6358.
10. Chen J, Cheng Z, Hoffman T J, Jurisson S S, Quinn T P. Melanoma-targeting properties of $^{99m}$Technetium-labeled cyclic α-melanocyte-stimulating hormone peptide analogues. *Cancer Res.* 2000; 60:5649-5658.
11. Miao Y, Owen N K, Whitener D, Gallazzi F, Hoffman T J, Quinn T P. In vivo evaluation of $^{188}$Re-labeled alpha-melanocyte stimulating hormone peptide analogs for melanoma therapy. *Int J Cancer.* 2002; 101:480-487.
12. Miao Y, Whitener D, Feng W, Owen N K, Chen J, Quinn T P. Evaluation of the human melanoma targeting properties of radiolabeled alpha-melanocyte stimulating hormone peptide analogues. *Bioconjug Chem.* 2003; 14:1177-1184.
13. Miao Y, Owen N K, Fisher D R, Hoffman T J, Quinn T P. Therapeutic efficacy of a $^{188}$Re labeled α-melanocyte stimulating hormone peptide analogue in murine and human melanoma-bearing mouse models. *J Nucl Med.* 2005; 46:121-129.
14. Miao Y, Hylarides M, Fisher D R, et al. Melanoma therapy via peptide-targeted α-radiation. *Clin Cancer Res.* 2005; 11:5616-5621.
15. Froidevaux S, Calame-Christe M, Tanner H, Sumanovski L, Eberle A N. A novel DOTA-α-melanocyte-stimulating hormone analog for metastatic melanoma diagnosis. *J Nucl Med.* 2002; 43:1699-1706.
16. Froidevaux S, Calame-Christe M, Schuhmacher J, et al. A Gallium-labeled DOTA-α-melanocyte-stimulating hormone analog for PET imaging of melanoma metastases. *J Nucl Med.* 2004; 45:116-123.
17. Froidevaux S, Calame-Christe M, Tanner H, Eberle A N. Melanoma targeting with DOTA-alpha-melanocyte-stimulating hormone analogs: structural parameters affecting tumor uptake and kidney uptake. *J Nucl Med.* 2005; 46:887-895.
18. Miao Y, Gallazzi F, Guo H, Quinn T P. $^{111}$In-labeled lactam bridge-cyclized alpha-melanocyte stimulating hormone peptide analogues for melanoma imaging. *Bioconjug Chem.* 2008; 19:539-547.
19. Sawyer T K, Hruby V J, Darman P S, Hadley M E. [half-Cys$^4$, half-Cys$^{10}$]-α-melanocyte-stimulating hormone: a cyclic α-melanotropin exhibiting superagonist biological activity. *Proc Natl Acad Sci USA.* 1982; 79:1751-1755.
20. Al-Obeidi F, Hadley M E, Pettitt B M, Hadley M E. Design of a new class of superpotent cyclic α-melanotropins based on quenched dynamic simulations. *J Am Chem Soc.* 1989; 111:3413-3416.
21. Al-Obeidi F, de L Castrucci A M, Hadley M E, Hruby V J. Potent and prolonged-acting cyclic lactam analogs of α-melanotropin: design based on molecular dynamics. *J Med Chem.* 1989; 32:2555-2561.
22. Fung S, Hruby V J. Design of cyclic and other templates for potent and selective peptide α-MSH analogues. *Current Opinion in Chem Biol.* 2005; 9:352-358.
23. Fidler I J. Biological behavior of malignant melanoma cells correlated to their survival in vivo. *Cancer Res.* 1975; 35:218-224.
24. Cheng Z, Mahmood A, Li H, Davison A, Jones A G. [$^{99m}$TcOAADT]-(CH$_2$)$_2$-NEt$_2$: a potential small-molecule single-photon emission computed tomography probe for imaging metastatic melanoma. *Cancer Res.* 2005; 65:4979-4986.
25. Winkelmann C T, Figueroa S D, Rold T L, Volkert W A. Microimaging characterization of a B16-F10 melanoma metastasis mouse model. *Molecular Imaging.* 2006; 5:105-114.
26. Fidler I J, Kripke M L. Metastasis results from preexisting variant cells within a malignant tumor. *Science.* 1977; 197:893-895.
27. Vantyghem S A, Postenka C O, Chambers A F. Estrous cycle influences organ-specific metastasis of B16F10 melanoma cells. *Cancer Res.* 2003; 63:4763-4765.

28. Yang M, Jiang P, An Z, et al. Genetically fluorescent melanoma bone and organ metastasis models. *Clin Cancer Res.* 1999; 5:3549-3559.
29. Yang M, Baranov E, Jiang P, et al. Whole-body optical imaging of green fluorescent protein-expressing tumors and metastases. *Proc Natl Acad Sci USA.* 2000; 97:1206-1211.
30. Hoffman R M. Green fluorescent protein imaging of tumour growth, metastasis, and angiogenesis in mouse models. *Lancet Oncol.* 2002; 3:546-556.
31. Arguello F, Baggs R B, Frantz C N. A murine model of experimental metastasis to bone and bone marrow. *Cancer Res.* 1988; 48:6876-6881.
32. Volkert W A, Hoffman T J. Therapeutic radiopharmaceuticals. *Chem Rev.* 1999; 99:2269-2292.
33. Miao Y, Benwell K, Quinn T P. $^{99m}$Tc- and $^{111}$In-labeled α-melanocyte-stimulating hormone peptides as imaging probes for primary and pulmonary metastatic melanoma detection. *J Nucl Med.* 2007; 48:73-80.
34. Otte A, Jermann E, Behe M, et al. A powerful new tool for receptor-mediated radionuclide therapy. *Eur J Nucl Med.* 1997; 24:792-795.
35. Otte A, Mueller-Brand J, Dellas S, Nitzsche E U, Hellmann R, Maecke H R. Yttrium-90-labelled somatostatin-analogue for cancer treatment. *Lancet.* 1998; 351: 417-418.
36. Zamora P O, Bender H, Gulhke S, et al. Pre-clinical experience with Re-188-RC-160, a radiolabeled somatostatin analog for use in peptide-targeted radiotherapy. *Anticancer Res.* 1997; 17:1803-1808.
37. De Jong M, Breeman W A P, Bernard B F, et al. [$^{177}$Lu-DOTA$^0$, Tyr$^3$]octreotate for somatostatin receptor-targeted radionuclide therapy. *Int J Cancer.* 2001; 92:628-633.

Third Set of References

1. Miao, Y., Gallazzi, F., Guo, H., Quinn, T. P. (2008) $^{111}$In-labeled lactam bridge-cyclized α-melanocyte stimulating hormone peptide analogues for melanoma imaging. *Bioconjug. Chem.* 19, 539-547.
2. Haixun Guo, Nalini Shenoy, Benjamin M. Gershman, Jianquan Yang, Larry A. Sklar, Yubin Miao. Metastatic melanoma imaging with an 111In-labeled lactam bridge-cyclized alpha-melanocyte stimulating hormone peptide. *Nuclear Medicine and Biology*, 2009; 36:in press.

The invention claimed is:

1. A compound of the chemical structure:

Wherein Y is a chelate group, said chelate group incorporating or complexing with a radioisotope;
Each X is independently an amino acid linker

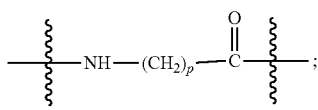

ABC is an amino acid linker wherein
A is absent or is a neutral or negatively charged amino acid at physiological pH;
B is a neutral or negatively charged amino acid at physiological pH;
C is absent or is a neutral or negatively charged amino acid at physiological pH;

m is 0 or 1;
n is 0 or 1;
p is an integer from 0 to 20;
q is 1, and
Cycpeptide is a cyclic peptide having a formula:

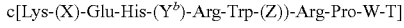

Wherein X is norleucine (Nle), leucine or isoleucine;
$Y^b$ is D-phenylalanine or L-phenylalanine;
Z is glycine or alanine;
W is valine, leucine or isoleucine;
T is aspartic acid, glutamic acid or a

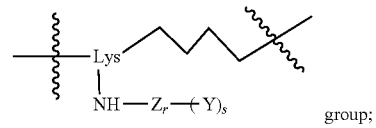

group;

Where Z is an amino acid residue or an amino acid linker according to

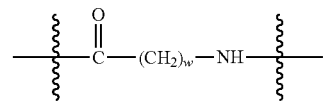

j is 0, 1 or 2;
r is an integer from 0 to 5;
s is 1;
w is 0 to 20; or
a pharmaceutically acceptable salt thereof,
wherein said radioisotope is selected from the group consisting of $^{86}$Y, $^{90}$Y, $^{111}$In, $^{177}$Lu, $^{225}$Ac, $^{212}$Bi, $^{213}$Bi, $^{66}$Ga, $^{67}$Ga, $^{68}$Ga, $^{64}$Cu, $^{67}$Cu, $^{71}$As, $^{72}$As, $^{76}$As, $^{77}$As, $^{65}$Zn, $^{48}$V, $^{203}$Pb, $^{209}$Pb, $^{212}$Pb, $^{166}$Ho, $^{149}$Pm, $^{153}$Sm, $^{201}$Tl, $^{188}$Re, $^{186}$Re and $^{99m}$Tc.

2. The compound according to claim 1 wherein said radioisotope is polycationic.

3. The compound according to claim 1 wherein n is 1.

4. The compound according to claim1, wherein j is 1, r is 1 to 5 and w is 2 to 8.

5. The compound according to claim 1 wherein q is 1, m is 0, n is 1, j is 1 and T is aspartic acid or glutamic acid.

6. The compound according to claim 1 wherein Y is a radical of 1,4,7,10-tetraazacyclododecane-1,4,7,10-tetraacetic acid (DOTA), 4,11-bis(carboxymethyl)-1, 4,8,11-tetraazabicyclo[6.6.2]hexadecane (CB-TE2A), 1,4,7-triazacyclononane-1,4,7-triacetic acid (NOTA), Diethylenetriaminepentaacetic acid (DTPA), Mercaptoacetyltriglycine (MAG$_3$) or 4,5-bis(2-mercaptoacetamido) pentanoic acid.

7. The compound according to claim 1 wherein Y is a radical of DOTA.

8. The compound according to claim 1 wherein q is 0, W is valine, X is norleucine, $Y^b$ is D-phenylalanine, Z is glycine and T is a

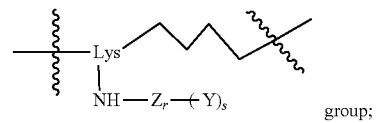

group;

Where Z is an amino acid residue or an amino acid linker according to

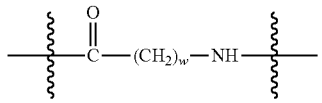

j is 0, 1 or 2;
r is an integer from 0 to 5;
s is 1;
w is 0 to 20; and
Y is complexed with said radioisotope.

9. The compound according to claim 8 wherein j is 1, r is 0 or 1; and w is 2 to 8.

10. The compound according to claim 8 wherein Y is a radical of 1,4,7,10-tetraazacyclododecane-1,4,7,10-tetraacetic acid (DOTA), 4,11-bis(carboxymethyl)-1, 4,8,11-tetraazabicyclo[6.6.2]hexadecane (CB-TE2A), 1,4,7-triazacyclononane-1,4,7-triacetic acid (NOTA), Diethylenetriaminopentaacetic acid (DTPA), Mercaptoacetyltriglycine ($MAG_3$) or 4,5-bis(2-mercaptoacetamido) pentanoic acid.

11. The compound according to claim 8 wherein m is 0.
12. The compound according to claim 8 wherein n is 1.
13. The compound according to claim 8 wherein r is 0.
14. The compound according to claim 8 wherein m is 0 and n is 1.
15. The compound according to claim 8 wherein m is 0, n is 1 and A is absent.
16. The compound according to claim 8 wherein A is glycine, glutamic acid or aspartic acid, B is glutamic acid or aspartic acid and C is absent.

17. The compound according to claim 1 wherein said radioisotope is selected from the group consisting of $^{111}$In, $^{86}$Y, $^{66}$Ga, $^{68}$Ga, $^{203}$Pb, $^{64}$Cu and $^{99m}$Tc, $^{90}$Y, $^{177}$Lu, $^{186}$Re, $^{188}$Re, $^{212}$Bi/$^{212}$Pb, $^{213}$Bi, $^{149}$Pm, $^{166}$Ho and $^{153}$Sm.

18. A pharmaceutical composition comprising an effective amount of a compound comprising a radioisotope according to claim 1 in combination with a pharmaceutically acceptable carrier, additive or excipient.

19. The composition according to claim 18 wherein said compound is combined with at least one agent selected from the group consisting of dacarbazine (DTIC), interleukin-2 (IL-2) and α-interferon.

20. A method of diagnosing the existence or absence of melanoma in a patient at risk for melanoma comprising administering to said patient a compound according to claim 1; imaging said patient to determine if tissue in said patient exhibits elevated expression of MSH receptors; and diagnosing said patient as having melanoma if said tissue evidences elevated expression of MSH receptors in comparison to a standard.

21. A method of treating melanoma in a patient in need of therapy comprising administration to said patient an effective amount a composition according to claim 18.

22. The method according to claim 21 wherein said compound is coadministered with an effective amount of at least one agent selected from the group consisting of dacarbazine (DTIC), interleukin-2 (IL-2) and α-interferon.

23. A method of monitoring therapy of a patient in the treatment of melanoma, said method comprising administering to a patient undergoing melanoma treatment an imaging effective amount of a compound according to claim 1, imaging said patient to determine if tissue in said patient exhibits elevated expression of MSH receptors; and comparing the results of said imaging step with a standard.

* * * * *